(12) United States Patent
Berndt

(10) Patent No.: US 7,643,134 B2
(45) Date of Patent: Jan. 5, 2010

(54) APPARATUS FOR PERFORMING OPTICAL MEASUREMENTS ON BLOOD CULTURE BOTTLES

(75) Inventor: Klaus W. Berndt, Cockeysville, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 258 days.

(21) Appl. No.: 11/573,673

(22) PCT Filed: Aug. 16, 2005

(86) PCT No.: PCT/US2005/029058

§ 371 (c)(1),
(2), (4) Date: Oct. 18, 2007

(87) PCT Pub. No.: WO2006/023470

PCT Pub. Date: Mar. 2, 2006

(65) Prior Publication Data

US 2008/0259313 A1 Oct. 23, 2008

(51) Int. Cl.
*G01N 33/48* (2006.01)
(52) U.S. Cl. .................... 356/39; 356/239.6
(58) Field of Classification Search .............. 356/39, 356/239.4, 239.5, 239.6; 382/133, 134
See application file for complete search history.

(56) References Cited

U.S. PATENT DOCUMENTS

| 5,427,920 A | 6/1995 | Berndt et al. |
| 5,510,620 A | 4/1996 | Achter et al. |
| 5,516,692 A | 5/1996 | Berndt |
| 5,770,394 A | 6/1998 | Berndt |
| 6,239,869 B1 | 5/2001 | Heuft et al. |

FOREIGN PATENT DOCUMENTS

CH 613045 A * 8/1979

OTHER PUBLICATIONS

International Search Report, PCT/US2005/029058, dated Dec. 1, 2005.

* cited by examiner

*Primary Examiner*—Roy Punnoose

(57) ABSTRACT

An apparatus and method for rapidly distinguishing positive blood cultures from negative bloodcultures in sealable containers, and for determining the combination of blood volume and hematocrit in a sealable container. The apparatus comprises an optical source for illuminating the culture with a light beam under an oblique angle to generate an asymmetric spatial distribution of backscattered light, which is imaged onto an imaging detector connected to a data analyzer.

82 Claims, 30 Drawing Sheets

FIG.2A
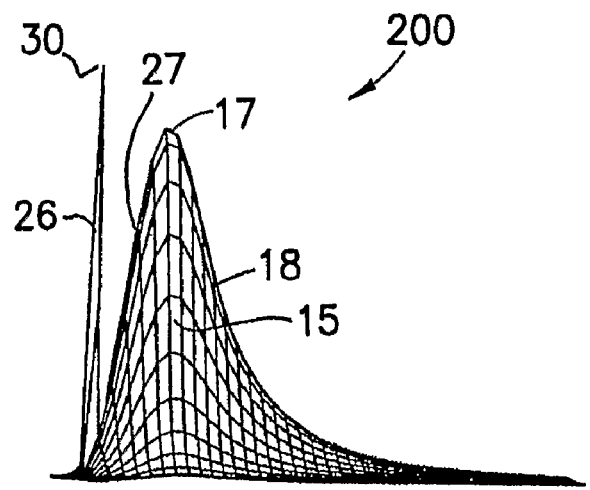
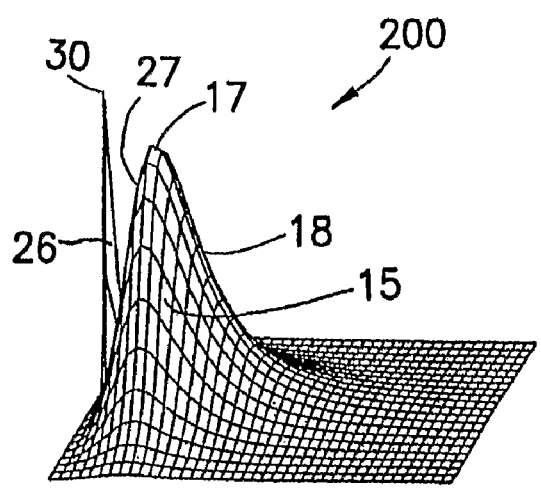
FIG.2B

APPARATUS FOR PERFORMING OPTICAL MEASUREMENTS ON BLOOD CULTURE BOTTLES

BACKGROUND OF THE INVENTION

1. Field of the Invention

The present invention relates generally to the field of growth-based detection of microorganisms in sealable containers, such as blood culture bottles. The present invention relates specifically to a system and method for performing optical measurements on a sealable container that can be used to rapidly distinguish positive blood cultures from negative blood cultures, and determine the combination of blood volume and hematocrit in a sealable container.

2. Description of the Related Art

Usually, the presence of biologically active agents such as bacteria or mycobacteria in a patient's body fluid is determined using culture vials. A small quantity of body fluid is injected through the enclosing rubber septum into the sterile vial containing a culture medium. The vial is incubated at 37° C. and monitored for bacterial growth. Known methods preferably detect changes in the carbon dioxide content of the culture bottles, which is a metabolic by-product of the bacterial growth. Changes in the carbon dioxide concentration are usually monitored using chemical sensors disposed on the inner walls of the culture bottles. The chemical sensors respond to changes in the carbon dioxide concentration by changing their color or by changing their fluorescence intensity (see, for example, Thorpe et al. "BacT/Alert: An automated calorimetric microbial detection system", J. Clin. Microbiol., July 1990, pp. 1608-12; and U.S. Pat. Nos. 4,945,060, 5,217,875, 5,266,486, 5,372,936, and 5,580,784, the entire contents of which are incorporated herein by reference). It has also been suggested to employ carbon dioxide-dependent and/or oxygen-dependent changes in the fluorescence lifetime of fluorescent sensor materials (see, for example, U.S. Pat. Nos. 5,593,854, 5,686,300, 6,074,870, and 6,080,574, the entire contents of which are incorporated herein by reference).

However, these and other known methods generally do not take into account certain factors relevant to the reliability of the detection. These factors include a sufficiently large blood volume for detection and the question of any time delay between extraction and detection.

With regards to the blood volume factor, for the timely and efficient recovery of bacteria from blood samples, it has been found that a sufficiently large blood volume is required (see, for example, Jonsson et al. "Theoretical aspects of detection of bacteremia as a function of the volume of blood cultured", APMIS 1993 (101:595-601); Mermel et al. "Detection of bacteremia in adults—Consequences of culturing an inadequate volume of blood", Annals Internal Med 1993 (119: 270-272); Arpi et al. "Importance of blood volume cultured in the detection of bacteremia", Eur J Clin Microbiol Infect Dis 1989 (8:838-842); Isaacman et al. "Effect of number of blood cultures and volume of blood on detection of bacteremia in children", J Pediatr 1996 (128:190-195); Li et al. "Effects of volume and periodicity on blood cultures", J Clin Microbiol 1994 (32:2829-2831); Wilson et al. "Controlled evaluation of Bact/Alert standard anaerobic and FAN anaerobic blood culture bottles for the detection of bacteremia and fungemia", J Clin Microbiol 1995 (33:2265-2270); Wormser et al. "Improving the yield of blood cultures for patients with early Lyme Disease", J Clin Microbiol 1998 (36:296-298); and Shafazand et al. "Blood cultures in the critical care unit—Improving utilization and yield", Chest 2002 (122:1727-1736), the entire contents of which are incorporated herein by reference).

The need for employing a large volume of blood in culture bottles arises because, depending on the microorganism species, the number of cell forming units per mL of patient blood may be very low. In practice, and depending on the status of a patient, smaller than optimum amounts of blood are frequently used, which has a negative impact on the reliability of such tests.

Up to this point in time, however, no routine method for the blood volume determination has been introduced into the market. Weighing of the sample container after filling and subtracting an average weight has been used in some studies (see Mensa et al. "Yield of blood cultures in relation to the cultured blood volume in BACTEC 6A bottles", Med Clin (Barcelona) 1997 (108:521-523), the entire contents of which are incorporated herein by reference). Due to the variability in the weight of individual containers, however, this weighing method suffers from substantial errors, in particular if a low blood volume is involved.

As known to those skilled in the art, the metabolism of the blood itself, independent of any bacterial activity within the container, contributes to the observed increase in the growth of the concentration of carbon dioxide and, may, therefore, cause false-positive culture results. The magnitude of this artifact depends on the blood volume, in that the magnitude is larger the higher the blood volume. As a consequence, much effort is directed toward optimization of sophisticated detection algorithms in an attempt to achieve a shorter time-to-detection while avoiding false-positive culture results (see, for example, Marchandin et al. "Detection kinetics for positive blood culture bottles by using the VITAL automated system", J Clin Microbiol 1995 (33:2098-2101) and Chapin et al. "Comparison of BACTEC 9240 and Difco ESP blood culture systems for detection of organisms from vials whose entry was delayed", J Clin Microbiol 1996 (34:543-549), the entire contents of which are incorporated herein by reference).

With regards to the time delay factor, blood culture containers, once they have been inoculated with a patient's blood, should preferably be immediately loaded onto an instrumented blood culture detection system. It is well known, however, that a substantial time delay frequently occurs between the time of inoculation and the time of incubation in an instrument. In some countries, delay times up to 48 hours can be expected. This "delayed container entry" phenomenon may cause serious problems if, during the delay time period, the blood culture container is experiencing elevated temperatures that may already support bacterial growth. As a consequence, the container may be already "positive" (i.e., may contain a fully developed population of microorganisms), when the container arrives at the detection instrument. It would not be advisable, of course, to incubate the container, wait for thermal equilibration to 35 degrees Celsius, and then monitor the container for the occurrence of further bacterial growth. Instead, it would be of great advantage if one could rapidly check the incoming bottle for possible "positivity", and, if it is already positive, re-direct the container to an instrument that performs a microorganism identification so that appropriate antibiotics can be selected for treating the patient.

In addition, if a "delayed" blood culture container contains already a fully developed microorganism population at the time it arrives at an instrumented detection system, the system's sensor will not see a typical transient. Therefore, the system can only rely on absolute detection signal levels.

Depending on the performance characteristics of the sensing method, this represents a higher challenge than under typical monitoring conditions, in particular if culture bottles with highly varying blood amounts are expected.

Accordingly, there exists a need for systems and methods capable of rapidly distinguishing positive blood cultures from negative blood cultures and of determining the combination of the blood volume and the hematocrit of a blood sample after extraction from the human body.

SUMMARY OF THE INVENTION

According to an embodiment of the present invention, an apparatus makes optical measurements on a container comprising a liquid sample, e.g., a mixture of growth media and blood. The apparatus is equipped with an optical source capable of directing a light beam onto a wall of the container at a predetermined location, such that the beam deviates from a normal to the bottle wall at the location by an angle, thereby generating an asymmetric spatial distribution of light backscattered from any mixture of growth media and blood in the container near the location, an imaging device to image the spatial distribution of light backscattered from the mixture of growth media and blood in the container near the location, generally into a plane, wherein the imaging device is located so that the light beams reflected by the outer and inner container wall interfaces are not entering the imaging device, and an imaging detector.

In a further embodiment, the image detector is connected to a data analyzing system for extracting analytical features of the asymmetric spatial light distribution, and for providing data. Such features and data may be used, in one aspect, for characterizing the status of the mixture of growth media and blood relative to the presence or absence of a developed microorganism population within the sealable container, or relative to the combination of the hematocrit and the amount of blood present within the sealable container.

According to a further embodiment of the present invention, a method for performing optical measurements on sealable containers comprises providing a container comprising a liquid sample, directing a light beam onto a wall of the container at a first location, wherein the light beam deviates from a normal to the container wall at the first location by a first angle, thereby generating an asymmetric spatial distribution of backscattered light from the sample near the first location, detecting at least portions of the asymmetric spatial distribution of backscattered light generally into a plane, while substantially avoiding detecting portions of the light beams reflected by the outer and inner container wall interfaces, and extracting analytical features from the asymmetric spatial distribution of backscattered light.

BRIEF DESCRIPTION OF THE DRAWINGS

FIG. 2A shows a side view of a three dimensional (3D) data presentation illustrating a combined backscattered light distribution comprised of an asymmetric spatial backscattered light distribution and a backscatter phenomenon from an incoming light beam generated at an inner wall-liquid interface according to an embodiment of the present invention;

FIG. 2B shows a perspective three dimensional data presentation illustrating the combined backscattered light distribution comprised of the asymmetric spatial backscattered light distribution and the backscatter phenomenon from the incoming light beam generated at an inner wall-liquid interface according to an embodiment of the present invention;

DETAILED DESCRIPTION OF THE PREFERRED EMBODIMENTS

Figure 1C:
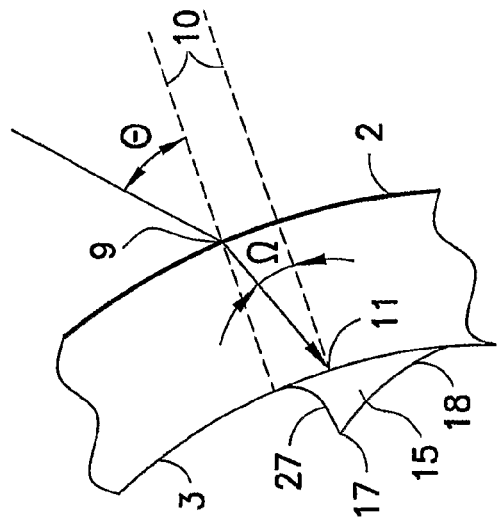
FIG. 1C illustrates a detailed view of an incoming light beam incident upon and refracted through the wall of a blood culture bottle.

Several embodiments of the present invention will now be described in detail with reference to the annexed drawings. In the drawings, the same or similar elements are denoted by the same reference numerals even though they are depicted in different drawings.

The apparatus for performing optical measurements on sealable containers including blood culture, according to an embodiment of the present invention, includes a container having a liquid sample therein, typically a sealable container, and typically a cylindrical container that contains a mixture of growth media and blood. In a preferred embodiment, the sealable container is a blood culture bottle. To perform a measurement, it is advantageous to turn the container two or three times upside down in order to generate a homogeneous suspension. The suspension is then substantially stable over an extended period of time, such as a quarter of an hour or even longer. Advanced blood culture media may contain resin beads that absorb antibiotics. In this case, a few seconds waiting period after turning a bottle is preferred before any measurement is performed. This short period of time is sufficient for the beads to settle. The container is optically transparent to the wavelength of light used.

In one embodiment, the apparatus for performing optical measurements includes an optical source adapted to direct a light beam onto the wall of the container. The light beam deviates from a normal to the container wall by a certain angle, generating an asymmetric spatial distribution of light backscattered from the liquid in the container near the known location. The apparatus of this embodiment further includes an imaging device to image the spatial distribution of light backscattered from the mixture of growth media and blood in the bottle near the known location, typically into a plane. The imaging device is advantageously located so that the light beams reflected by the outer and inner bottle wall interfaces do not enter the imaging device.

The apparatus according to an embodiment of the present invention, further includes a photodetector in the plane, suitable for recording at least parts of the imaged spatial distribution of backscattered light. The photodetector is typically connected with a data analyzing system for extracting analytical features of the asymmetric spatial light distribution, and for providing data. The features and data may be useful for characterizing the status of the mixture of growth media and blood relative to the presence or absence of a developed microorganism population within the container, or relative to the combination of the hematocrit and the amount of blood present within the bottle.

Figure 1A:
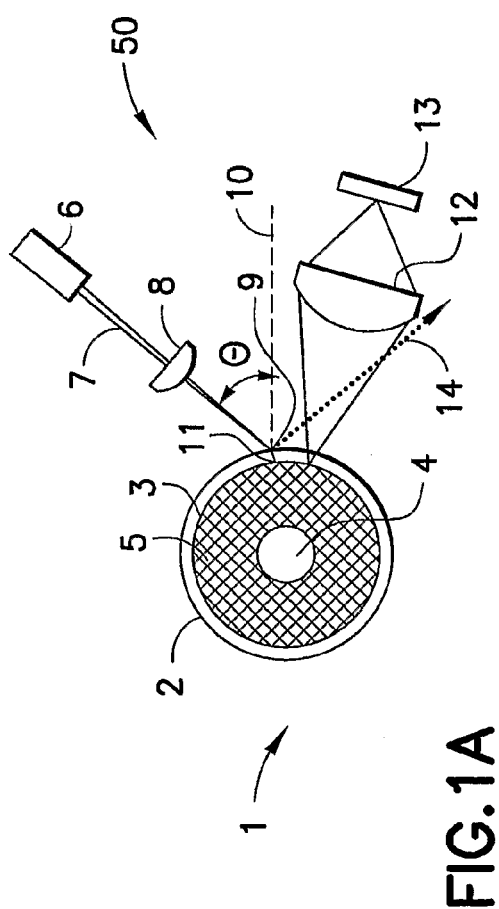
FIG. 1A illustrates schematically the optical arrangement in a first apparatus according to an embodiment of the present invention having an imaging photodetector.

FIG. 1A illustrates schematically the optical arrangement of an apparatus according to an embodiment of the present invention having an imaging detector. The term "imaging detector" refers to any photodetector, or its equivalents, suitable for recording a spatial one-dimensional or two-dimensional light distribution.

In FIG. 1A, a blood culture bottle (1) is shown containing an outer air-wall interface (2), an inner wall-liquid interface (3), a typical rubber septum (4), and the liquid blood culture suspension (5) (e.g., a mixture of growth media and blood). The optical source (6) directs a light beam (7) toward a lens (8) that focuses light beam (7) onto a small spot at the air-wall interface (2) at a primary beam impact point (9). At the primary beam impact point (9) the light beam (7) is refracted toward a point on the inner wall-liquid interface (3). The point on the inner wall-liquid interface (3) where the refracted light beam (7) hits is the secondary beam impact point (11). At the secondary beam impact point (11), light beam (7) is again refracted into the liquid suspension (5), wherein the photons transported by light beam (7) experience multiple scattering and absorption events, resulting in a spatial distribution of backscattered photons that are re-emitted by liquid suspension (5). Within the intensity and distribution of the spatial distribution of the backscattered photons, information regarding the contents of the liquid suspension (5) can be extracted.

According to this embodiment, located near the spatial distribution of backscattered photons that are re-emitted by liquid suspension (5) are an imaging device (12) and a photodetector (13). The imaging device (12) can be, for example, a simple lens, a cylindrical lens, an objective lens, or an array of optical fibers in which the fiber inputs are positioned in proximity to the outer bottle wall interface, and the fiber outputs of said array are in proximity to the CCD reader (24). Such a fiber-optic arrangement is frequently referred to as a "proximity-focus configuration. Other light focusing devices that operate in a substantially similar manner can also be used in place of imaging device (12). Imaging device (12) generates an image of the spatial light distribution in an imaging plane, where the photodetector (13), suitable for recording at least parts of the imaged spatial distribution of backscattered light, is positioned. Photodetector (13) can be, for example, an opto-electronic camera, a digital 2D camera, a two-dimensional (2D) charge coupled device (CCD) array, a linear CCD array, or can be a "non-imaging" photodetector that moves along an axis to record at least parts of the light distribution. Alternatively, photodetector (13) can be a "non-imaging" stationary photodetector, wherein an imaging device (12) moves along an axis to record parts of the light distribution. Other light gathering and measuring devices that operate in substantially the same manner can also be used in place of photodetector (13).

Figure 1B:
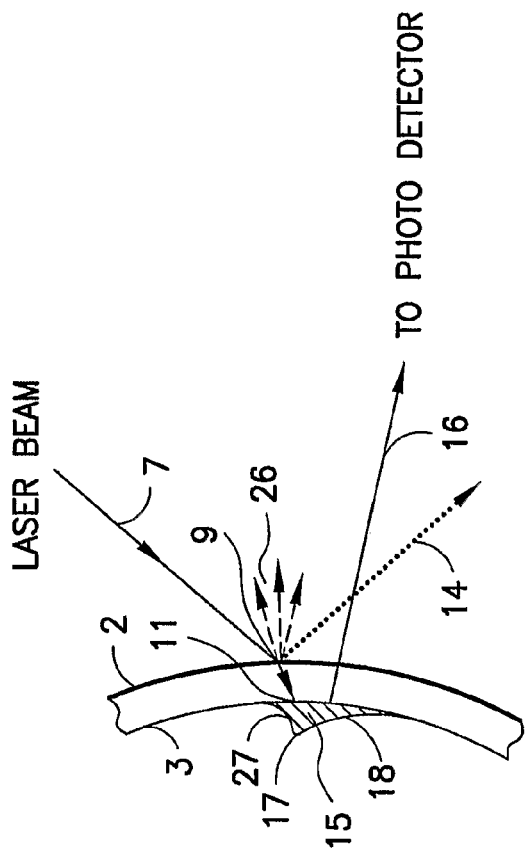
FIG. 1B illustrates details of illumination of a sample in an apparatus according to FIG. 1.

As illustrated in FIGS. 1A and 1B, light beam (7) is directed onto the wall of the blood culture bottle (1) in such a way that light beam (7) deviates from a normal (10) to the bottle wall at the primary beam impact point (9) by a certain angle. The light beam (7) can be oriented such that it propagates within a plane substantially perpendicular to the bottle's axis of symmetry. The light beam (7) can also be oriented such that it propagates within a plane substantially parallel to the bottle's axis of symmetry. These two beam orientations produce a substantially regular spatial light distribution that facilitates subsequent data analysis. Other beam orientations are also possible, as long as the light beam (7) deviates from the normal to the bottle wall at the location of primary beam impact point (9) by a known angle. In the configuration shown in FIG. 1A, the primary beam impact point (9) at which the light beam (7) impinges on the bottle (1) is on a cylindrical part of the bottle. In alternative embodiments of the present invention, however, light beam (7) can also be directed toward a non-cylindrical part of the bottle (1) (e.g., the conical neck part of bottle (1)), or toward the bottom of bottle (1).

In the apparatus of FIG. 1A, light beam (7) is directed toward the cylindrical part of the bottle and is oriented so that it propagates within a plane substantially perpendicular to the bottle's axis of symmetry. In this embodiment, the angle Θ between light beam (7) and the normal to the bottle wall (10) is approximately 45 degrees. Angles between zero and 90 degree are possible, but in one embodiment of the present invention, angle Θ ranges from about 25 degrees to about 45 degrees. In another embodiment of the present invention, angle Θ is about 35 degrees.

There are several reasons why light beam (7) is advantageously not directed at a right angle to the blood culture bottle wall. First, light beam (7), as it meets the air-wall interface at primary beam impact point (9), generates a strong back reflection due to the difference in the index of refraction between air and any bottle wall material. By using a non-zero angle Θ, imaging device (12) can be positioned so that the light beam (14) reflected by the outer bottle wall interface at primary beam impact point (9) does not enter the imaging device (12). The same holds for a second back reflection originating at the inner wall-liquid interface (3) at secondary beam impact point (11). This second back reflection is less intensive than the back reflection from the outer air-wall interface (2) since the difference in the index of refraction between any bottle wall material and the liquid blood culture sample is smaller.

A second reason for directing light beam (7) at an oblique angle onto the bottle wall is that there is not only the reflected light beam (14) that creates a specular back reflection originating at primary beam impact point (9), but also an unpredictable backscatter phenomenon (backscatter) (26) as illustrated in FIG. 1B. This backscatter (26) has its origin in tiny imperfections in the outer air-wall interface (2) of bottle (1), such as small cracks or even impurities such as fingerprints and dust. Unpredictability means that its intensity will widely vary, even among multiple recordings on the very same bottle. Backscatter (26) is generated into a relatively wide conical region and, consequently, enters imaging device (12), causing spike-like error signals on photodetector (13). If light beam (7) is directed at a normal incidence onto bottle (1), the spike-like error signal would be recorded very close to the center of the spatial distribution of backscattered photons that represent the signals of interest. This region, which contains valuable information about the status of the liquid suspension (5), would then be highly impacted by the spike-like error signal, and no reliable measurements could be possible.

Directing light beam (7) onto the bottle wall under an oblique angle substantially overcomes the problem discussed above. As is illustrated schematically in FIG. 1B, light beam (7) that arrives at an angle at the inner wall-liquid interface (3) at location (11) causes an asymmetric spatial backscatter light distribution (15) exhibiting a peak (17), a slowly decaying flank (18) on the side away from the incoming light beam (7), and a fast decaying flank (27) on the side of the incoming light beam (7). Significantly, backscatter (26), which is generated at the outer wall interface at the primary beam impact point (9) is detected by imaging device (12) and photodetector (13) oriented along direction (16) and positioned on the edge of the asymmetric spatial backscatter light distribution (15). The asymmetric spatial backscattered light distribution (15) and backscatter (26) combine to form the combined backscattered light distribution (200) that is described in greater detail below.

Backscatter (26) is detected at a position on the side of the fast decaying flank (27) of the asymmetric spatial backscatter distribution (15), that is, toward the direction of the incoming light beam (7). Consequently, peak (17), slowly decaying flank (18), and fast decaying flank (27) are not disturbed by the backscatter (26), and reliable measurements can be made. This situation is illustrated further in FIGS. 2A and 2B.

FIG. 2A shows a side view of a 3D data presentation illustrating a combined backscattered light distribution (200) comprised of an asymmetrical backscatter light distribution (15) generated at the inner wall-liquid interface (3) and a narrow backscatter (26) with spike (30) from the incoming light beam (7) generated at the outer air-wall interface (2). FIG. 2B shows a perspective 3D data presentation illustrating the same combined backscattered light distribution (200) as shown in FIG. 2A. As can be seen from FIGS. 2A and 2B, the backscatter (26) of FIG. 1B is located far enough away from the asymmetric backscatter light distribution (15) so that an analysis of it is not impaired.

Figure 2C:
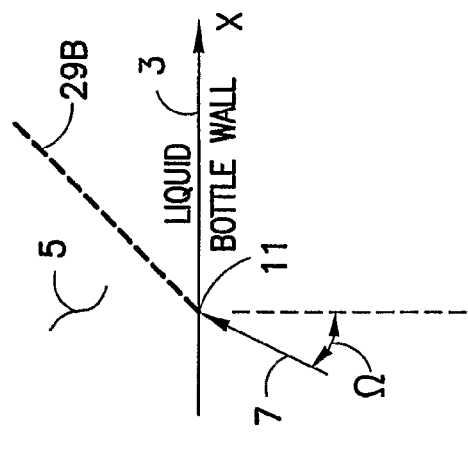
FIG. 2C illustrates, as a dashed line, locations inside a liquid blood culture where a first group of photons are backscattered, for the case where an incoming light beam coincides with the normal to the glass wall at the impact location according to an embodiment of the present invention.
Figure 2E:
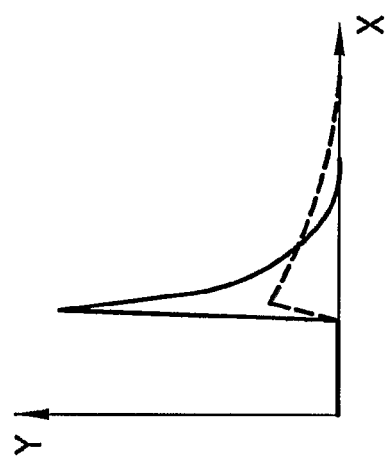
FIG. 2E is a graph of the number of photons, Y, that experience a first backscattering event, versus the projection distance, X along the inner wall-liquid interface for the, backscattered example illustrated in FIG. 2C.

A third reason for directing light beam (7) onto the bottle wall under an oblique angle is illustrated in FIGS. 2C, 2D, 2E, and 2F. FIG. 2C illustrates, as a dashed line (29A), the locations inside the liquid suspension (5) from where the first photons are backscattered, in this case when the incoming light beam (7) coincides with the normal to the glass wall of the bottle (1) at the primary beam impact point (9) and the secondary beam impact point (11) at the inner wall-liquid interface (3). Imaging device (12) and photodetector (13) in FIG. 1A would, in this case, receive backscattering photons that have their roots in first backscattered photons that are all located on the very same X-position along the bottle wall in FIG. 2C. FIG. 2E shows schematically the number of photons, Y, that experience a first backscattering event, versus the projection X along the liquid-wall interface for the situation as illustrated in FIG. 2C. The recorded light distribution of FIG. 2E shows a solid curve that corresponds to a high blood volume and a dashed curve that corresponds to a low blood volume.

Figure 2D:
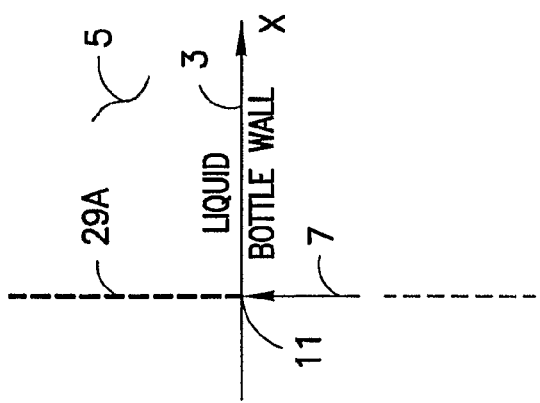
FIG. 2D illustrates, as a dashed line, locations inside a liquid blood culture where a first group of photons are backscattered, for the case where an incoming light beam deviates from the normal to the glass wall at the impact location by an angle $\Omega$ according to an embodiment of the present invention.
Figure 2F:
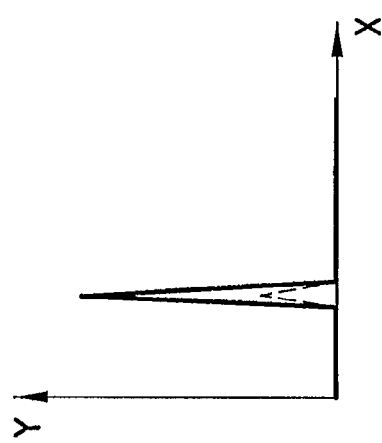
FIG. 2F is a graph of the number of photons, Y, that experience a first backscattering event, versus the projection distance, X along the inner wall-liquid interface for the backscattered example as illustrated in FIG. 2D.

In contrast to the case of normal incidence, FIG. 2D illustrates, the locations inside the liquid suspension (5) from where the first photons are backscattered as dashed line (29B). In this configuration the incoming light beam (7) deviates from the normal to the glass wall at the primary beam impact point (9) by an angle Θ. As one skilled in the art can appreciate, the light beam (7) arrives at the outer wall-air interface (2) at an angle Θ and is refracted in the bottle wall at a different angle in accordance with Snell's law for the refraction of light. Thus, the light beam (7) arrives at the inner wall-liquid interface (3) at an angle Ω, which is smaller than Θ, but dependent upon it. FIG. 1C illustrates the relationship between the angles Θ and Ω, the incoming light beam (7) and the normal to the bottle wall (10). Imaging device (12) and photodetector (13) in FIG. 1A receive backscattering photons that have their roots in first backscattered photons that are located on multiple X-positions along the bottle wall at the inner wall-liquid interface (3) as shown in FIG. 2D. FIG. 2F shows schematically the number of photons Y that experience a first backscattering event, versus the projection, X, along the inner wall-liquid interface (3) for the situation as illustrated in FIG. 2D. Again, the solid curve in FIG. 2F corresponds to a high blood volume, and the dashed curve corresponds to a low blood volume. For high blood volume, more scattering events take place per unit length. Consequently, a high backscattering intensity is observed near the secondary beam impact point (11) at the inner wall-liquid interface (3), but the backscattering intensity decays relatively quickly with increasing distance in X-direction from the secondary beam impact point (11) because of the higher scattering rate. For low blood volume, fewer scattering events take place per unit length. Consequently, a lower backscattering intensity is observed near the secondary beam impact point (11) at the inner wall-liquid interface (3), but more un-scattered photons are able to propagating deeper and to one side into the liquid suspension (5), and the backscattering intensity decays relatively slowly with increasing distance in the X-direction from the secondary beam impact point (11) at the inner wall-liquid interface (3). Therefore, the apparatus according to an embodiment of the present invention, as described above, that directs the light beam (7) onto the bottle (1) under oblique incidence, differentiates to a much higher degree of reliability between bottles (1) of low and high blood volumes.

Figure 3A:
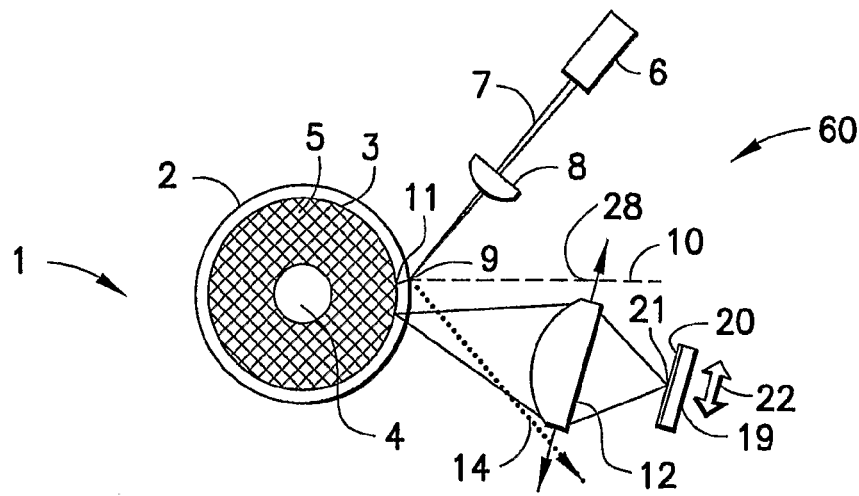
FIG. 3A illustrates schematically the optical arrangement in a second apparatus according to an embodiment of the present invention having a moving photodetector.

FIG. 3A illustrates schematically the optical arrangement in a second apparatus according to an embodiment of the present invention having a moving photodetector. The second partial apparatus (60) is similar to the first partial apparatus (50) depicted in FIG. 1A, with the exception that photodetector (13) in FIG. 1A is replaced with a simple photodetector (19) such as a photodiode. Simple photodetector (19) is shielded by means of an opaque plate (20) that has a narrow slit (21). By moving simple photodetector (19), along the direction of first double arrow (22), part of the asymmetric spatial backscatter light distribution (15) shown in FIG. 1B can be recorded along one axis. The same results can be achieved by letting photodetector (19) remain stationary in one position, and moving imaging device (12) instead along second double arrow 28.

Figure 3B:
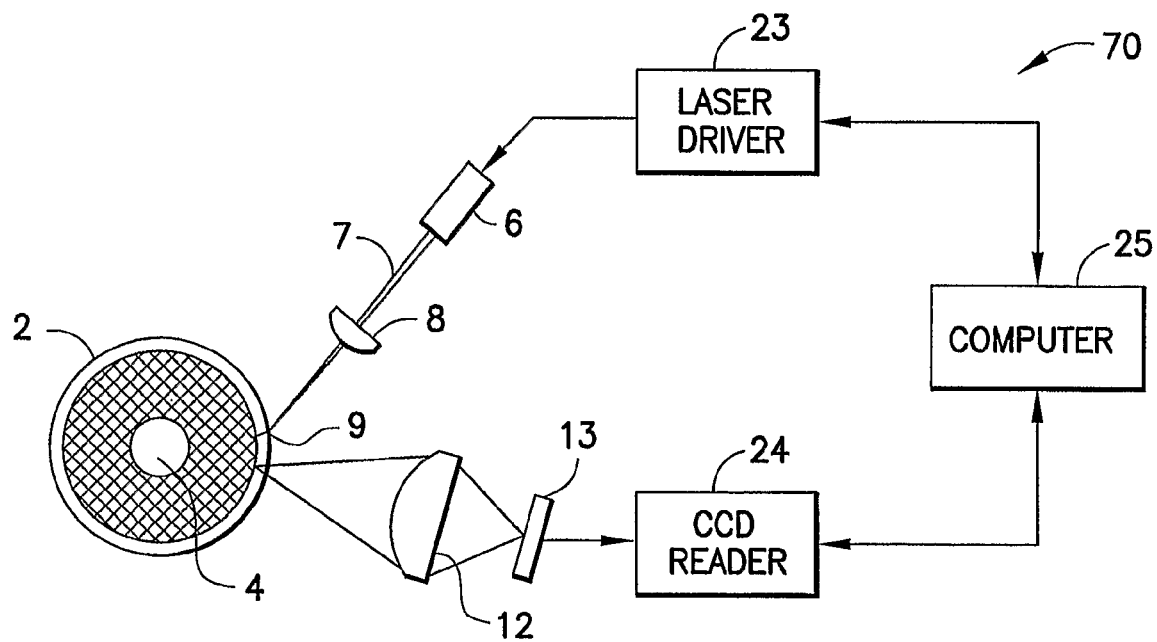
FIG. 3B illustrates schematically a complete blood culture optical measurement apparatus according to an embodiment of the present invention.

FIG. 3B illustrates schematically a complete blood culture optical measurement apparatus according to an embodiment of the present invention. In addition to the elements shown in FIG. 1A, optical source (6) is shown in an exemplary embodiment of the present invention as a laser connected with a laser driver power supply (laser driver) (23). Photodetector (13), in an exemplary embodiment of the present invention, is a CCD camera, connected to a dedicated CCD reader (24). Both devices, laser driver (23) and CCD reader (24) are connected to a computer (25) that controls operation of the apparatus (70), for recording data, performing data analysis and presenting the results of the measurements to the user.

Further, as one skilled in the art can appreciate, computer (25) can be connected to a network (LAN, WAN, wireless internet, or any other type of network) so that one or more users can use the apparatus (70) remotely, or receive data as a result of their own or other's manipulations of the apparatus (70).

In accordance with the embodiments of the present invention, a complete blood culture optical measurement apparatus (70) may comprise an optical source emitting light within the wavelength range of about 500 nm to 1500 nm. Preferably, the wavelength range is the range of about 600 nm to 1200 nm. A more specific embodiment of the present invention utilizes an optical source emitting light within the wavelength range of about 600 nm to 760 nm. Advantageous results have been obtained using an apparatus (70) according to an embodiment of the present invention with an optical source emitting light, within the wavelength range of about 640 nm to 720 nm. The optical source can be a laser, a light emitting diode, or any other optical source emitting light of sufficient optical power within the wavelength ranges given above. One exemplary embodiment of the present invention utilizes a semiconductor laser, emitting approximately 5 mW of power at a wavelength of about 640 nm.

According to another embodiment of the present invention, the complete blood culture optical measurement system (70) can utilize the second partial blood culture optical measurement apparatus (60) wherein a moving photodiode is used as the simple photodetector (19). The apparatus (60) still further comprises a periodic intensity-modulated light beam (7) and a synchronous detection device. One example of a synchronous detection device is a lock-in voltmeter. The lock-in voltmeter achieves robust measurement results since artifacts due to stray light, remaining room light, and the effect of the photodiode's dark current can be eliminated. The same is possible even for linear or 2D detector arrays.

EXAMPLE 1

Figure 4:
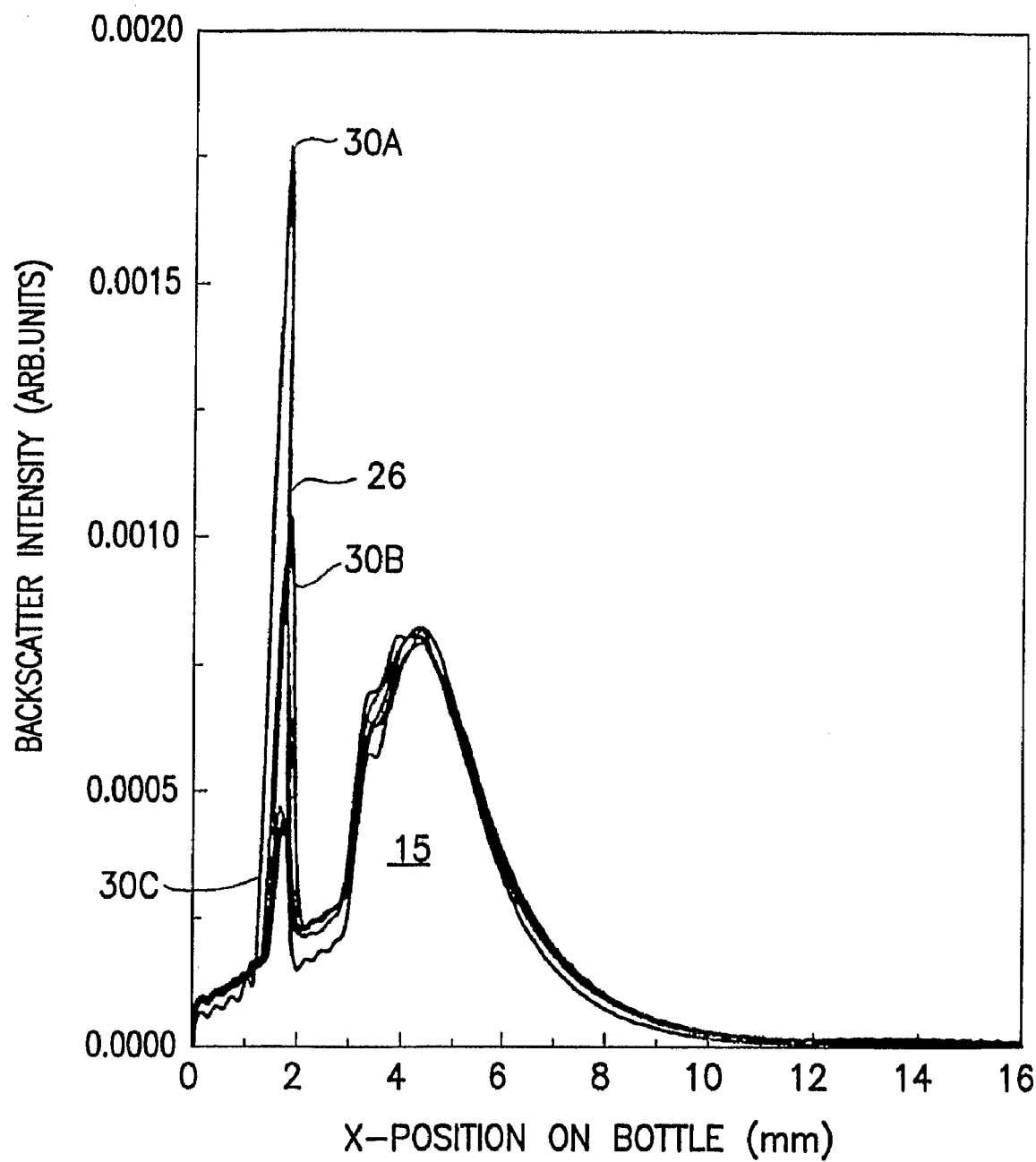
FIG. 4 is a graph that illustrates multiple recordings of the spatial distribution of back-scattered light on one blood culture bottle according to an embodiment of the present invention.

FIG. 4 illustrates multiple recordings of the spatial distribution of back-scattered light on one blood culture bottle that were obtained using the apparatus illustrated in FIG. 3A. Optical source (6) is a laser that emits a power of about 5 mW at a wavelength of about 633 μm. Light beam (7) deviates from a normal to the bottle wall by an angle of about 35 degrees. A PN photodiode was used as the simple photodetector (19), and a narrow slit (21) aperture was used. Light beam (7) was chopped using an optical chopper (not shown), and the signal from the simple photodetector (19) was detected and recorded using a model SR850 DSP Stanford Research Systems lock-in amplifier. A simple photodetector (19) was mounted on a motorized translation stage to record the asymmetric spatial backscatter light distribution (15) along an X-direction perpendicular to the blood culture bottle's symmetry axis, corresponding to a distance of 16 mm from the bottle wall. (All Examples below use this same apparatus.) Blood culture bottles used in the Examples set forth herein were cylindrical glass culture bottles available commercially as BACTEC® bottles filled with BACTEC® Standard/10 Aerobic/F blood culture medium) from Becton, Dickinson and Company (Franklin Lakes, N.J., USA). Data from some of the bottles used is reflected in multiple examples and figures.

To achieve the results illustrated in FIG. 4, 5 mL of fresh blood were added to an aerobic blood culture bottle, and multiple recordings were performed at different locations on the bottle over an extended period of time, at time equals 3, 8, 13, 25, 32 and 49 hours. As can be seen from the multiple plots in FIG. 4, the asymmetric spatial backscatter light distribution (15) is substantially stable over the time period of 49 hours. As is apparent from FIG. 4, no matter when the backscatter distribution is recorded during this time period of 49 hours, substantially identical plots are obtained. In contrast to the asymmetric spatial backscatter light distribution (15), however, the spike-like error signal (30) due to the backscatter phenomenon (26) shows a significant variation in its amplitude from one recording to the next (see, for example, the variation in amplitudes for 30A, 30B and 30C). As this spike-like error signal (30) is far enough to the left of the asymmetric spatial backscatter light distribution (15), however, such variations have no impact on the measurements on the asymmetric spatial backscatter light distribution (15).

Figure 5:
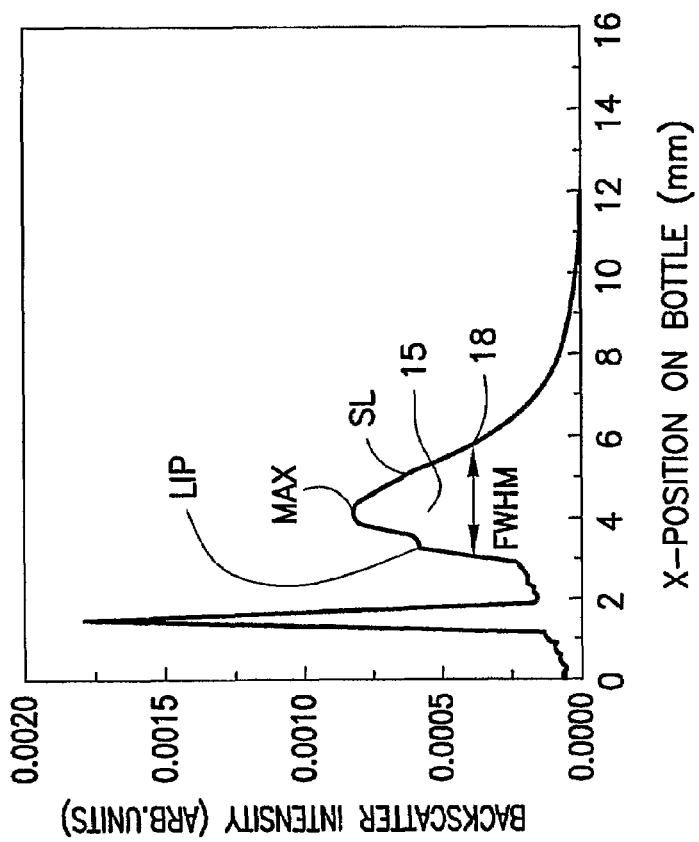
FIG. 5 is a graph that illustrates several distinct graphical features on a recorded spatial light distribution that are suitable for data analysis according to an embodiment of the present invention.

FIG. 5 shows one of the asymmetric spatial backscatter light distributions (15) from FIG. 4, and illustrates several distinct characteristic parameters that are used to differentiate between positive and negative blood culture bottles, and to determine the combination of the hematocrit and the blood volume. The term "LIP" in FIG. 5 refers to "light impact point" and indicates the backscattering intensity at a special position on the asymmetric spatial backscatter light distribution (15), the secondary beam impact point (11). The term "IALIP" stands for the back-scattering intensity at the light impact point. "FWHM" refers to "full-width-at-half-maximum" and "MAX" refers to the profile maximum. The term "IMAX" stands for the maximum back-scattering intensity measured on the spatial back-scattering distribution. "SL" refers to "slope". The slope of the asymmetric spatial backscatter light distribution (15) on the slowly decaying flank (18) is of interest, and the semi-logarithmic presentation of the data in FIG. 6 illustrates how the slope can be determined with high precision.

Additional analytical features that can be used in the method according to the embodiments of the present invention comprise parameters that are derived by analyzing the full spatial distribution of the asymmetric spatial backscattering distribution (15). Such features can include the number of pixels in a two-dimensional image of the asymmetric spatial backscattering distribution (15) having a pixel intensity that exceeds a given threshold, or the sum of all the pixel intensities in a two-dimensional image of the asymmetric spatial backscattering distribution (15), among others. Furthermore, additional "processed analytical features" of the asymmetric spatial backscattering distribution (15) can be generated by mathematical combinations of two or more of the analytical features. Examples of this will be discussed in greater detail below.

Figure 6:
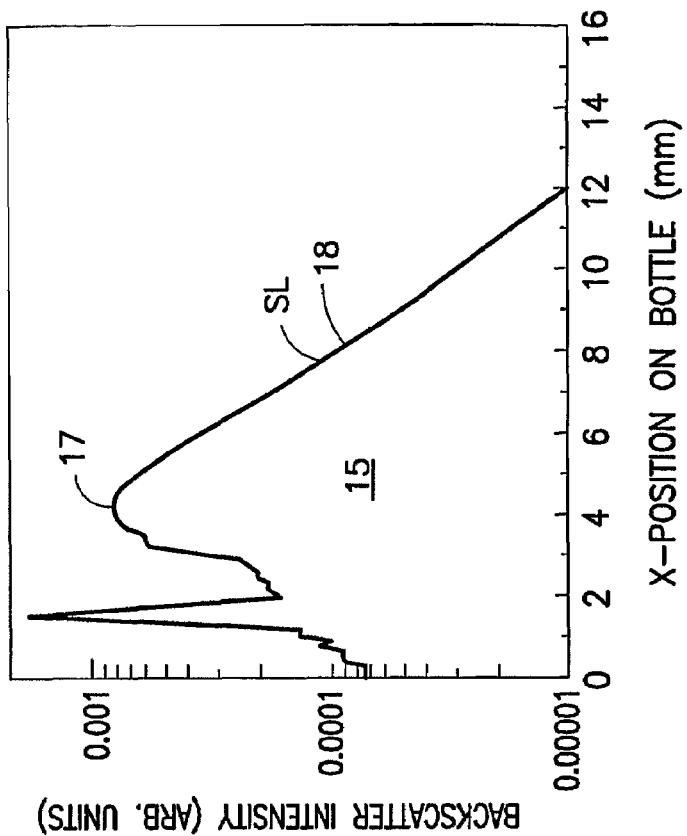
FIG. 6 is a graph that illustrates the same data as in FIG. 5, but in a semi-log representation.

The characteristic parameters shown in FIGS. 5 and 6 are dependent on the number of red blood cells in a culture bottle. This occurs because the higher the number of red blood cells, the shorter the distance between scattering events for the photons propagating within the liquid sample. More scattering events per unit length have an impact on the observed backscatter distribution. The number of red blood cells is determined by the combination of the blood fill volume and the hematocrit value. The characteristic parameters shown in FIGS. 5 and 6 are also dependent on whether a developed microorganism population is present or absent. In the presence of microorganisms, the hemoglobin within the red blood cells becomes "de-oxygenated" due to the metabolism of the microorganisms. At the wavelengths of the light beam typically used in the system, the absorption coefficient of hemoglobin changes substantially during de-oxygenation. Therefore, many more photons are absorbed when a culture bottle becomes positive (i.e., bacteria is present), which has an impact on the observed asymmetric spatial backscatter light distribution (15). The effects of the blood volume and the presence or absence of a developed microorganism population are illustrated in FIGS. 7A-9C.

EXAMPLE 2

Figure 7C:
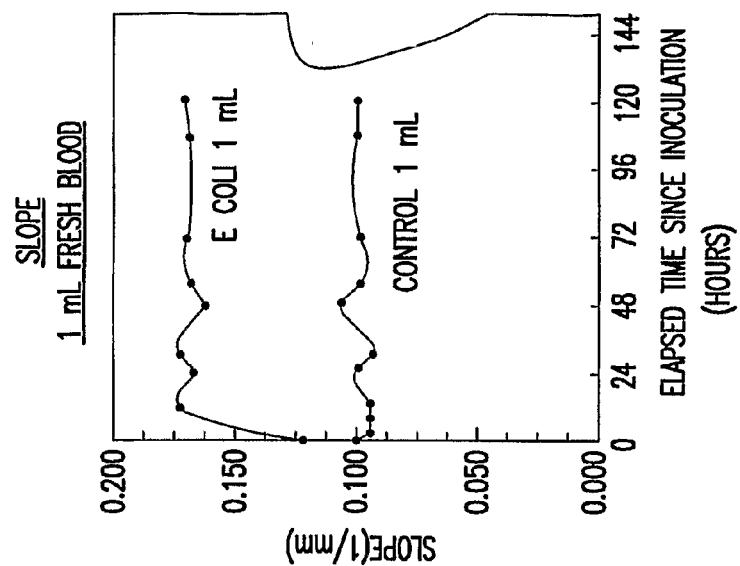
FIGS. 7A-7C are graphs that illustrate light-impact-point intensity versus time, measurement of the full-width-at-half-maximum of intensity versus time, and the slope of the intensity-versus-X-position graph versus time, respectively, for two blood culture bottles, a first blood culture bottle containing a 1 mL control sample of blood, and a second blood culture bottle containing 1 mL of blood with *E-coli*, for a period of approximately 144 hours.
Figure 7B:
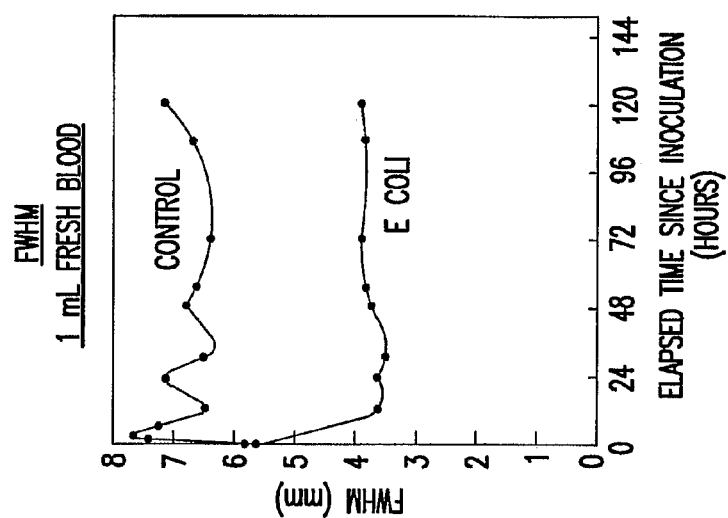
Figure 7A:
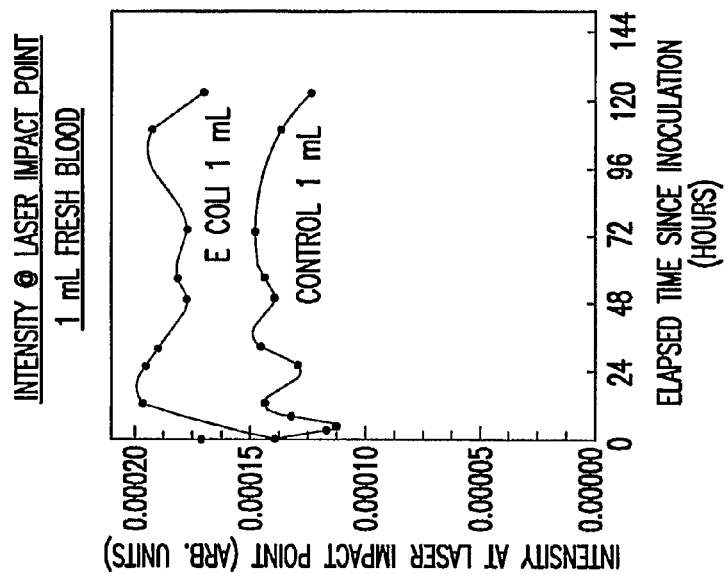

FIGS. 7A-7C illustrate graphs of light-impact-point intensity versus time, measurement of the full-width-at-half-maximum of intensity versus time, and the slope of the intensity-versus-X-position graph over time, respectively, for two blood culture bottles, a first blood culture bottle containing a 1 mL control sample of blood, and a second blood culture bottle containing 1 mL of blood with E-coli, for a period of approximately 144 hours.

EXAMPLE 3

Figure 8C:
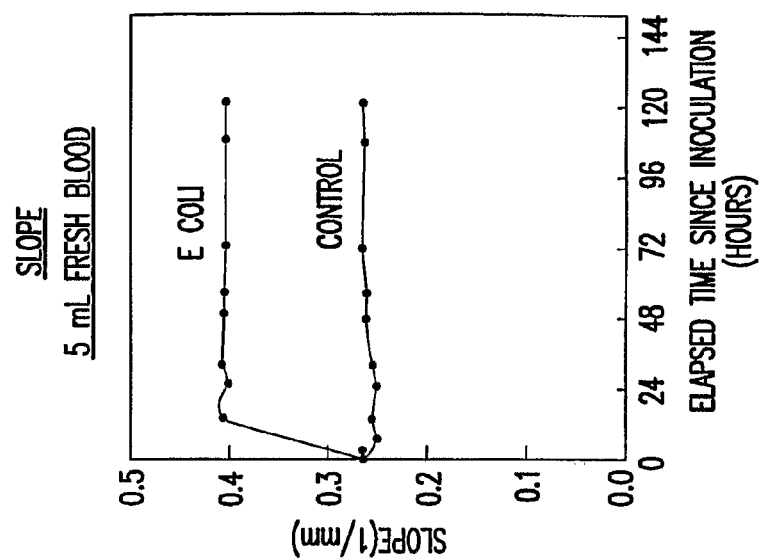
FIGS. 8A-8C are graphs that illustrate the same parameters of FIGS. 7A-7C, but for a first blood culture bottle containing 5 mL of blood and a second blood culture bottle containing 5 mL of blood with *E coli*.
Figure 8B:
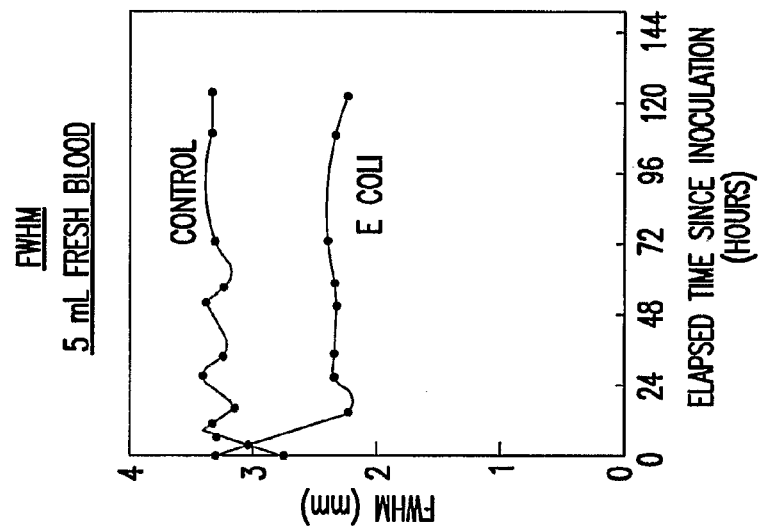
Figure 8A:
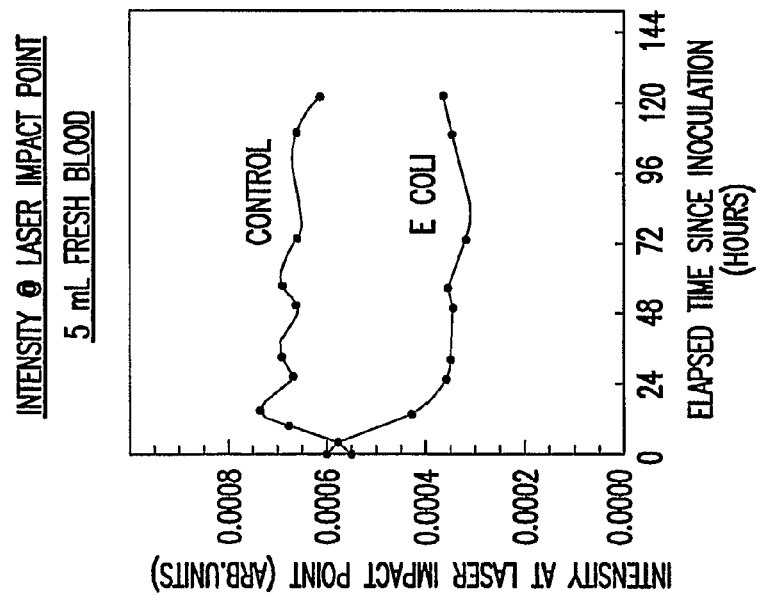

FIGS. 8A-8C illustrate similar graphs of the same parameters of FIGS. 7A-7C, but for a first blood culture bottle containing 5 mL of blood and a second blood culture bottle containing 5 mL of blood with E coli.

EXAMPLE 4

Figure 9C:
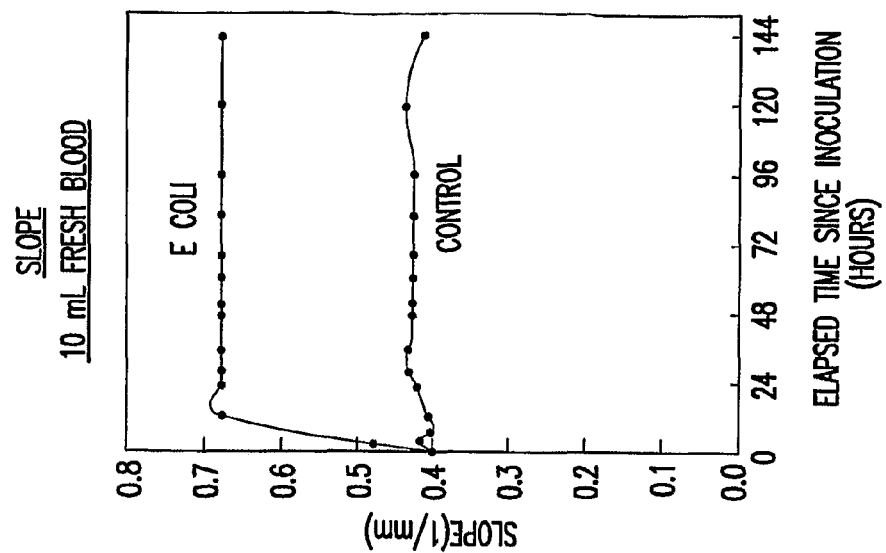
FIGS. 9A-9C are graphs that illustrate the same parameters of FIGS. 7A-7C, but for a first blood culture bottle containing 10 mL of blood and a second blood culture bottle containing 10 mL of blood with *E coli*.
Figure 9B:
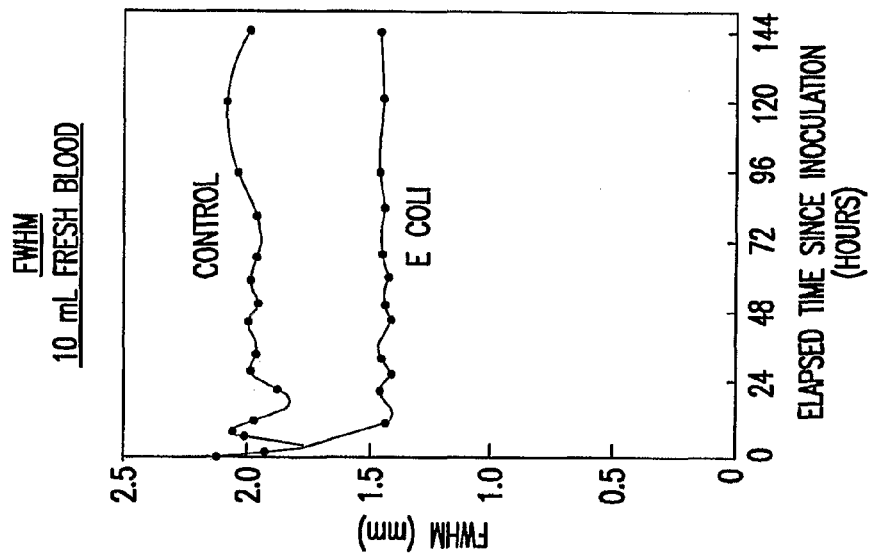
Figure 9A:
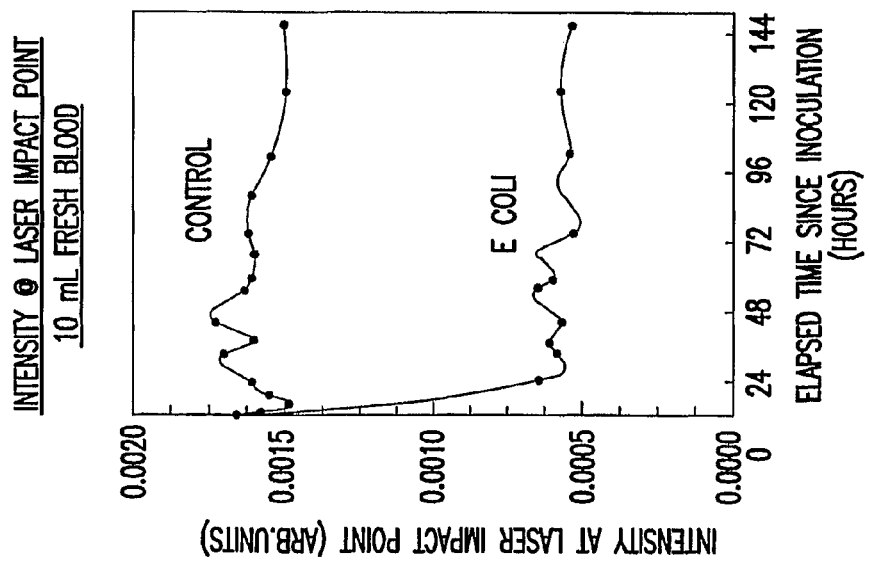

FIGS. 9A-9C illustrate similar graphs of the same parameters of FIGS. 7A-8C, but for a first blood culture bottle containing 10 mL of blood and a second blood culture bottle containing 10 mL of blood with E coli. As seen in FIGS. 7A-9C, the same dependencies exist for the blood culture bottles containing 5 and 10 mL as in the blood culture bottles containing only 1 mL, as discussed immediately above.

Figure 10:
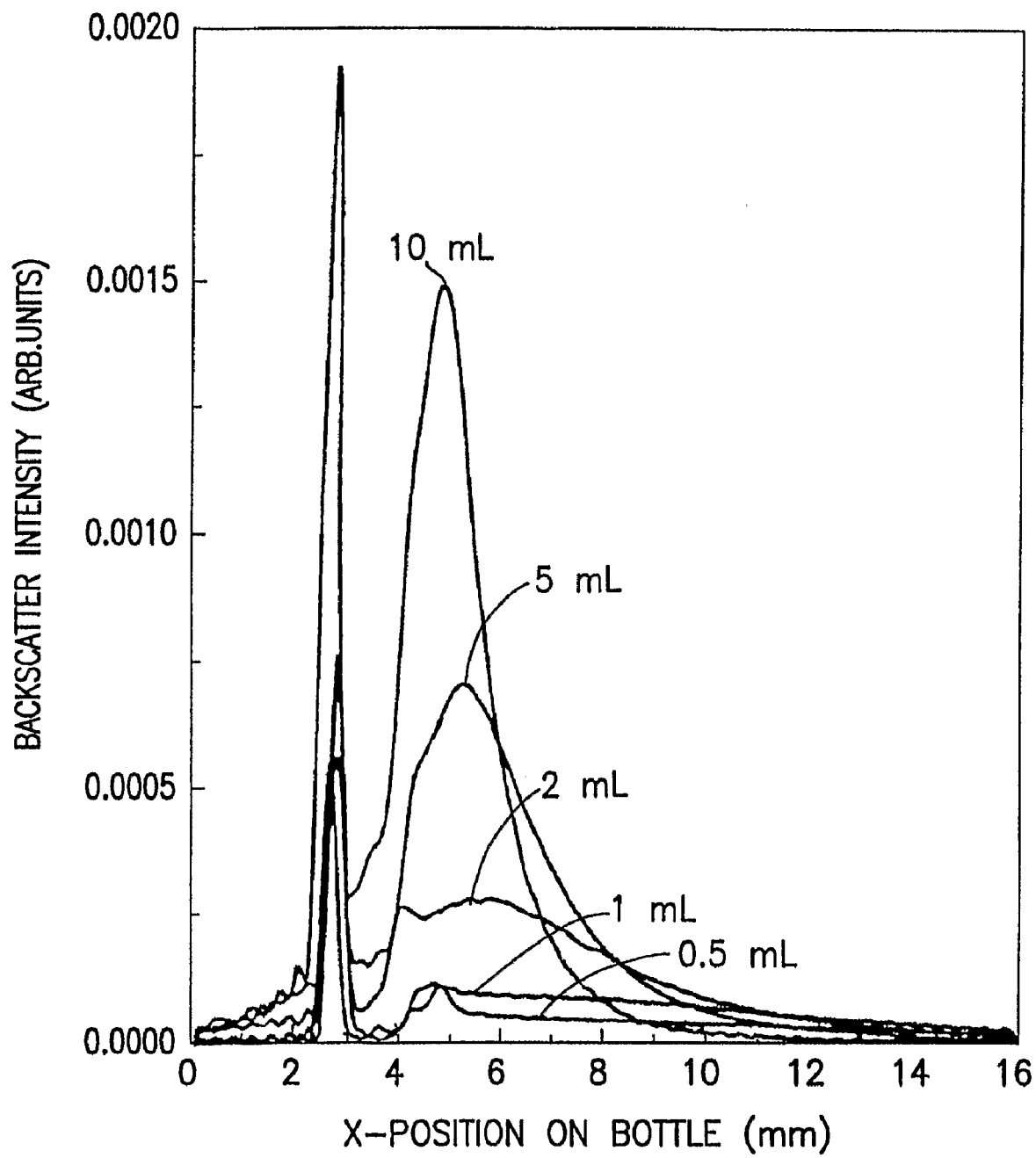
FIG. 10 is a graph that illustrates multiple recordings of the spatial distribution of backscattered light on blood culture bottles filled with varying amounts of blood between 0.5 mL and 10 mL.

FIG. 10 is a graph that illustrates multiple recordings of the spatial distribution of backscattered light on blood culture bottles filled with varying amounts of blood between 0.5 mL and 10 mL. FIG. 10 illustrates multiple recordings of the spatial distribution of back-scattered light on blood culture bottles filled with varying amounts of blood between 0.5 mL and 10 mL that were obtained using the apparatus of Example 1.

Figure 11:
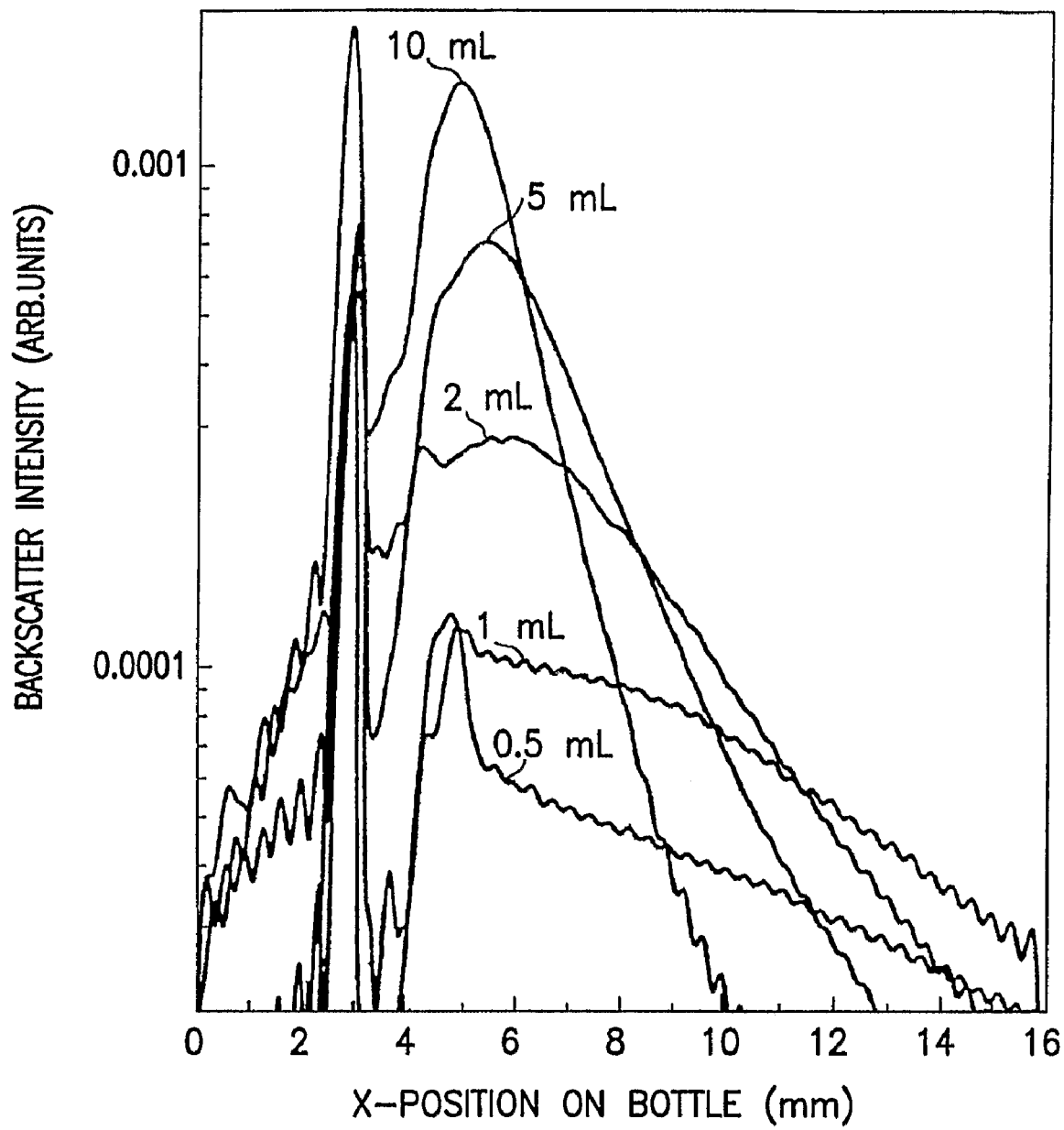
FIG. 11 is a graph that illustrates the same data as in FIG. 4, but in semi-log representation.

FIG. 11 shows the data of FIG. 10 in semi-logarithmic presentation. As can be seen, slowly decaying flank (18) from FIG. 1B takes the form of a straight line, which is advantageous for determining a slope value.

The present invention provides, in one aspect, for a method for determining the volume and hematocrit value of a blood sample using apparatus such as disclosed herein. In one embodiment, pre-recorded calibration values for extracted analytical features are obtained. Extracted analytical features of a sample are then obtained and compared with the calibration values to determine volume and hematocrit value for a sample. In the method according to some embodiments of the present invention, a light beam (7) is directed onto the outer air-wall interface (wall) (2) of a blood culture bottle (1) at a primary beam impact point (9) in such a way that the light beam (7) deviates from a normal (10) to the bottle wall (2) at the primary beam impact point (9) by an angle Θ between about zero and 90 degrees. If the angle Θ becomes very small, the generated asymmetric spatial backscatter distribution (15) of light becomes more and more symmetrical. A symmetrical spatial distribution also carries information about the status of the liquid suspension (5) and can be used according to an embodiment of the present invention. Better results can be achieved, however, with a larger angle Θ as described above. Therefore, the method according one particular exemplary embodiment employs an angle Θ between about 25 and 45 degrees. If the light beam (7) is output from a laser and is directed at a normal incidence onto the primary beam impact point (9) at the bottle wall (2), then the light beam (7) would be back-reflected into the laser (6).

As used previously herein, the term "FWHM" stands for "full-width-at-half-IMAX". Since, as shown in FIG. 2B, the asymmetric spatial distribution of back-scattered light extends in two dimensions, we can differentiate between an "FWHMX", measured along the X-axis, and an "FWHMY", measured along the Y-axis. The Y-axis is oriented along the bottle wall within a plane perpendicular to the bottle wall and comprises the position of IMAX, but extends perpendicular to the X-axis.

The term "FWHM*" stands for "full-width-at-half-IALIP". Similarly to that as described just above, "FWHMX*", can be measured along the X-axis, and "FWHMY*", can be measured along the Y-direction that is parallel to the Y-axis in a plane comprising the position of IALIP, with the Y-direction as described above.

As used previously herein, the term "SL" stands for "slope". The slope of the asymmetric spatial backscattering distribution (15) on the slowly decaying flank (18) is of interest, and the semi-logarithmic presentation of the data in FIG. 6 illustrates how the slope can be determined with high precision. As can be seen from the semi-logarithmic presentation in FIG. 7, the slowly decaying flank (18) exhibits an extended section that corresponds to a straight line that can be "fitted" with a straight line. For practical reasons, the slope is defined as the inverse of the distance along the X-axis of a recorded asymmetric spatial backscattering distribution (15) over which the intensity decreases by a given factor. Because the slope as defined above is measured along the X-axis, we use the term "SLX". For practical reasons, a value of 10 for SLX is preferred, but, as one skilled in the art can appreciate, any other definition of a slope can also be used without departing from the scope of the present invention.

Similar to the width, a slope is also defined as measured along the Y-axis. The slope term "SLY" (18A) is defined as the inverse of the distance along the Y-axis of the recorded asymmetric spatial backscattering distribution (15) over which the intensity decreases by a given factor. In one exemplary embodiment, a factor of 10 can be used, although, as stated above, with other definitions of the slope, other factors are equally viable.

Another measurement of slope is "SLY*" (18B) that is measured along a Y-direction parallel to the Y-axis in a plane comprising the position of IALIP. SLY* is defined as the inverse of the distance along the Y-direction of the recorded asymmetric spatial backscattering distribution (15) over which the intensity decreases by a given factor. In one exemplary embodiment, a factor of 10 can be used, although, as stated above, with other definitions of the slope, other factors are equally viable.

EXAMPLE 6

Figure 12:
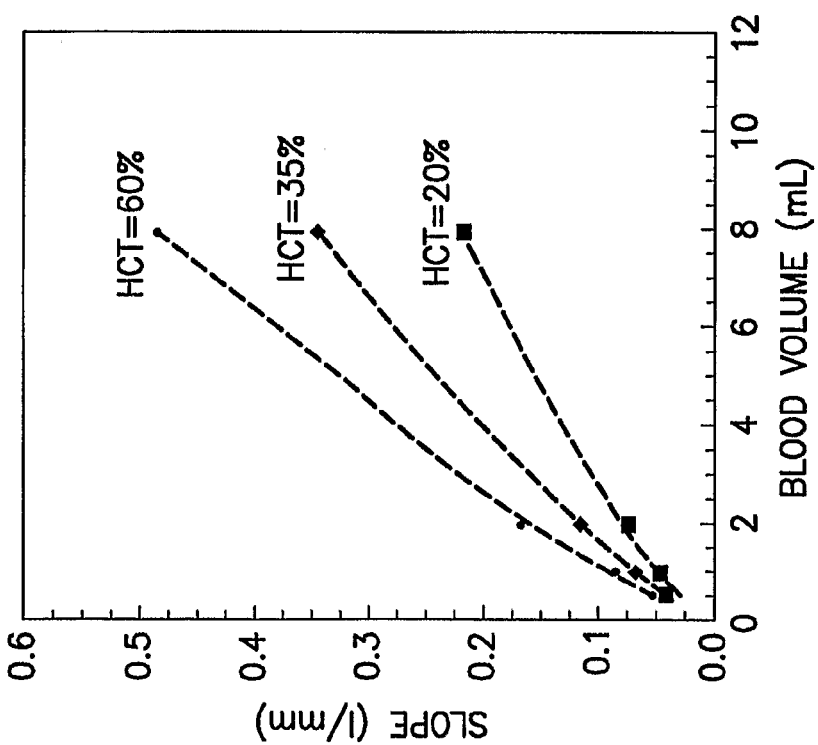
FIG. 12 is a graph that illustrates the slope versus blood volume as measured on twelve culture bottles filled with blood of three different hematocrit values.

FIG. 12 is a graph that illustrates the slope versus blood volume as measured on twelve culture bottles filled with blood of three different hematocrit values. Each data point represents a different culture bottle.

Figure 13:
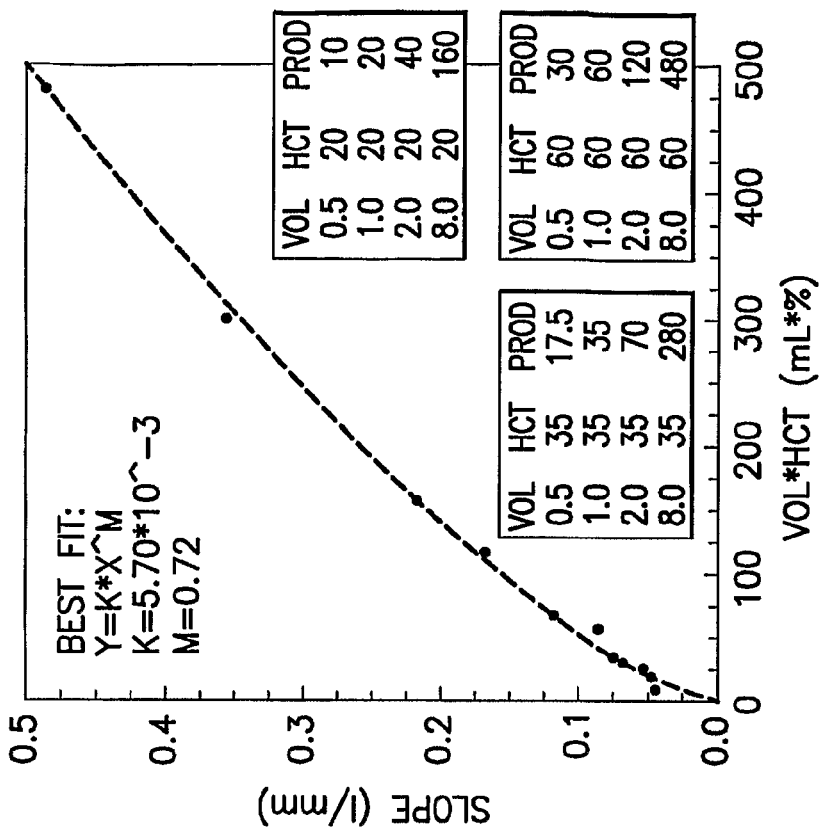
FIG. 13 is a graph that illustrates the slope versus the product of blood volume and hematocrit as measured on twelve culture bottles filled with blood of three different hematocrit values.

FIG. 13 is a graph that illustrates the slope versus the product of blood volume and hematocrit as measured on the twelve culture bottles. Each data point represents a different culture bottle. The insert tables indicate how the above-mentioned product has been generated in the twelve culture bottles. As can be seen from the graph illustrated in FIG. 13, the slope value can be expressed as a function of the above-mentioned blood volume and hematocrit product. The dashed line in FIG. 13 corresponds to the best fit $$Y = K * X^M \quad (1)$$

wherein Y=SL represents the slope, $K=5.70*10^{-3}$ is a first constant, X=VOL*HCT is the product of blood volume (VO)L and hematocrit value (HCT), and M=0.72 is a second constant. Based on the data shown in FIG. 13, the combination (here the product) of VOL and HCT can be determined by measuring the slope SL, and calculating the value of VOL*HCT according to the equation $$VOL * HCT = \left(\frac{SL}{K}\right)^{\frac{1}{M}}. \quad (2)$$

The so-called "blood background" artifact in a bacterial growth curve, which is a consequence of the metabolism of the dominating red blood cells, is proportional to the blood fill volume, VOL, and proportional to the hematocrit value, HCT. In other words, the blood background artifact is proportional to the product VOL*HCT that correlates to the number of red blood cells within a given blood culture bottle. The approach according to equation (2) for determining the product VOL*HCT is, therefore, a very useful procedure towards the design of optimized detection algorithms, as discussed above. If the product is high, a large blood background has to be expected, and the detection algorithm has to be robust. If the product is low, a small blood background can be expected, and the detection algorithm can be subtler. The algorithms, once determined according to the methods described herein, can then be used to ascertain the blood volume or hematocrit value for a given sample.

Figure 14:
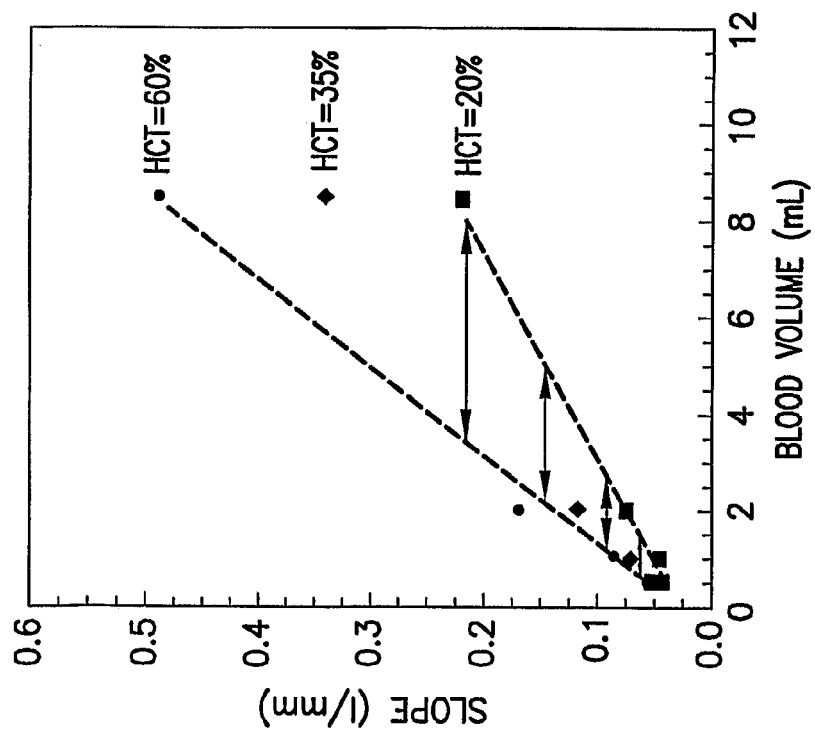
FIG. 14 is a graph that illustrates the data of FIG. 10, but with added double-arrows indicating the range of uncertainty in determining the fill volume alone.

As previously discussed, the volume of a blood sample filled into a culture bottle should be reasonably high, preferably around 10 mL. The need for employing a large volume of blood in culture bottles arises from the fact that, depending on the microorganism species, the number of cell forming units per mL of patient blood may be very low. In practice, and depending on the status of the patient, smaller than optimum amounts of blood are frequently used, which may have a negative impact on the reliability of such tests. In this context, a procedure for determining the actual fill volume of patient blood in every bottle loaded into an instrument would without doubt be of great advantage. If the slope SL is determined according to an embodiment of the present invention, the blood volume itself cannot be determined precisely. This is illustrated in FIG. 14, which shows in the form of double-arrows the possible volume range for a given slope value. As FIG. 14 illustrates, however, the length of the double arrows becomes shorter and shorter the smaller the blood fill volume. Therefore, the uncertainty in determining the blood fill volume itself becomes small within the low-volume range. Therefore, the method according to an embodiment of the present invention is suitable to identify truly "under-filled" blood culture bottles, i.e. bottles having received less than 1 mL of blood sample. It is worthwhile mentioning that at the high-volume end of the scale there is no critical need for knowing the fill volume precisely, since the probability of the blood sample containing at least one microorganism is relatively high. At the low-volume end, there is a likelihood that the one small blood volume selected may not contain an organism, which would result in a false-negative culture.

EXAMPLE 7

Figure 15:
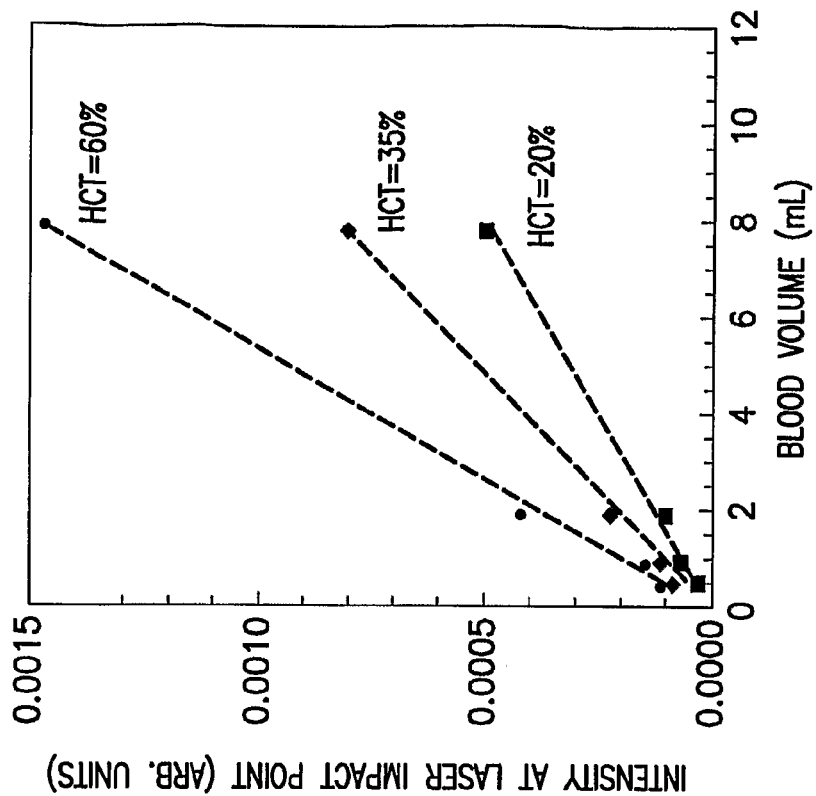
FIG. 15 is a graph that illustrates the backscattering intensity measured for the laser impact point versus blood volume as determined on twelve culture bottles filled with blood of three different hematocrit values.

FIG. 15 is a graph that illustrates the backscattering intensity measured for the laser impact point versus blood volume as determined on twelve culture bottles filled with blood of different hematocrit values. FIG. 15 shows the backscattering intensity, IALIP, measured for the laser impact point versus blood volume. Each data point represents a different culture bottle.

Figure 16:
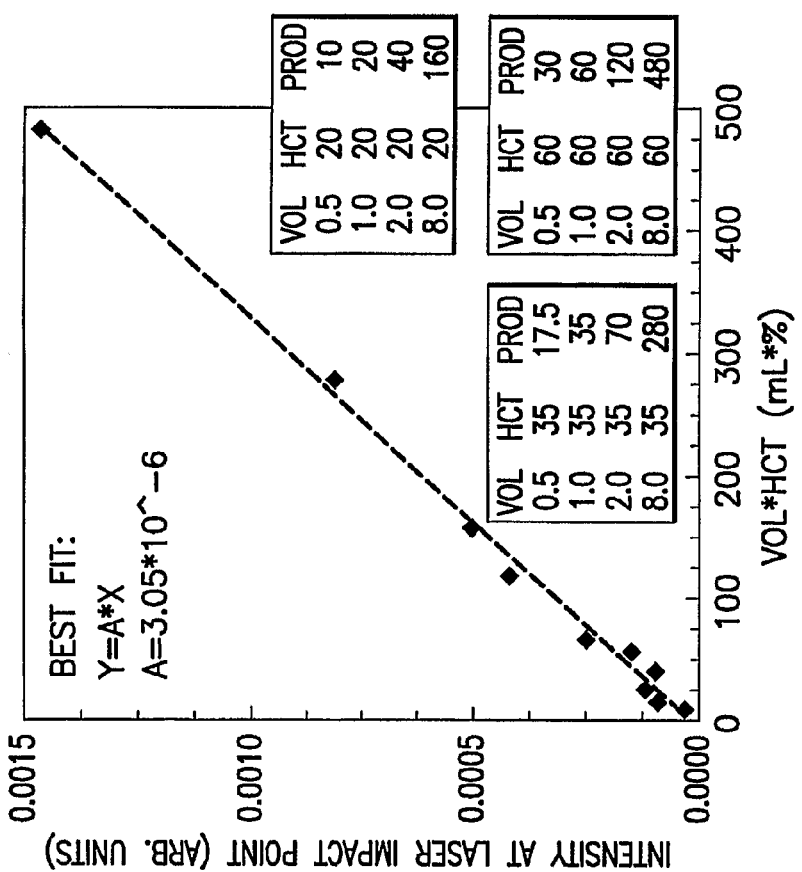
FIG. 16 is a graph that illustrates the backscattering intensity measured at the laser impact point versus the product of blood volume and hematocrit as measured on twelve culture bottles filled with blood of three different hematocrit values.

FIG. 16 is a graph that illustrates the backscattering intensity measured at the laser impact point versus the product of blood volume and hematocrit as measured on the twelve culture bottles. Each data point represents a different culture bottle. The insert tables indicate how the above-mentioned blood volume and hematocrit product has been generated in the twelve culture bottles. Because of the use of a laser, FIG. 16 and others include the wording "Intensity at Laser Inpact Point" instead of "Intensity at Light Impact Point". The dashed line in FIG. 16 corresponds to the best fit $$Y=A*X \tag{3}$$

wherein Y=IALIP represents the intensity at the laser impact point, $A=3.05*10^{-6}$ is a constant, and X=VOL*HCT is the product of blood volume VOL and hematocrit value HCT. It should be noted that the value of constant A depends on the exact details of the apparatus used. Based on the data shown in FIG. 16, the combination (here the product) of VOL and HCT can be determined according to an embodiment of the present invention by measuring the intensity IALIP, and calculating the value of VOL*HCT according to the equation $$VOL*HCT = \frac{IALIP}{A}. \tag{4}$$

Similar considerations in regard to the determination of the blood volume itself apply as discussed in connection with FIG. 14.

EXAMPLE 8

Figure 17:
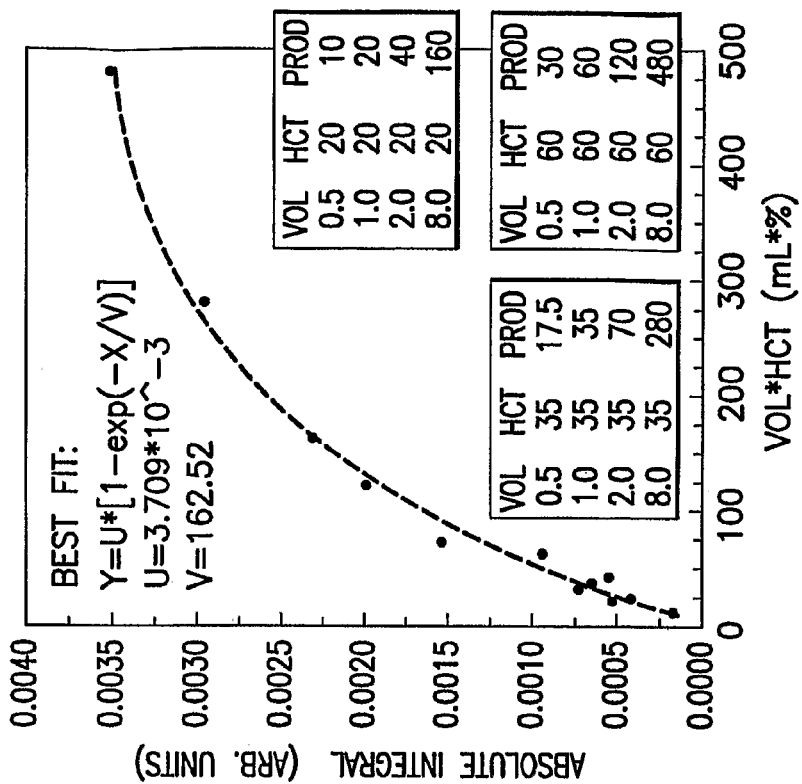
FIG. 17 is a graph that illustrates the value of integrals over recordings of the spatial distribution of backscattered light as shown in FIG. 4 on twelve blood culture bottles filled with varying amounts of blood.

FIG. 17 is a graph that illustrates the value of integrals over recordings of the spatial distribution of backscattered light as shown in FIG. 4 on twelve blood culture bottles filled with varying amounts of blood. Integration started at the X-position of about 3.5 mm to exclude the highly variable scattering peaks near the X-position of about 2.8 mm originating at the air-glass interface. The integrals are plotted versus the product VOL*HCT as measured on culture bottles filled with blood of three different hematocrit values. Each data point represents a different culture bottle. The insert tables indicate how the product has been generated. The dashed line in FIG. 17 corresponds to the best fit $$Y=U*[1-\exp(-X/V)] \tag{5}$$

wherein Y=INTEG represents the integral value, $U=3.709*10^{-3}$ is a first constant, X=VOL*HCT is the product of blood volume VOL and hematocrit value HCT, and V=162.52 is a second constant. Also, the values of the constants U and V depend on the exact details of the apparatus used. Based on the data shown in FIG. 19, the combination (here the product) of VOL and HCT can be determined according to an embodiment of the present invention by measuring the integral INTEG, and calculating the value of VOL*HCT according to the equation $$VOL*HCT = -V*\ln\left[1 - \frac{INTEG}{U}\right] \tag{6}$$

Figure 18:
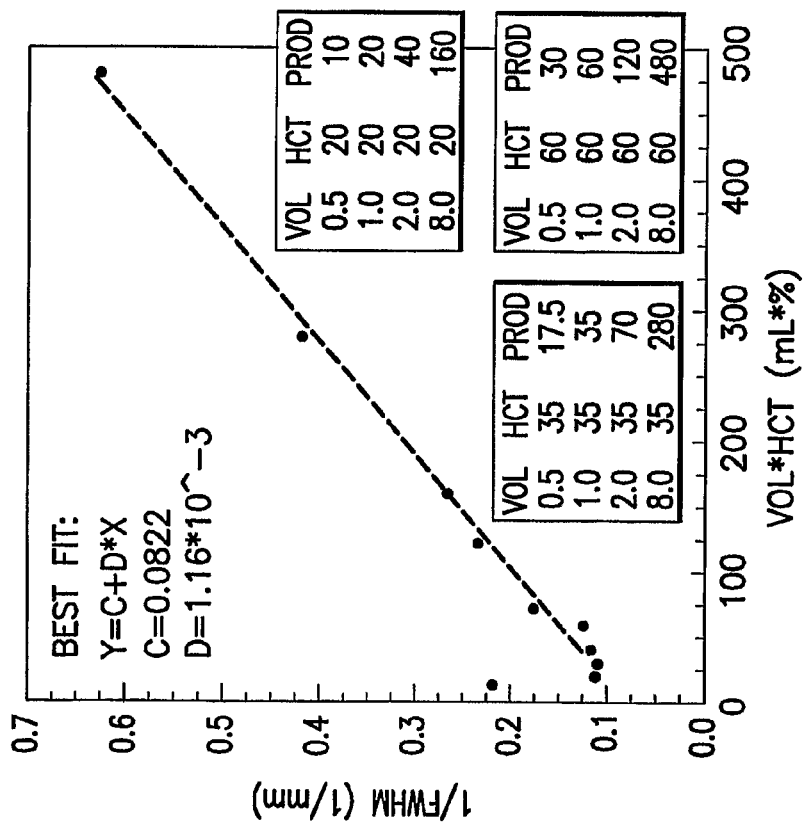
FIG. 18 is a graph that illustrates the inverse of the full-width-at-half-maximum ("1/FWHM") from recordings of the spatial distribution of backscattered light on twelve blood culture bottles versus the product of blood volume and hematocrit.

FIG. 18 is a graph that illustrates the inverse of the full-width-at-half-maximum ("1/FWHM") from recordings of the spatial distribution of backscattered light on the twelve blood culture bottles versus the product of blood volume and hematocrit, (VOL*HCT). Each data point represents a different culture bottle. The insert tables indicate how the product has been generated. The dashed line in FIG. 20 corresponds to the best fit $$Y=C+D*X \tag{7}$$

wherein Y=1/FWHM represents the inverse of the full-width-at-half-maximum, C 0.0822 is a first constant, X=VOL*HCT is the product of blood volume VOL and hematocrit value HCT, and $D=1.16*10^{-3}$ is a second constant. Based on the data shown in FIG. 20, the combination (here the product) of VOL and HCT can be determined according to an embodiment of the present invention by measuring the slope SL, and calculating the value of VOL*HCT according to the equation $$VOL*HCT = \frac{(1/FWHM) - C}{D} \tag{8}$$

Figure 19:
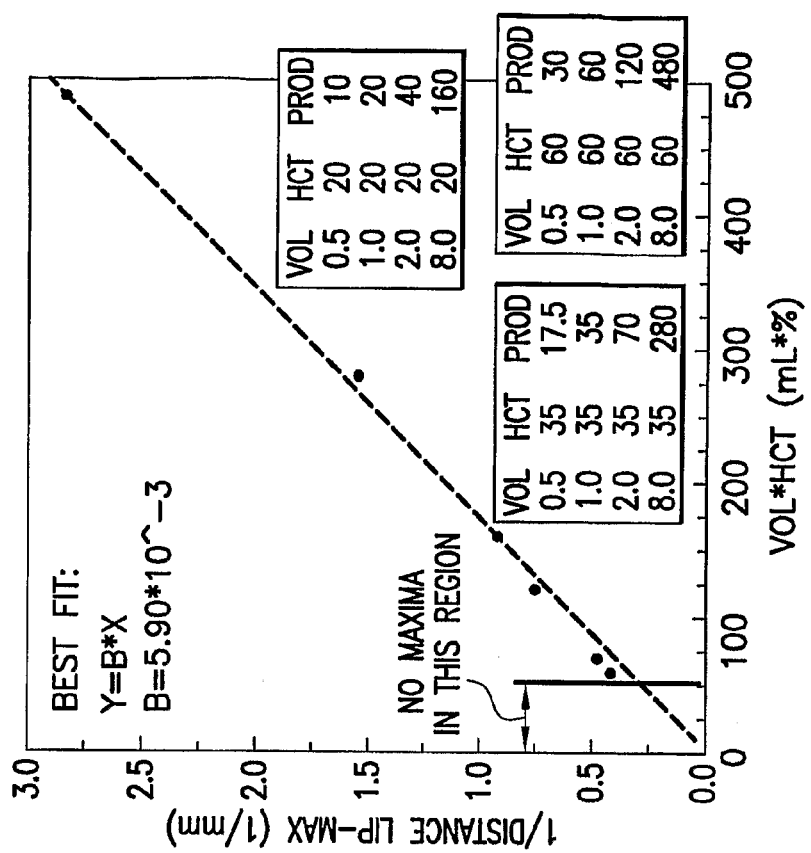
FIG. 19 is a graph that illustrates the inverse of the distance along the X-axis between the laser impact point, LIP, shown in FIG. 42, and the maximum, MAX, from recordings of the spatial distribution of backscattered light on blood culture bottles versus the product of blood volume and hematocrit.

FIG. 19 is a graph that illustrates the inverse of the distance along the X-axis between the laser impact point, LIP, shown in FIG. 12, and the maximum, MAX, from recordings of the spatial distribution of backscattered light on the blood culture bottles versus the product of blood volume and hematocrit, (VOL*HCT). Each data point represents a different culture bottle. The dashed line in FIG. 19 corresponds to the best fit $$Y=B*X \tag{9}$$

wherein Y=1/DIST represents the inverse of the distance along the X-axis between the laser impact point, LIP, and the maximum, MAX, shown in FIG. 12, $B=5.90*10^{-3}$ is a constant, and X=VOL*HCT is the product of blood volume VOL and hematocrit value HCT. Based on the data shown in FIG. 19, the combination (here the product) of VOL and HCT can be determined according to an embodiment of the present invention by measuring the inverse distance 1/DIST, and calculating the value of VOL*HCT according to the equation $$VOL*HCT = \frac{(1/DIST)}{B} \tag{10}$$

As has been shown above, the method according to an embodiment of the present invention can be used to determine the combination of the volume and the hematocrit value of a blood sample filled into a culture bottle by extracting the analytical features SL, IALIP, INTEG, (1/FWHM), or (1/DIST) of the asymmetrical spatial backscatter light distribution (15), and comparing said extracted analytical features with pre-recorded values for such features. In all the exemplary embodiments of the present invention discussed above, the extracted features were all recorded along the X-axis. Similar analytical features can be defined and recorded along the Y-axis. Moreover, analytical features in the method according to an embodiment of the present invention can also comprise parameters that are derived by analyzing the full spatial distribution of backscattered light. Such features can include the number of pixels in a two-dimensional image of said asymmetrical light distribution having a pixel intensity that exceeds a given threshold, or the sum of all pixel intensities in a two-dimensional image of said asymmetrical light distribution, among others.

Additional processed analytical features of the asymmetrical spatial backscatter light distribution (15) can be generated by way of mathematical combinations of two or more analytical features. Mathematical combinations that can be used include, but are not limited to, operations such as sums, differences, products, ratios, or powers of, among others.

Another example for generating a processed analytical feature is to determine values for the product PROD=VOL*HCT by using all of the above-discussed steps to determine products individually, such as $PROD_{SL}$, $PROD_{IALIP}$, $PROD_{INTEG}$, $PROD_{FWHM}$, and $PROD_{DIST}$, and then combine the individual results into an average product $PROD_{AV}$, according to the equation:

$$PROD_{AV} = \frac{PROD_{SL} + PROD_{IALIP} + PROD_{INTEG} + PROD_{FWHM} + PROD_{DIST}}{5} \quad (11)$$

The procedure according to equation (11) is robust and produces a highly reliable value $PROD_{AV}$ for said product.

In addition to the significance of obtaining a sufficiently large blood volume as explained above, it is also important to determine the status of the blood culture within a sealable container, such as a blood culture bottle, quickly since it is usually desirable for the status to be negative (i.e., that the number of microorganisms that might be present is still very low).

The status of a blood culture within a culture bottle can be checked according to an embodiment of the present invention for rapidly differentiating between positive and negative blood culture bottles. In this embodiment, a light beam (7) is directed onto the outer air-wall interface (wall) (2) of a blood culture bottle (1) at a primary beam impact point (9) in such a way that the light beam (7) deviates from a normal (10) to the bottle wall (2) at the primary beam impact point (9) by an angle Θ between about zero and 90 degrees. If the angle Θ becomes very small, the generated asymmetric spatial backscatter distribution (15) of light becomes more and more symmetrical. A symmetrical spatial distribution also carries information about the status of the liquid suspension (5) and can be used in the method according to the embodiments of the present invention. Better results can be achieved, however, with a larger angle Θ as described above. Therefore, the method according one particular exemplary embodiment employs an angle Θ between about 25 and 45 degrees. If the light beam (7) is output from a laser and is directed at a normal incidence onto the primary beam impact point (9) at the bottle wall (2), then the light beam (7) would be back-reflected into the laser (6).

EXAMPLE 9

Figure 20:
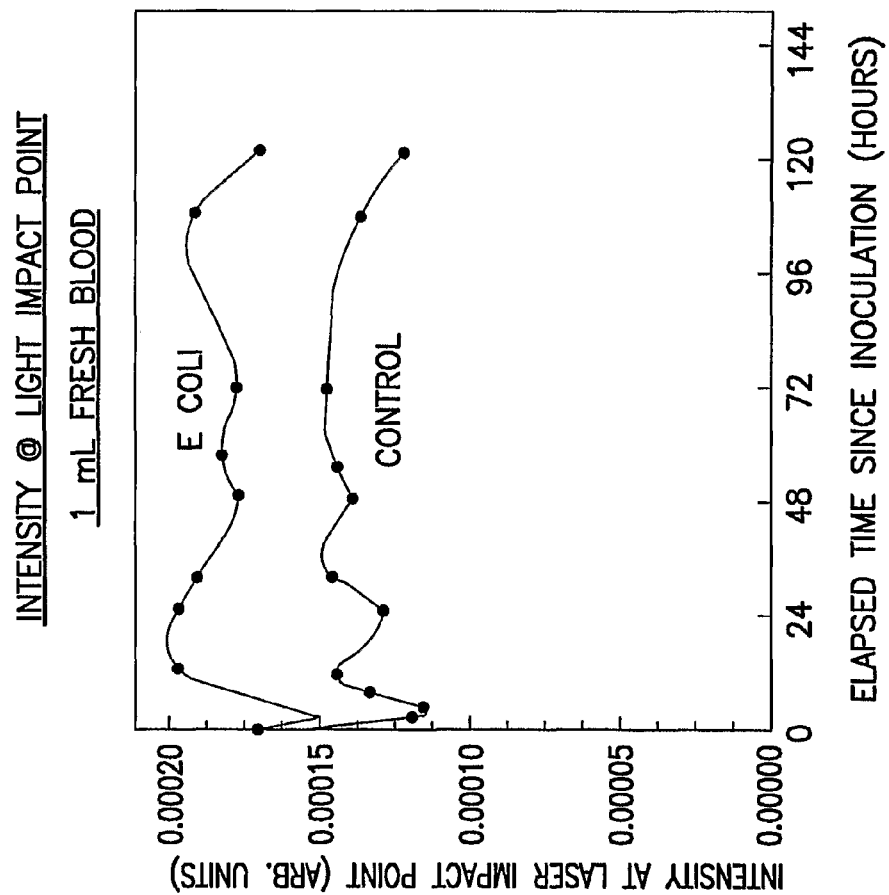
FIG. 20 is a graph that illustrates the light-impact-point intensity versus time for a first blood culture bottle containing a 1 mL control sample of fresh blood and a second blood culture bottle containing a 1 mL sample of blood and developed $E\ coli$ culture over a time period of approximately 5 days.

FIG. 20 is a graph that illustrates the light-impact-point intensity versus time for a first blood culture bottle containing a 1 mL control sample of fresh blood and a second blood culture bottle containing a 1 mL sample of blood and developed E coli culture over a time period of approximately 5 days.

The first measurement in FIG. 20 was performed immediately after inoculating one of the bottles with approximately 20 microorganisms of E coli. Thus, at time zero the E coli data is close to the data of a typical control bottle without organisms. The E coli bottle was then incubated for approximately 12 hours, which resulted in the development of a fully positive culture bottle. Two more measurements were performed on the control bottle while the E coli bottle was in the incubator. Both bottles were kept at room temperature after 12 hours. The two plots in FIG. 20 show that the analytical feature IALIP exhibits a substantial difference between the control bottle and the E coli bottle over the monitoring period of approximately 5 days. The additional measurements described below were performed under very similar conditions. In all cases, the measurements were performed along the X-axis; therefore the term "FWHMX" was shortened to just "FWHM". The same shortening has been applied to all other terms.

Figure 21:
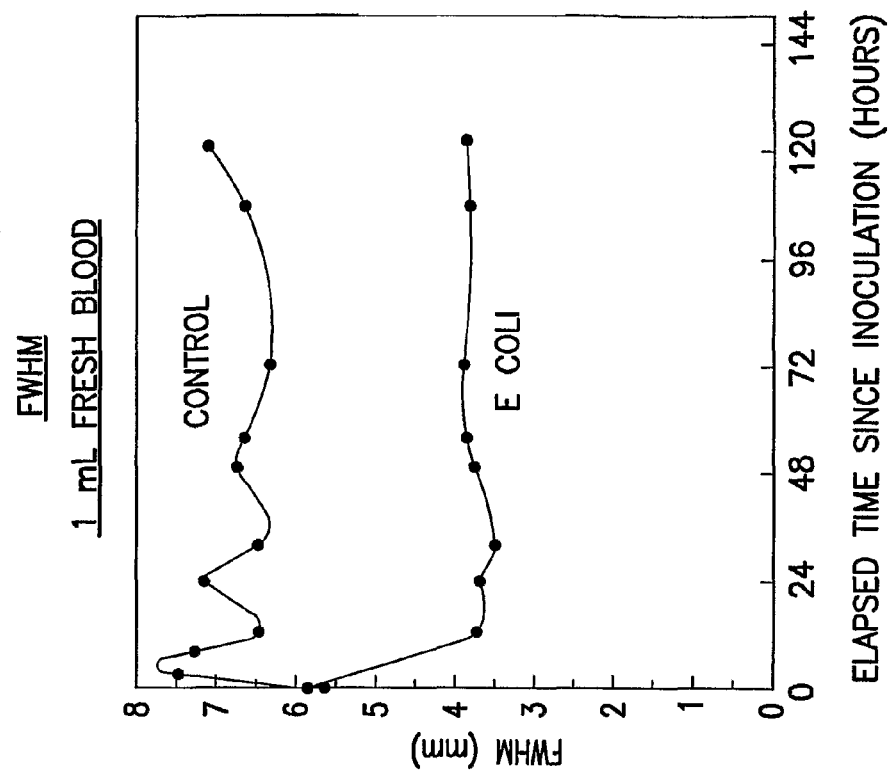
FIG. 21 is a graph that illustrates the full-width-at-half-maximum (FWHM) of the spatial distribution of backscattered light versus time for a first blood culture bottle containing a 1 mL control sample of fresh blood and a second blood culture bottle containing a 1 mL sample of blood and developed $E\ coli$ culture over a time period of approximately 5 days.

FIG. 21 is a graph that illustrates the full-width-at-half-maximum (FWHM) of the spatial distribution of backscattered light versus time for a first blood culture bottle containing a 1 mL control sample of fresh blood and a second blood culture bottle containing a 1 mL sample of blood and developed E coli culture over a time period of approximately 5 days. There is again a substantial difference in FWHM over the entire monitoring period of approximately 5 days. FIGS. 22 through 28 illustrate that there is a substantial difference in the analytic features measured between the control and positive bottles (2).

Figure 23:
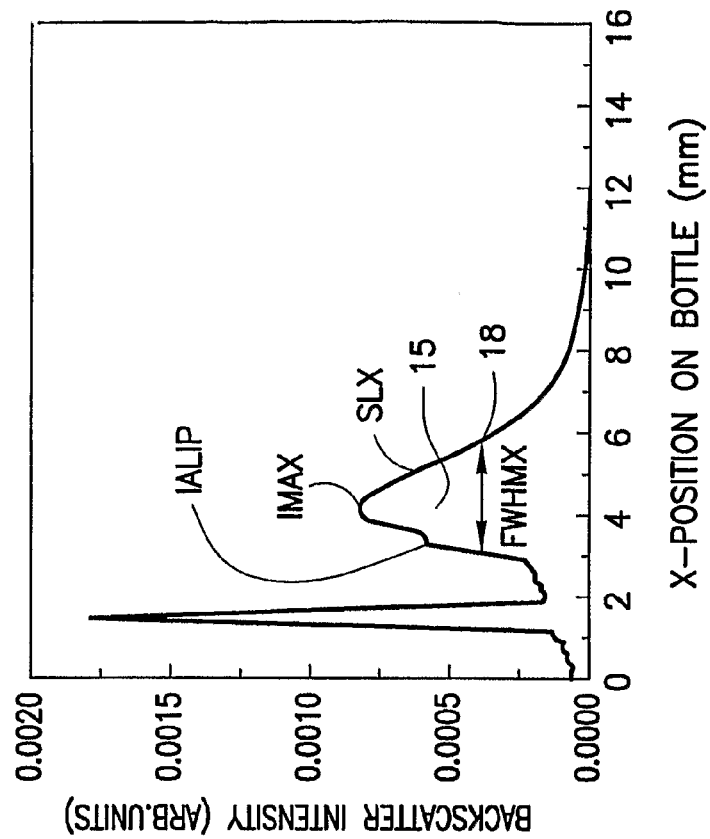
FIG. 23 is a graph that illustrates several distinct graphical features on a recorded spatial light distribution that are suitable for data analysis according to an embodiment of the present invention.
Figure 22:
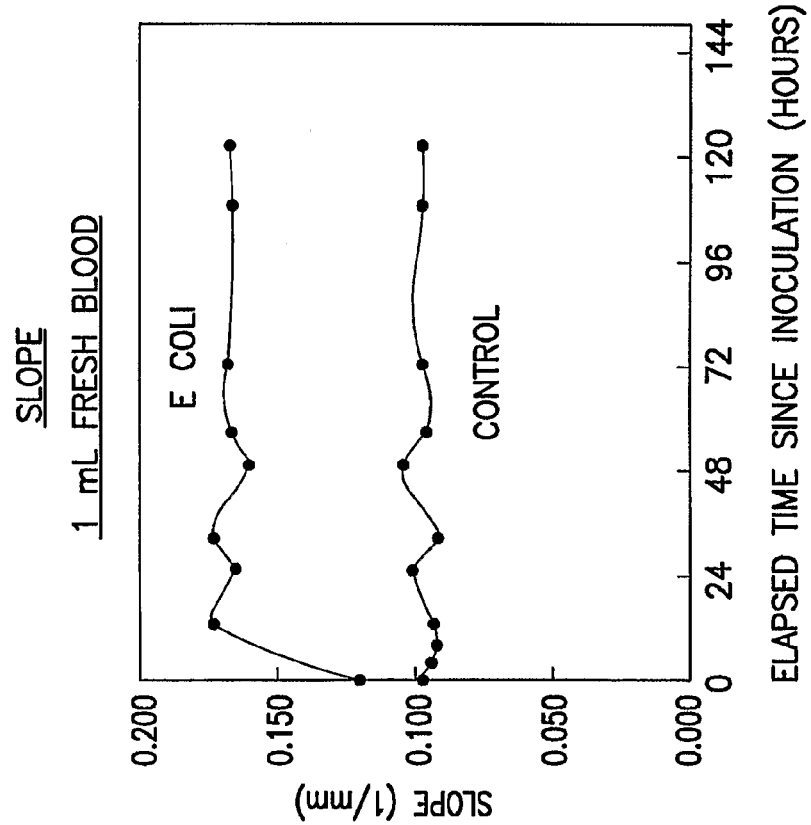
FIG. 22 is a graph that illustrates the slope of the spatial distribution of backscattered light versus time graph over time for a first blood culture bottle containing a control sample of 1 mL of fresh blood and a second blood culture bottle containing a 1 mL sample of blood and developed $E\ coli$ culture over a time period of approximately 5 days.
Figure 24:
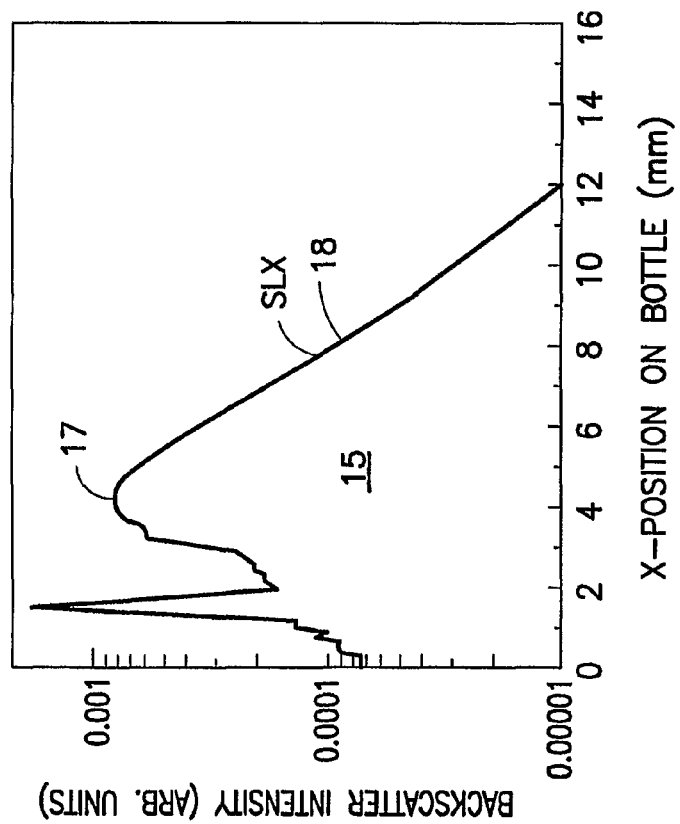
FIG. 24 is a graph that illustrates the same data as in FIG. 23, but in semi-log representation.

FIG. 22 is a graph that illustrates the slope of the spatial distribution of backscattered light versus time graph over time according to FIGS. 23 and 24 for a first blood culture bottle containing a control sample of 1 mL of fresh blood and a second blood culture bottle containing a 1 mL sample of blood and developed E coli culture over a time period of approximately 5 days.

EXAMPLE 10

Figure 25:
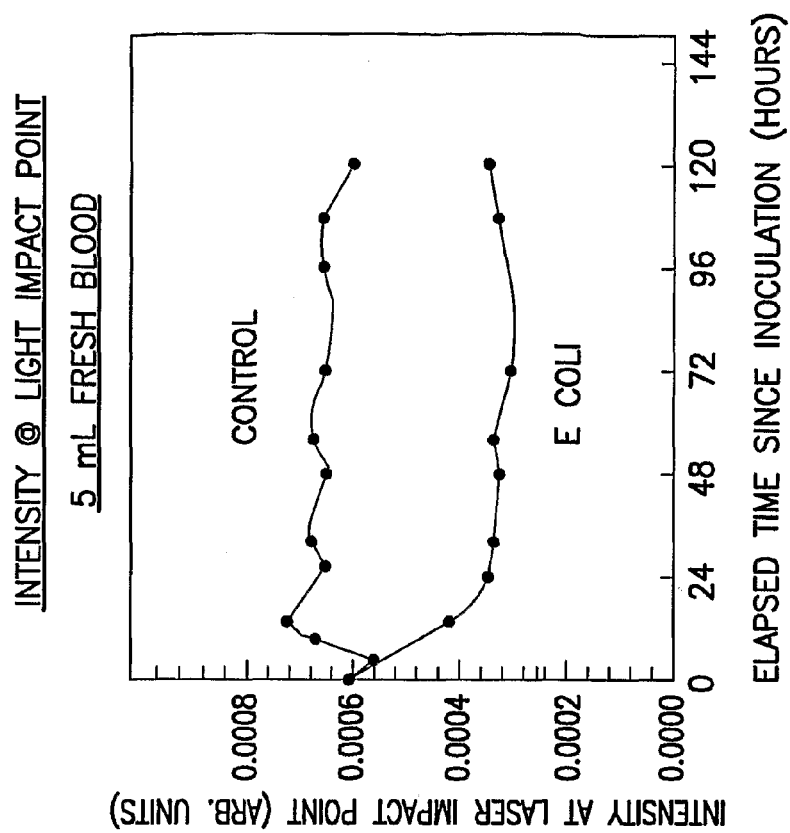
FIG. 25 is a graph that illustrates the light-impact-point intensity versus time for a first blood culture bottle containing a 5 mL control sample of fresh blood and a second blood culture bottle containing a 5 mL sample of blood and developed $E\ coli$ culture over a time period of approximately 5 days.

FIG. 25 is a graph that illustrates the light-impact-point intensity versus time for a first blood culture bottle containing a 5 mL control sample of fresh blood and a second blood culture bottle containing a 5 mL sample of blood and developed E coli culture over a time period of approximately 5 days.

Figure 26:
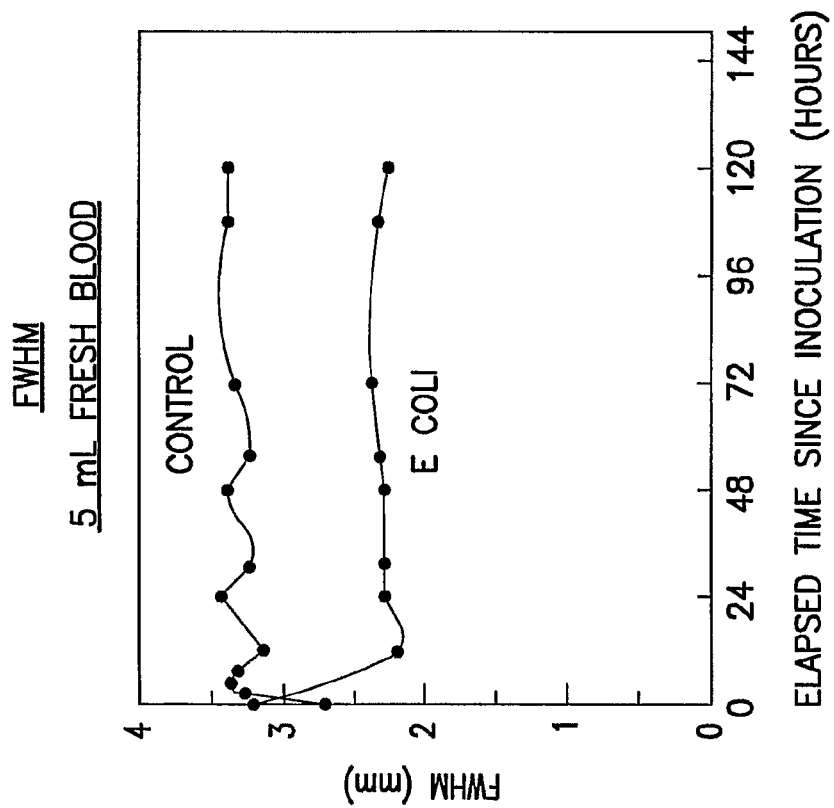
FIG. 26 is a graph that illustrates the full-width-at-half-maximum (FWHM) of the spatial distribution of backscattered light versus time for a first blood culture bottle containing a 5 mL control sample of fresh blood and a second blood culture bottle containing a 5 mL sample of blood and developed $E\ coli$ culture over a time period of approximately 5 days.

FIG. 26 is a graph that illustrates the full-width-at-half-maximum (FWHM) of the spatial distribution of backscattered light versus time for a first blood culture bottle containing a 5 mL control sample of fresh blood and a second blood culture bottle containing a 5 mL sample of blood and developed E coli culture over a time period of approximately 5 days.

Figure 27:
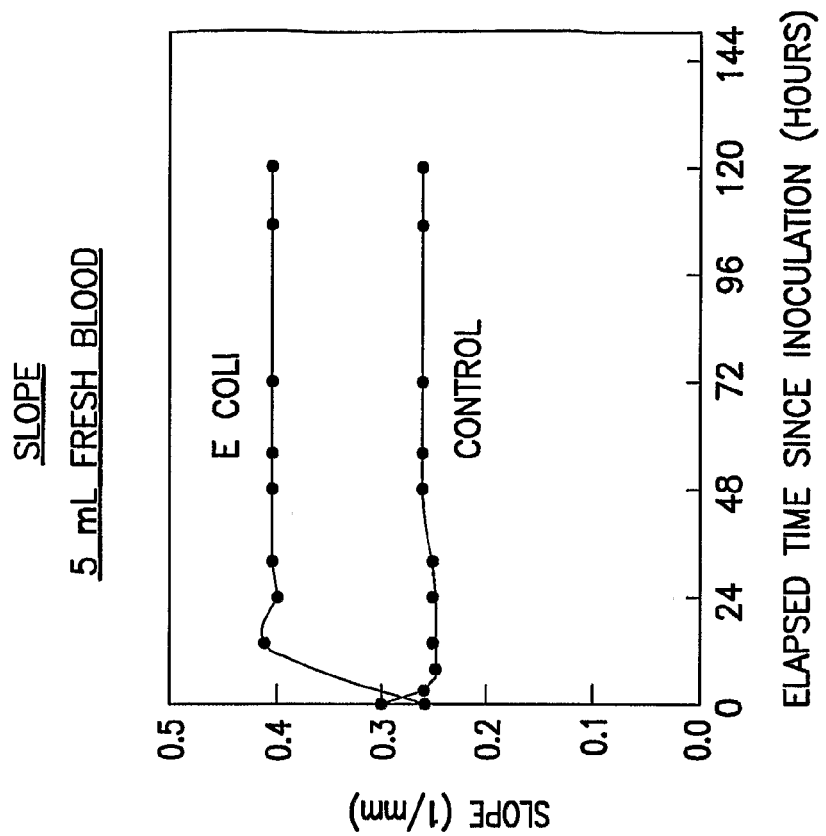
FIG. 27 is a graph that illustrates the slope of the spatial distribution of backscattered light versus time graph over time for a first blood culture bottle containing a control sample of 5 mL of fresh blood and a second blood culture bottle containing a 5 mL sample of blood and developed $E\ coli$ culture over a time period of approximately 5 days.

FIG. 27 is a graph that illustrates the slope of the spatial distribution of backscattered light versus time graph over time according to FIGS. 25 and 26 for a first blood culture bottle containing a control sample of 5 mL of fresh blood and a second blood culture bottle containing a 5 mL sample of blood and developed *E coli* culture over a time period of approximately 5 days.

EXAMPLE 11

Figure 28:
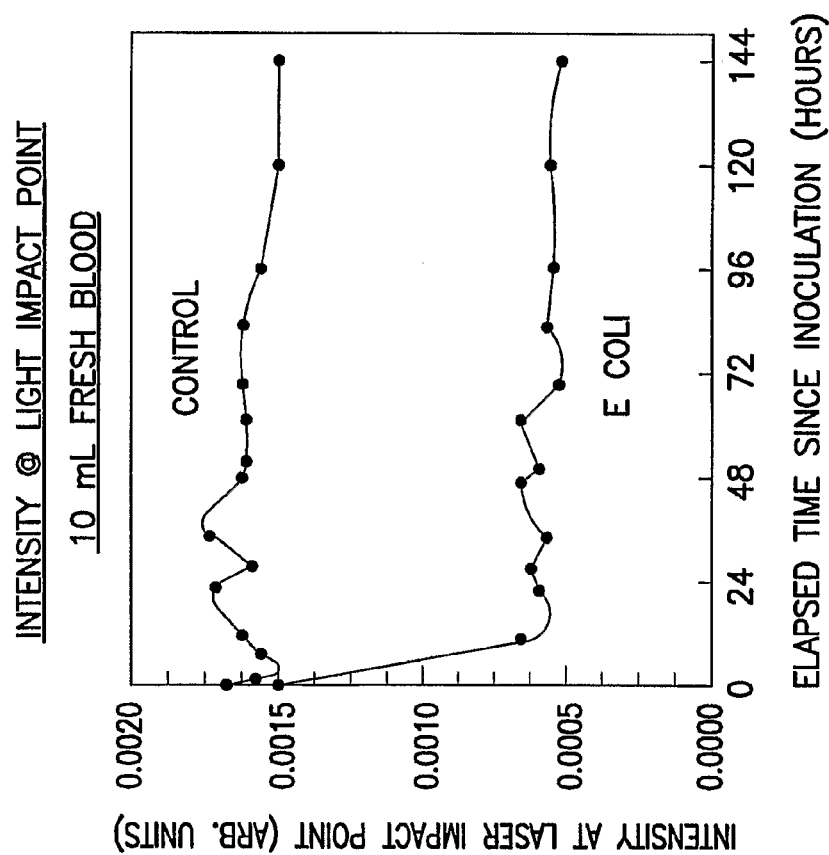
FIG. 28 is a graph that illustrates the light-impact-point intensity versus time for a first blood culture bottle containing a 10 mL control sample of fresh blood and a second blood culture bottle containing a 10 mL sample of blood and developed $E\ coli$ culture over a time period of approximately 5 days.

FIG. 28 is a graph that illustrates the light-impact-point intensity versus time for a first blood culture bottle containing a 10 mL control sample of fresh blood and a second blood culture bottle containing a 10 mL sample of blood and developed *E coli* culture over a time period of approximately 5 days.

Figure 29:
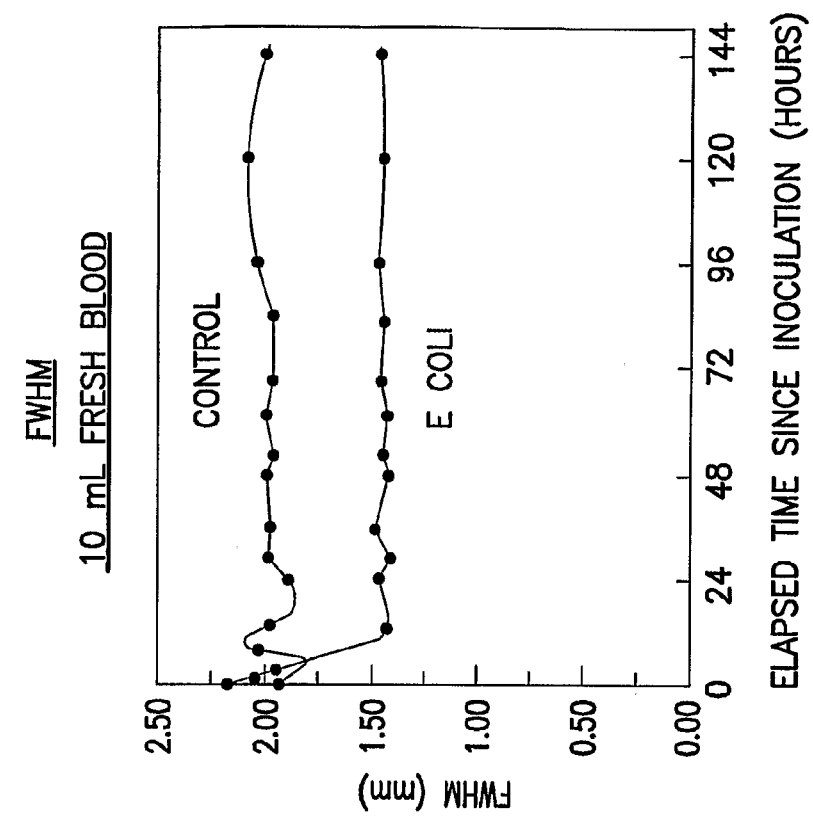
FIG. 29 is a graph that illustrates the full-width-at-half-maximum (FWHM) of the spatial distribution of backscattered light versus time for a first blood culture bottle containing a 10 mL control sample of fresh blood and a second blood culture bottle containing a 10 mL sample of blood and developed $E\ coli$ culture over a time period of approximately 5 days.

FIG. 29 is a graph that illustrates the full-width-at-half-maximum (FWHM) of the spatial distribution of backscattered light intensity versus time for a first blood culture bottle containing a 10 mL control sample of fresh blood and a second blood culture bottle containing a 10 mL sample of blood and developed *E coli* culture over a time period of approximately 5 days.

Figure 30:
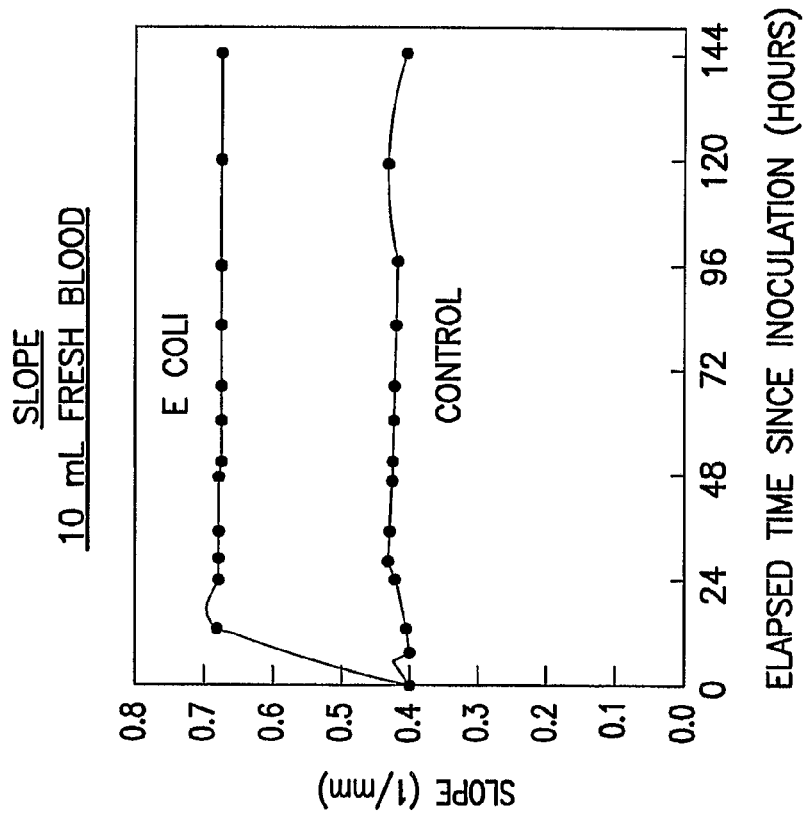
FIG. 30 is a graph that illustrates the slope of the spatial distribution of backscattered light versus time graph over time for a first blood culture bottle containing a control sample of 10 mL of fresh blood and a second blood culture bottle containing a 10 mL sample of blood and developed $E\ coli$ culture over a time period of approximately 5 days.

FIG. 30 is a graph that illustrates the slope of the spatial distribution of backscattered light versus time graph over time according to FIGS. 28 and 29 for a first blood culture bottle containing a control sample of 10 mL of fresh blood and a second blood culture bottle containing a 10 mL sample of blood and developed *E coli* culture over a time period of approximately 5 days.

EXAMPLE 12

Figure 31:
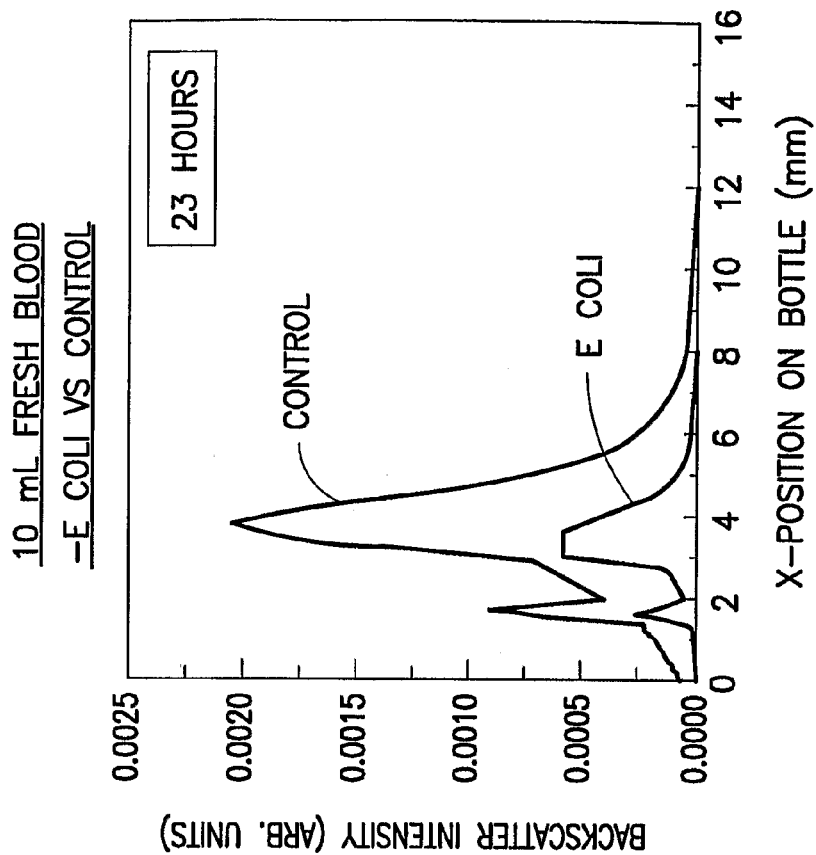
FIG. 31 is a graph that illustrates the backscatter distribution change for a negative blood culture bottle (i.e., a control blood culture bottle) that becomes a blood culture bottle with a fully developed $E\ coli$ culture for 10 mL of fresh blood.

FIG. 31 is a graph that illustrates the backscatter distribution change for a negative blood culture bottle (i.e., a control blood culture bottle) (2) that becomes a blood culture bottle (1) with a fully developed *E coli* culture for 10 mL of fresh blood.

EXAMPLE 13

Figure 32:
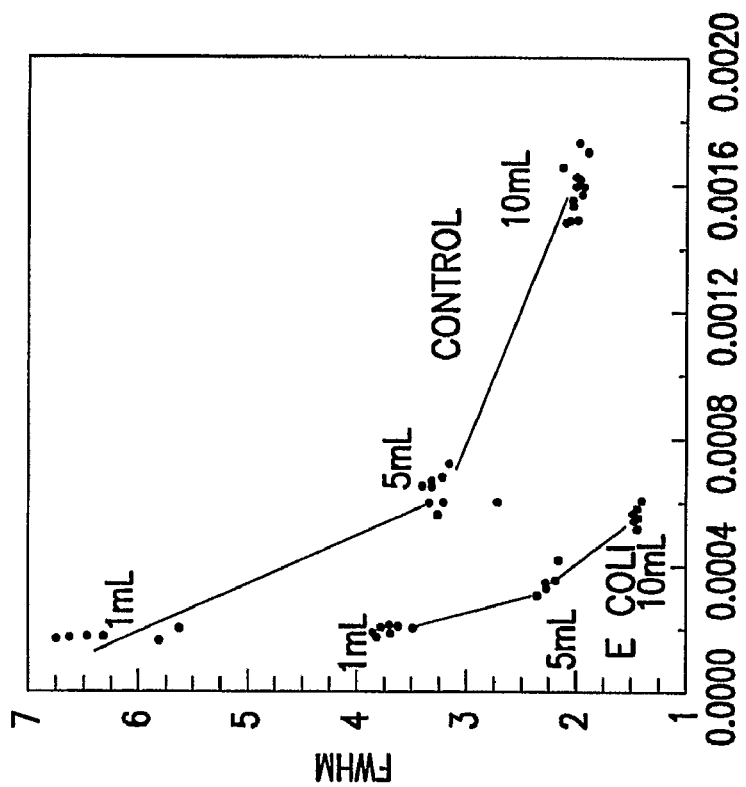
FIG. 32 is a two-dimensional (2D) graph that illustrates the FWHM versus backscatter intensity at the light-impact-point (IALIP) for six blood culture bottles, a first (control bottle) containing 1 mL of fresh blood, a second containing 1 mL of blood and developed $E\ coli$ culture, a third (control bottle) containing 5 mL of fresh blood, a fourth containing 5 mL of blood and developed $E\ coli$ culture, a fifth (control bottle) containing 10 mL of fresh blood and a sixth containing 10 mL of blood and developed $E\ coli$ culture, recorded over a time period of approximately 6 days.

FIG. 32 is a two-dimensional (2D) graph that illustrates the FWHM versus backscatter intensity at the light-impact-point (IALIP) for six blood culture bottles, a first (control bottle) containing 1 mL of fresh blood, a second containing 1 mL of blood and developed *E coli* culture, a third (control bottle) containing 5 mL of fresh blood, a fourth containing 5 mL of blood and developed *E coli* culture, a fifth (control bottle) containing 10 mL of fresh blood and a sixth containing 10 mL of blood and developed *E coli* culture, recorded over a time period of approximately 6 days. To generate this 2D plot, all the data points shown in FIGS. 20, 21, 25, 26, 28, and 29 have been utilized. The six clusters of points in FIG. 32 provide information about the error that can be expected if only one measurement were to be performed at any given time during the 5-day period on a bottle of un-known status. As can be seen, despite a certain spreading of the data points, a clear separation between the three groups of control bottles (1, 5 and 10 mL) and the corresponding groups of positive bottles is possible.

Using the methods according to the embodiments of the present invention as described herein below, and the 2D presentation of FIG. 32, a decision relative to the presence or absence of a developed microorganism population can be made by comparing the data measured on a bottle (1) under test with pre-recorded calibration data. For example, since the measurements illustrated in FIGS. 22, 25-30 and 32 represents data from bottles of a known the status, this data can be used as calibration data for future measurements on bottles of an un-known status.

EXAMPLE 14

Figure 33:
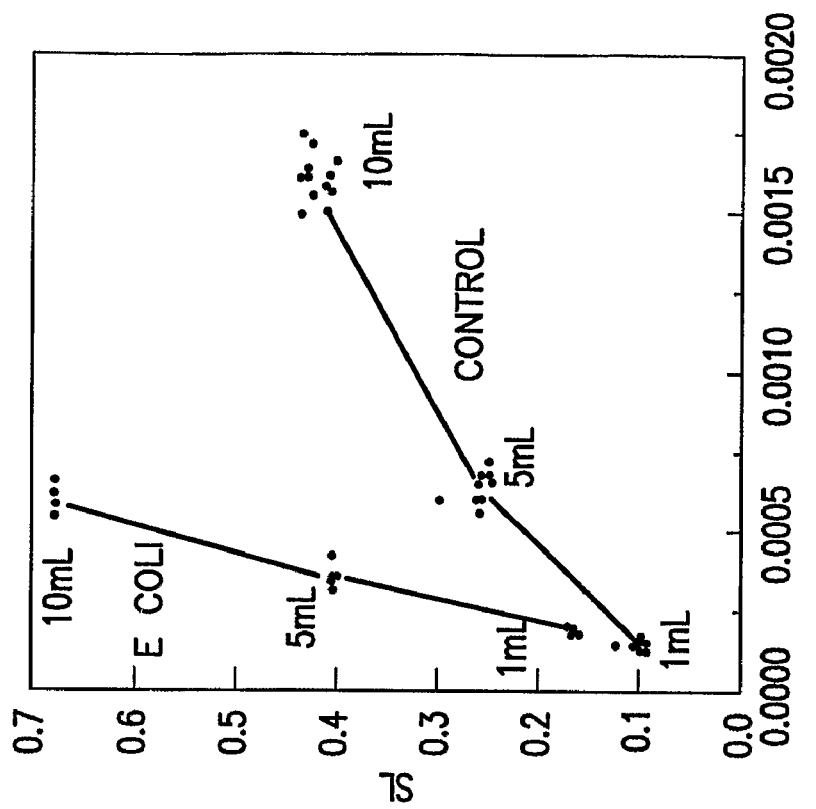
FIG. 33 is a 2D graph that illustrates SL versus IALIP for six blood culture bottles, a first (control bottle) containing 1 mL of fresh blood, a second containing 1 mL of blood and developed $E\ coli$ culture, a third (control bottle) containing 5 mL of fresh blood, a fourth containing 5 mL of blood and developed $E\ coli$ culture, a fifth (control bottle) containing 10 mL of fresh blood and a sixth containing 10 mL of blood and developed $E\ coli$ culture, recorded over a time period of approximately 6 days.

FIG. 33 is a 2D graph that illustrates the SL versus IALIP for six blood culture bottles, a first (control bottle) containing 1 mL of fresh blood, a second containing 1 mL of blood and developed *E coli* culture, a third (control bottle) containing 5 mL of fresh blood, a fourth containing 5 mL of blood and developed *E coli* culture, a fifth (control bottle) containing 10 mL of fresh blood and a sixth containing 10 mL of blood and developed *E coli* culture, recorded over a time period of approximately 6 days.

To generate the 2D plot shown in FIG. 33, data points shown in FIGS. 20, 22, 25, 26, 28, and 29 have been utilized. Again, a clear differentiation between a control bottle and a positive bottle is apparent.

EXAMPLE 15

Figure 34:
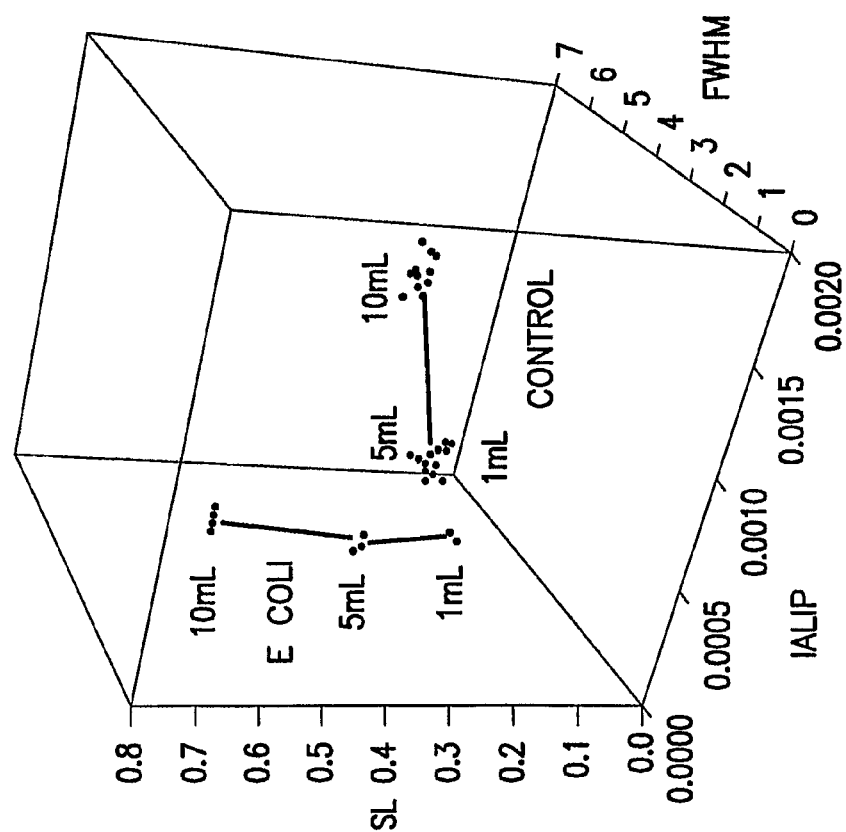
FIG. 34 is a three-dimensional (3D) graph illustrating the SL versus FWHM versus IALIP for six blood culture bottles, a first (control bottle) containing 1 mL of fresh blood, a second containing 1 mL of blood and developed $E\ coli$ culture, a third (control bottle) containing 5 mL of fresh blood, a fourth containing 5 mL of blood and developed $E\ coli$ culture, a fifth (control bottle) containing 10 mL of fresh blood and a sixth containing 10 mL of blood and developed $E\ coli$ culture, recorded over a time period of approximately 6 days.

FIG. 34 is a three-dimensional (3D) graph illustrating the SL versus FWHM versus IALIP for six blood culture bottles, a first (control bottle) containing 1 mL of fresh blood, a second containing 1 mL of blood and developed *E coli* culture, a third (control bottle) containing 5 mL of fresh blood, a fourth containing 5 mL of blood and developed E coli culture, a fifth (control bottle) containing 10 mL of fresh blood and a sixth containing 10 mL of blood and developed *E coli* culture, recorded over a time period of approximately 6 days. To generate the 3D plot of FIG. 34, data points shown in FIGS. 20-22 and 25-30 have been utilized, and an even better differentiation than that shown in FIGS. 32 and 33 between the control bottles and the positive bottles is apparent.

EXAMPLE 16

Figure 35:
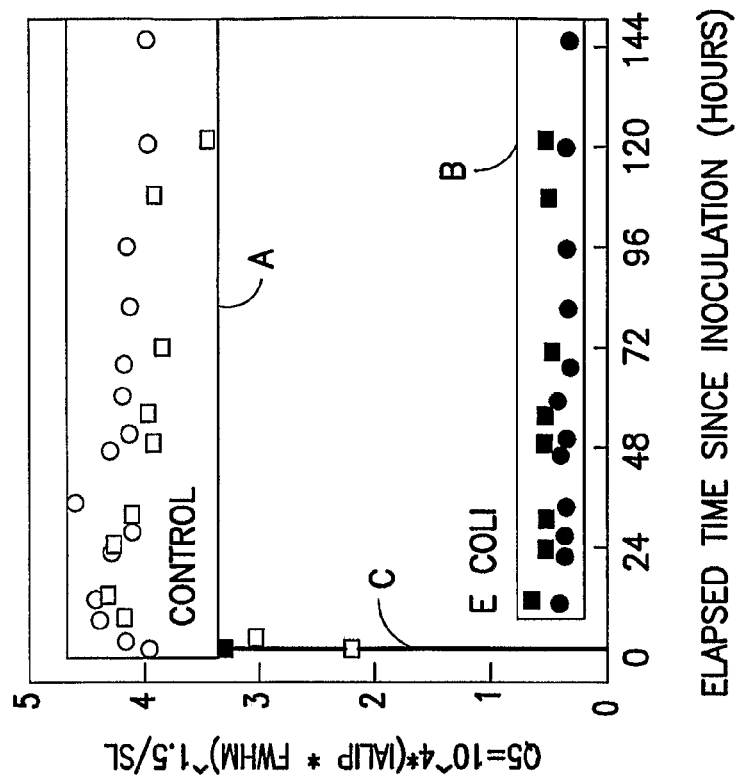
FIG. 35 illustrates measurements of a processed analytical feature Q5 of the backscatter distribution for four blood culture bottles, a first (control bottle) containing 5 mL of fresh blood, a second containing 5 mL of blood with developed $E\ coli$ cultures, a third (control bottle) containing 10 mL of fresh blood and a fourth containing 10 mL of blood with developed $E\ coli$ cultures, over a time period of approximately 6 days.

FIG. 35 illustrates measurements of a processed analytical feature Q5 of the backscatter distribution for four blood culture bottles, a first (control bottle) containing 5 mL of fresh blood, a second containing 5 mL of blood with developed *E coli* cultures, a third (control bottle) containing 10 mL of fresh blood and a fourth containing 10 mL of blood with developed *E coli* cultures, over a time period of approximately 6 days. FIG. 35 shows a processed feature, Q5 versus the elapsed time since inoculation in a 2D data representation. The processed analytical feature Q5 has been generated by combining the analytical features IALIP, FWHM, and SL according to the following equation, Equation (12).

Equation (12):

$$Q5 = \frac{10^4 * (IALIP * FWHM)^{1.5}}{SL}$$

Figure 37:
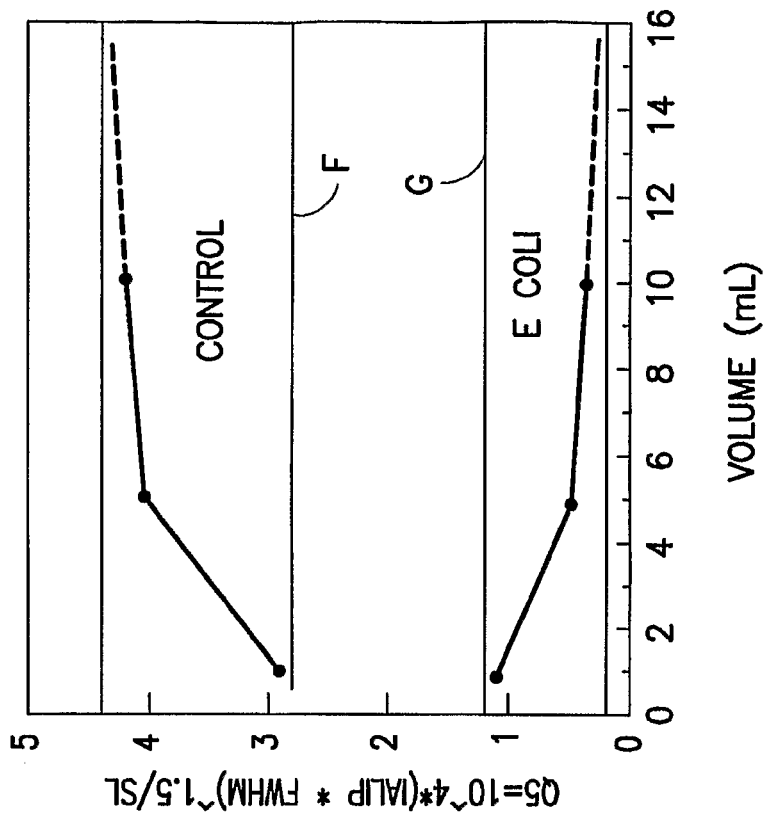
FIG. 37 is a graph illustrating the mean values of the post-processing parameter Q5 of the backscatter distribution for six blood culture bottles, a first (control bottle) containing 1 mL of fresh blood, a second containing 1 mL of blood with developed *E coli* cultures, a third (control bottle) containing 5 mL of fresh blood, a fourth containing 5 mL of blood with developed *E coli* cultures, a fifth (control bottle) containing 10 mL of fresh blood and a sixth containing 10 mL of blood with developed *E coli* cultures and further includes dashed lines representing an extrapolation towards 15 mL of blood for both the control samples and the samples containing blood with developed *E coli* cultures.

The formulaic combination of IALIP, FWHM, and SL has been chosen so as to obtain maximum separation between control and positive bottle data, but minimizing the dependency of Q5 on the blood volume. In FIG. 37, square symbols represent 5 mL data, and round symbols represent 10 mL data. Most of the control points are located within field A, and most of the *E coli* points are located within field B. The dashed line C corresponds to the time of inoculation. As expected, the *E coli* data points measured immediately after inoculation are located very close to the control data points. Overall, after a very brief period of time, there is a perfect separation between the control data points and the *E coli* data points. Therefore, the processed feature Q5 represents excellent data for making a decision relative to the presence or absence of a developed microorganism population within the corresponding blood culture bottle (1).

EXAMPLE 17

Figure 36:
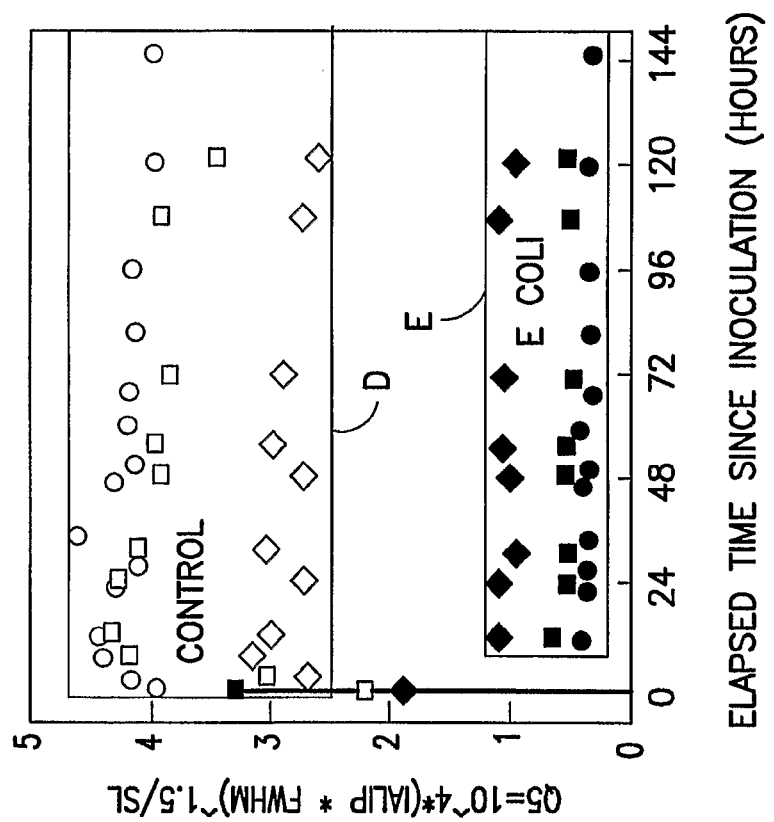
FIG. 36 illustrates a second set of measurements of the processed analytical feature Q5 of the backscatter distribution for six blood culture bottles, a first (control bottle) containing 1 mL of fresh blood, a second containing 1 mL of blood with developed *E coli* cultures, a third (control bottle) containing 5 mL of fresh blood, a fourth containing 5 mL of blood with developed *E coli* cultures, a fifth (control bottle) containing 10 mL of fresh blood and a sixth containing 10 mL of blood with developed *E coli* cultures, over a time period of approximately 6 days.

FIG. 36 illustrates a second set of measurements of the processed analytical feature Q5 of the backscatter distribution for six blood culture bottles (2), a first (control bottle) containing 1 mL of fresh blood, a second containing 1 mL of blood with developed *E coli* cultures, a third (control bottle) containing 5 mL of fresh blood, a fourth containing 5 mL of blood with developed *E coli* cultures, a fifth (control bottle) containing 10 mL of fresh blood and a sixth containing 10 mL of blood with developed *E coli* cultures, over a time period of approximately 6 days. As above in regard to FIG. 35, most control data points shown in FIG. 36 are located within a first field, D, and most *E coli* data points are located within a second field, E. The only "outliers" are those data points observed immediately after inoculation. Consequently, FIG. 36 demonstrates that the method according to the embodiments of the present invention provides for rapid differentiation between negative and positive blood culture bottles for a blood volume range between 1 mL and 10 mL.

EXAMPLE 18

FIG. 37 is a graph illustrating the mean values of the post-processing parameter Q5 of the backscatter distribution for six blood culture bottles (2), a first (control bottle) containing 1 mL of fresh blood, a second containing 1 mL of blood with developed E coli cultures, a third (control bottle) containing 5 mL of fresh blood, a fourth containing 5 mL of blood with developed *E coli* cultures, a fifth (control bottle) containing 10 mL of fresh blood and a sixth containing 10 mL of blood with developed *E coli* cultures and further includes dashed lines representing an extrapolation towards 15 mL of blood for both the control samples and the samples containing blood with developed *E coli* cultures. The dashed lines of FIG. 37 represent an extrapolation towards 15 mL of blood. That all the control data points are within a first field, F, and all *E coli* data points are within a second field, G, is indicative of the capability of the method according to the embodiments of the present invention to differentiate between negative and positive blood culture bottles over a blood volume range from 1 mL up to 15 mL.

Figure 38:
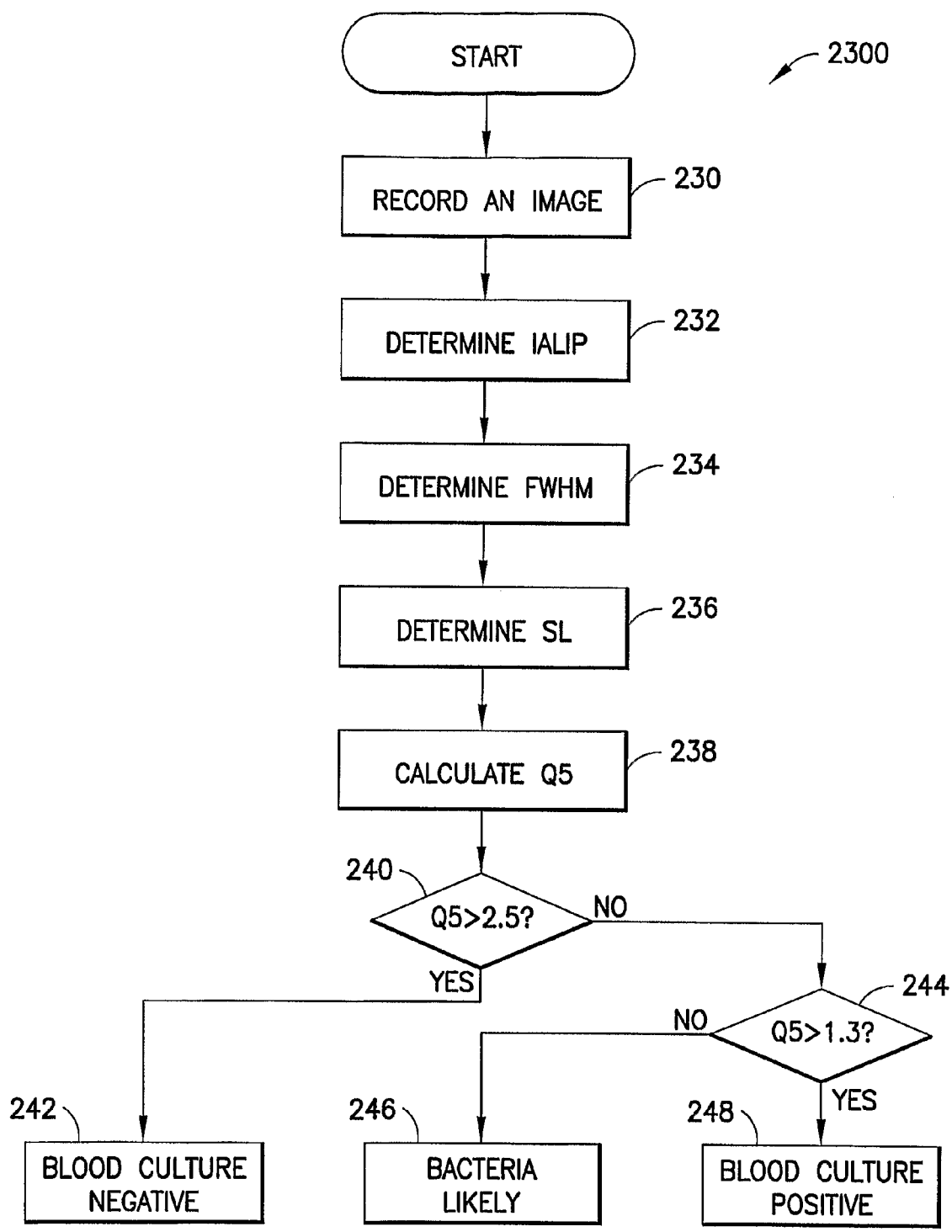
FIG. 38 is a flow chart illustrating a method determining the presence or absence of a developed microorganism population according to an embodiment of the present invention.

FIG. 38 is a flow chart illustrating a method for determining the presence or absence of a developed microorganism population according to an embodiment of the present invention;. This flow chart illustrates steps in a method according to an embodiment of the present invention that utilizes the data shown in FIG. 36 to determine the status of a blood culture bottle under test. The method presented in the flow chart shown in FIG. 38 is applicable for a range of blood volume values between about 1 mL to 15 mL.

The method 2300 of this embodiment for determining whether a blood culture bottle (1) is positive or negative begins with step 230. In step 230, a blood culture bottle (1) is placed in the apparatus as shown in FIG. 3A (although other configurations can be used practice the method of the invention as described herein), and an image (i.e., the asymmetric spatial backscatter distribution (15)) is recorded by the photodetector (19), and results stored. In one embodiment of the present invention, the results (similar to those displayed in FIG. 4) are digitized and stored in a computer 25 connected to the photodetector (19), and possible remotely accessed by an operator via a network (LAN, WAN Internet, and so on). Either manually, or through sue of data analysis software, the IALIP is determined in step 232, the FWHM is determined in step 234 and the SL (18) is determined in step 236. The operator or software then determines Q5 according to equation (I) (discussed above) in step 238. In decision step 240, Q5 is compared to a first threshold, T1. T1, in one particular embodiment of the present invention, is set to 2.5, though, as one skilled in the art of the invention can appreciate, this need not be the case. Other values of T1 can be used, depending on the different slope formulas used, which also is discussed above.

If Q5 is greater than 2.5 ("Yes" path from decision step 240), then in step 242 a determination is made and announced to the operator that the blood culture sample is negative or that there is only a very small number of bacteria in the blood culture bottle (1). In this case, it would be advisable and would make sense to load the blood culture bottle into an automated bacterial detection system for further testing. If Q5 is less than 2.5 ("No" path from decision step 240), a second determination is made in decision step 244: Is Q5 less than T2? In this embodiment of the present invention, T2 is set to 1.3 If Q5 is also less than 1.3 ("Yes" path from decision step 244), then the determination is made that the blood culture bottle (1) is positive, or that there is bacteria of some type in the blood culture bottle (1). In this case, it would not be necessary to load the blood culture bottle (1) into an automated bacterial detection system. Instead, the blood culture bottle (1) can be immediately tested for bacterial identification and for antimicrobial susceptibility. The advantage here is that the result in regard to the presence of microorganisms is immediately available, and that no space is unnecessarily occupied in the automated bacterial detection system. If, however, it is determined that Q5 is greater than 1.3 (but less than 2.5), then it is likely there is bacteria present in the blood culture bottle (1), as determined in step 246 ("No" path from decision step 244). In this case, a microbial population may be in the development phase, and it would be advisable to load the bottle into an automated detection system for confirmation of the presumptive result.

The methods described above according to the embodiments of the present invention can be accomplished very rapidly, and, in the case of advanced and automated machinery, completely automatically even to the point of loading the blood culture bottles (1) onto a conveyor to be analyzed under the apparatus shown in FIG. 3A. The data can be quickly organized and stored, then shared over a network (as described above), reports can be generated, and so on.

EXAMPLE 19

Figure 39:
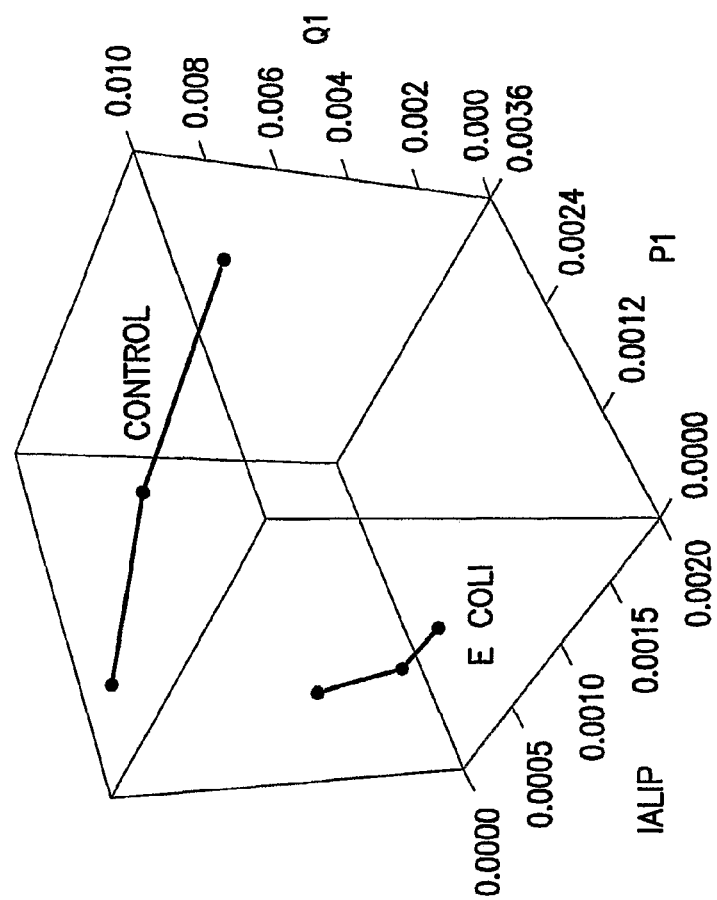
FIG. 39 is a 3D graph that illustrates 6-day mean values of an analytical feature IALIP, and processed analytical features P1 and Q1 according to an embodiment of the present invention.

FIG. 39 is a 3D graph that illustrates 6-day mean values of the analytical feature IALIP, and the processed analytical features P1 and Q1, defined by the equations (Equation 13 and Equation 14) for six blood culture bottles: a first (control bottle) containing 1 mL of fresh blood, a second containing 1 mL of blood with developed *E coli* cultures, a third (control bottle) containing 5 mL of fresh blood, a fourth containing 5 mL of blood with developed *E coli* cultures, a fifth (control bottle) containing 10 mL of fresh blood and a sixth containing 10 mL of blood with developed *E coli*.

$$P1 = IALIP * FWHM \qquad \text{Equation 13}$$

and $$Q1 = P1/SL \qquad \text{Equation 14}$$

By comparing FIG. 39 with FIG. 34, it becomes clear that processed analytical features as defined above provide an improved differentiation between negative and positive blood culture bottles (1). The processed analytical features P1, Q1, and Q5 as discussed above are only a few examples out of a multitude of possible processed analytical features. It is within the spirit and scope of the embodiments of the present invention to generate other processed analytical features that can be used to differentiate between positive and negative blood culture bottles. The same statement holds for the analytical features themselves. Furthermore, in this case, other analytical features can be selected and used. The method according to embodiments of the present invention is by no means limited to the use of 2D or 3D data representations and flow charts for making a decision relative to the presence or absence of a developed microorganism population. Instead, dedicated software can be used, allowing for the comparison of new data obtained from a bottle under test, with pre-recorded calibration data from other blood culture bottles (1) of known status.

EXAMPLE 20

Figure 40:
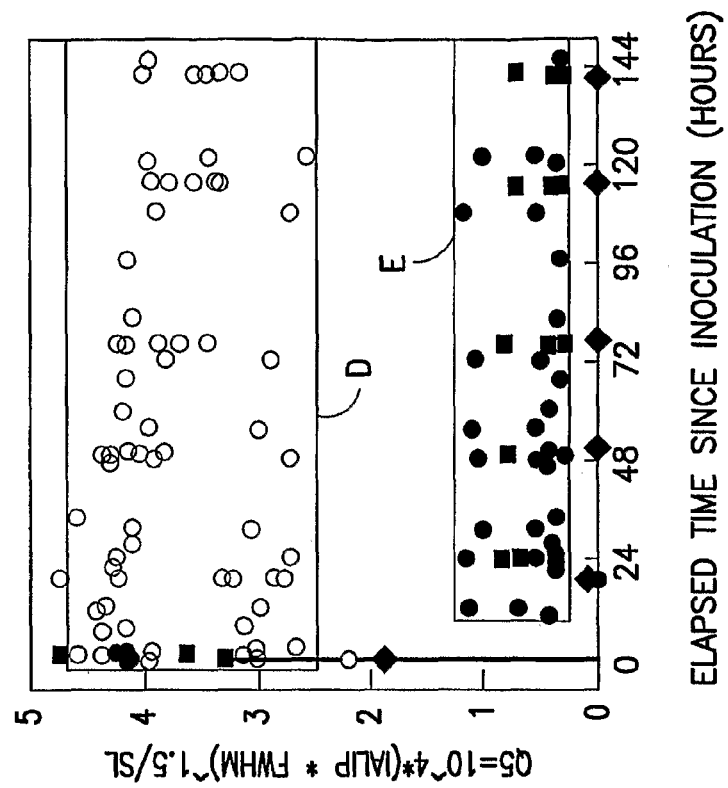
FIG. 40 is a 2D graph that illustrates the post-processing parameter Q5 of the backscatter distribution versus time for a number of control blood culture bottles and bottles containing samples of blood with developed *E coli, S epidermidis*, and Group B Strep cultures for various quantities from 2 to 12 mL, over a time period of approximately six days.
Figure 42:
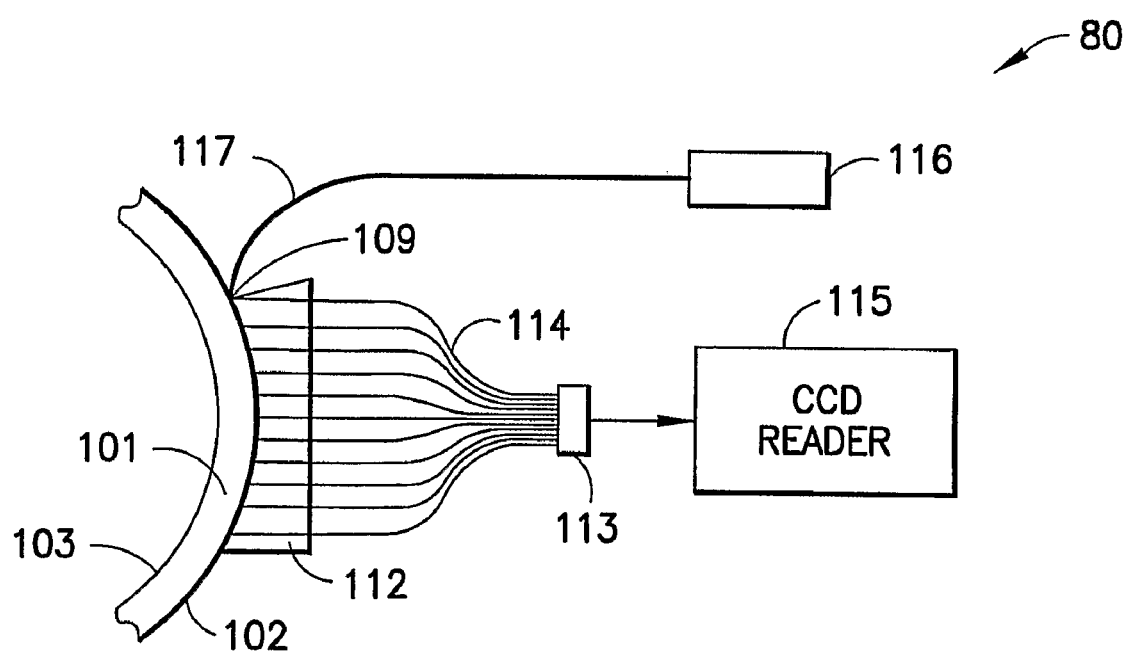
FIG. 42 illustrates schematically an apparatus according to an embodiment of the present invention similar to the apparatus of FIG. 41, but with an optical fiber for directing light onto the blood culture.

FIG. 40 is a 2D graph that illustrates the post-processing parameter Q5 of the backscatter distribution versus time for 12 blood culture bottles (1), six bottles containing control samples of fresh blood for various quantities from 2 to 12 mL and six bottles containing samples of blood with developed *E coli* cultures for various quantities from 2 to 12 mL, over a time period of approximately six days. FIG. 42 shows the same data as in FIG. 38, but results obtained from 2 ml to 12 mL of fresh blood over a time period of approximately 6 days, as measured for six control bottles, and for six bottles with developed cultures of *S epidermidis* and Group B Strep, have been added. FIG. 40 contains the very same fields D and E shown in FIG. 36. As can be seen, almost all controls are located within field D. The full circles in FIG. 40 represent the *E coli* data, the full squares represent the S epi data, and the diamonds are the Group B Strep data. While the separation between controls and S epi is very similar to the separation between controls and *E coli*, the separation is even higher for Group B Strep.

Similar results to those set forth herein are achievable with blood culture bottles containing developed cultures of the following microorganism species:
S. aureus
Ps. aeruginosa
S. pneumoniae
E. cloacae
S. faecalis
K. pneumoniae
Group A Strep
N. meningitidis
N. gonorrhoeae This list is by no means inclusive or limiting in regard to the embodiments of the present invention described herein. This list is shown merely as an example of some of the types of micro-organisms that can be detected by using the system and method of the embodiments of the present invention.

As has been discussed above, a bottle that is "still negative" may either contain no organisms at all, or it may contain only a relatively small number of organisms if that patient has in fact a bacterial infection. It should be emphasized that, in this case of a "still negative bottle", it does not matter what organisms are present. The method according to an embodiment of the present invention will clearly classify the culture bottle as "still negative".

In embodiments of the present invention, the methods (i.e., the method of determining the volume and hematocrit value of a blood sample and method of rapidly differentiating between positive and negative blood cultures) may be performed at the same time or at separate times (i.e., one method performed before the other method). If performed at different times, the methods may be performed in any order.

The method of this embodiment, besides its ability to rapidly differentiate between negative and positive blood culture bottles, can also be applied for the detection of microorganisms in blood culture bottles. One would start exactly as described above, but would know that all bottles under test are still negative. The method above would then be applied on the bottles under test in a repetitive mode every ten minutes over an extended period of time, such as five days. If a microorganism population that is present within a particular bottle has been grown sufficiently in number, the analytical features and processed features according to the present invention will show changes, which is an indication of positivity.

The methods of the present invention work on aerobic blood culture bottles with or without resin beads. The methods work also on lytic blood culture bottles wherein the red blood cells are being ruptured by means of certain chemicals. Other types of culture vessels are similarly able to be used. The exact values obtained for the different analytical features depend on the specific details of the apparatus used, such as the laser wavelength, the angle between the light beam and a normal to the bottle wall as discussed, the imaging conditions, and the photodetector used, among others. The methods work also for slightly modified experimental details of the apparatus, if the required calibration data are produced and pre-recorded under equal experimental conditions.

In all the above described embodiments of the present invention, a light beam is directed onto the wall of a blood culture bottle at a primary beam impact point in such a way that the light beam deviates from a normal to the bottle wall at the primary beam impact point by an angle between about zero and 90 degrees. If the angle becomes very small, the generated spatial distribution of backscattered light becomes more and more symmetrical. While the information generated in the asymmetrical distribution is advantageous, the symmetrical spatial distribution also carries information about the status of the blood culture sample.

Figure 41:
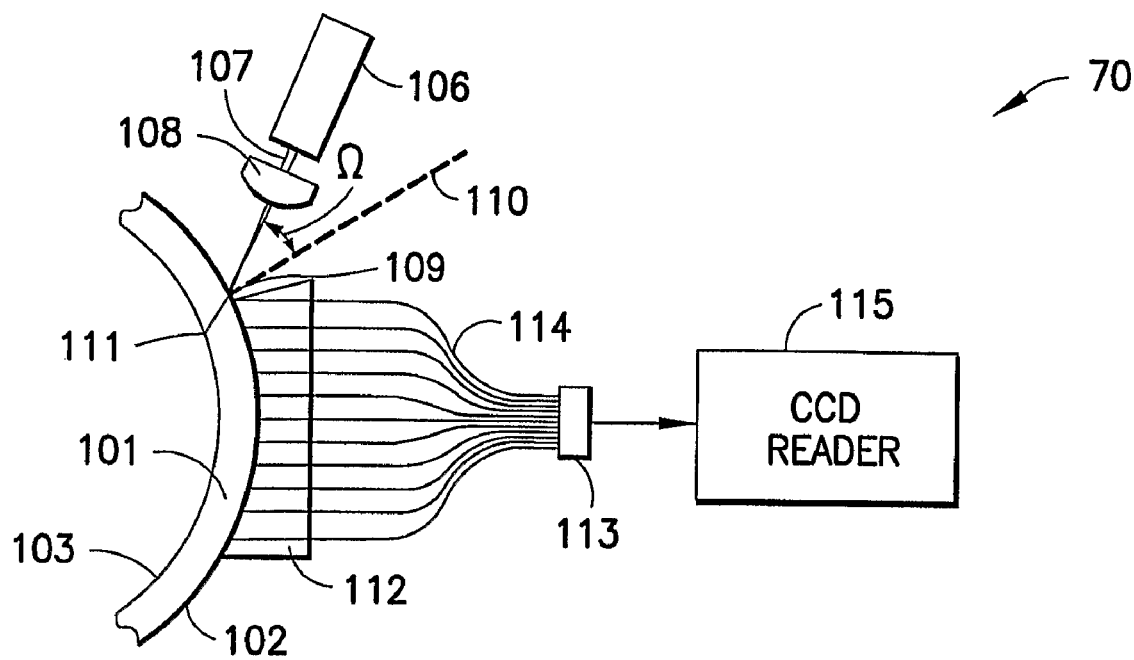
FIG. 41 illustrates schematically an apparatus according to an embodiment of the present invention similar to the apparatus of FIG. 1A, but with an imaging device in the form of an array of optical fibers.

FIG. 41 illustrates schematically an apparatus according to an embodiment of the present invention similar to the apparatus of FIG. 1A, but with an imaging device in the form of an array of optical fibers. FIG. 41 depicts an alternative setup (70) wherein a light beam (107) emitted by an optical source (106) is focused onto the wall (101) of a blood culture bottle (100) by a lens (108) at a primary beam impact point (109) on the outer bottle wall interface (102), wherein the light beam (107) deviates from a normal (110) to the bottle wall (101) at the primary beam impact point (109) by an angle $\Omega$. Light beam (107) refracts into the wall (101) and arrives at the bottle wall's inner interface (103) at a secondary beam impact point (111), where it enters the liquid blood culture suspension, and generates a spatial asymmetric backscatter distribution. An array of optical fibers (fibers) (114) is positioned against the outer bottle wall interface (102), and held in place by means of a block (112) so that the photons re-emitted by the blood culture enter the input end of the fibers (114). The output ends of fibers (114) are optically coupled onto a charge coupled device (CCD) array (113), which is connected to a dedicated CCD reader (115). Due to the fact that the inputs of fibers (114) are positioned in proximity to outer wall interface (102), and the fiber outputs of said fibers (114) are in proximity to CCD array (113), the arrangement shown in FIG. 41 can be referred to as a "proximity-focus configuration".

A further embodiment is illustrated in FIG. 42. The apparatus (80) of FIG. 42 differs from the apparatus of FIG. 41 in that a laser (116) with an attached optical excitation fiber (117) is present as an optical source, wherein the output end of excitation fiber (117) is arranged at outer wall interface (102) of bottle wall (101) at a primary beam impact point (109). In this configuration, the axis of fiber (117), at its output end, deviates from a normal to the bottle wall interface (102) at the primary beam impact point (109) by a certain angle. The apparatus (80) of FIG. 42 is substantially similar to the arrangements shown in FIGS. 1A, 3A, and 3B. The apparatus (80) according to the embodiment of the present invention illustrated in FIG. 42 has the advantage that no optical beams propagate in the open air, that no precision optical adjustment of optical elements is required, and that the apparatus (80) according to FIG. 42 can be somewhat smaller in size.

Figure 43A:
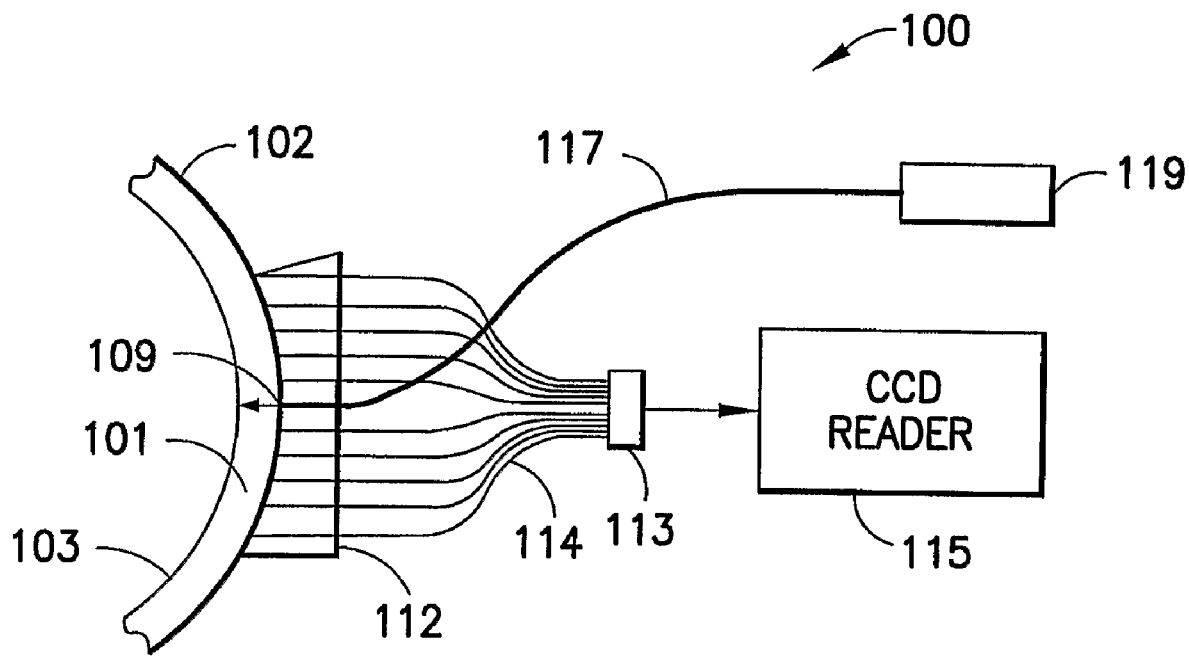
FIG. 43A illustrates a modification of the blood culture optical measurement apparatus according to an embodiment of the present invention.
Figure 43B:
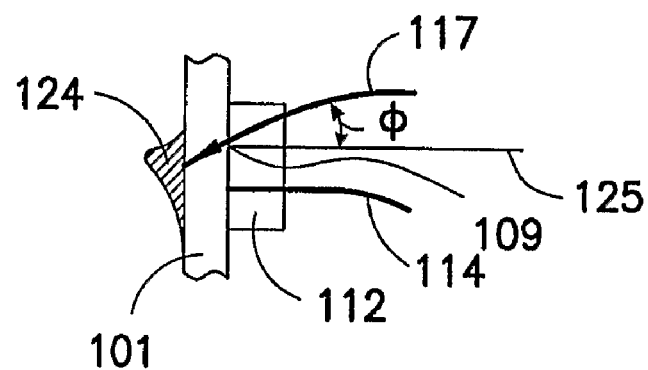
FIG. 43B illustrates a detail view of the apparatus of FIG. 43A.

FIGS. 43A and 43B illustrate a further embodiment. The apparatus (100) of FIGS. 43A and 43B is similar to the apparatus (80) in FIG. 42 in that there is an array of optical fibers (114) present to image a second asymmetric spatial backscatter light distribution (124) onto a photodetector (113). The apparatus (100) also comprises an excitation fiber (117) to direct light from a laser (116) onto the bottle wall (101). However, while in the apparatus of FIG. 42 the output of the excitation fiber is positioned near one end of the fiber array, the output of excitation fiber (117) in the apparatus of FIG. 43A is positioned near the center of fiber array (114). The axis of excitation fiber (117) at its output deviates from a normal (125) to the outer wall interface at the primary beam impact point (109) by a certain angle Φ. By utilizing the configuration of FIGS. 45A and 45B, the second asymmetric spatial backscatter light distribution (124) is produced, similar to the cases of other apparatus according to the embodiments of the present invention described above. By generating the second asymmetric spatial backscatter light distribution (124), the capability of differentiating between positive and negative blood cultures with low blood volume is improved, as described in greater detail above. In the arrangement of FIGS. 43A and 43B, fiber array (114) acquires a cross-section of the second asymmetric spatial backscatter light distribution (124) that is oriented perpendicular to the direction used in the apparatus (60, 70, 80) according to embodiments of the present invention described above.

Figure 44A:
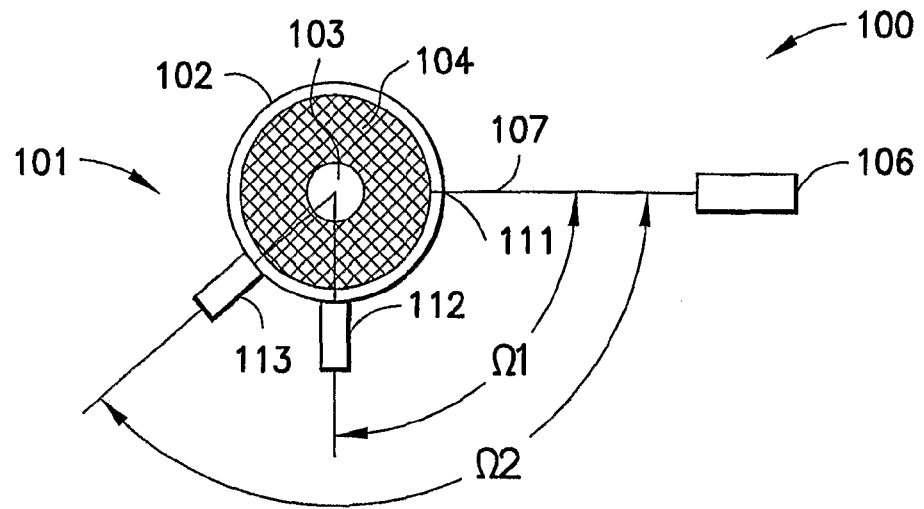
FIG. 44A illustrates a third blood culture optical measurement apparatus for practicing the method according to an embodiment of the present invention having two photodetectors to measure the light intensity re-emerging from the blood culture bottle at two different locations.

FIG. 44A illustrates an embodiment having two photodetectors to measure the light intensity re-emerging from the blood culture bottle at two different locations. The apparatus (100) shown in FIG. 44A can be considered as a stripped down version of the blood culture optical measurement apparatus (50) shown in FIG. 1A. The apparatus (50) of FIG. 1A images a whole section of the spatial distribution of backscattered light onto a plane and records it using a photodetector (13). In the apparatus (100) shown in FIG. 44A, only the backscattered intensity from two separate point-like locations of the asymmetric spatial backscatter light distribution are monitored and recorded. By measuring only two intensities, a modified slope must be calculated. Furthermore, in the apparatus (50) of FIG. 1A, a distance along the bottle wall is determined over which the intensity decreases by a given factor. In the apparatus (100) of FIG. 44A, however, a factor that characterizes the decrease in intensity over a given distance is provided.

The apparatus (100) of FIG. 44A comprises a blood culture bottle (101) having a bottle wall (102) and includes a septum (103) for sealing the bottle (101). The bottle (101) contains a mixture of growth media and blood (104). A light beam (107) emitted by a light source (106) such as a laser, is directed onto an optically transparent area of the bottle wall (102) at a first point of impact (111). The light beam (107) is positioned such that it deviates from a normal to the bottle wall (102) at the first point of impact (111) by a specific angle. The light beam (107) then generates an asymmetric spatial backscatter light distribution from the mixture of growth media and blood (mixture) (104) near the first point of impact (111). The light beam (107) deviates from a normal to the bottle wall (102) at the first point of impact (111) mainly to avoid back-reflected laser photons from entering the laser. This angle can be very small, however, and, therefore is not shown in FIG. 44A.

A first photodetector (112) of the apparatus is mounted adjacent to the bottle wall (102) at a first location by an angle Ω1 of approximately 90 degrees away from the first point of impact (111), and receives backscattered light from the blood (104). A second photodetector (113) of the apparatus is mounted adjacent to the bottle wall (102) at a second location by an angle Ω2 of approximately 135 degrees away from the first point of impact (111), and also receives backscattered light from mixture (104).

Figure 44B:
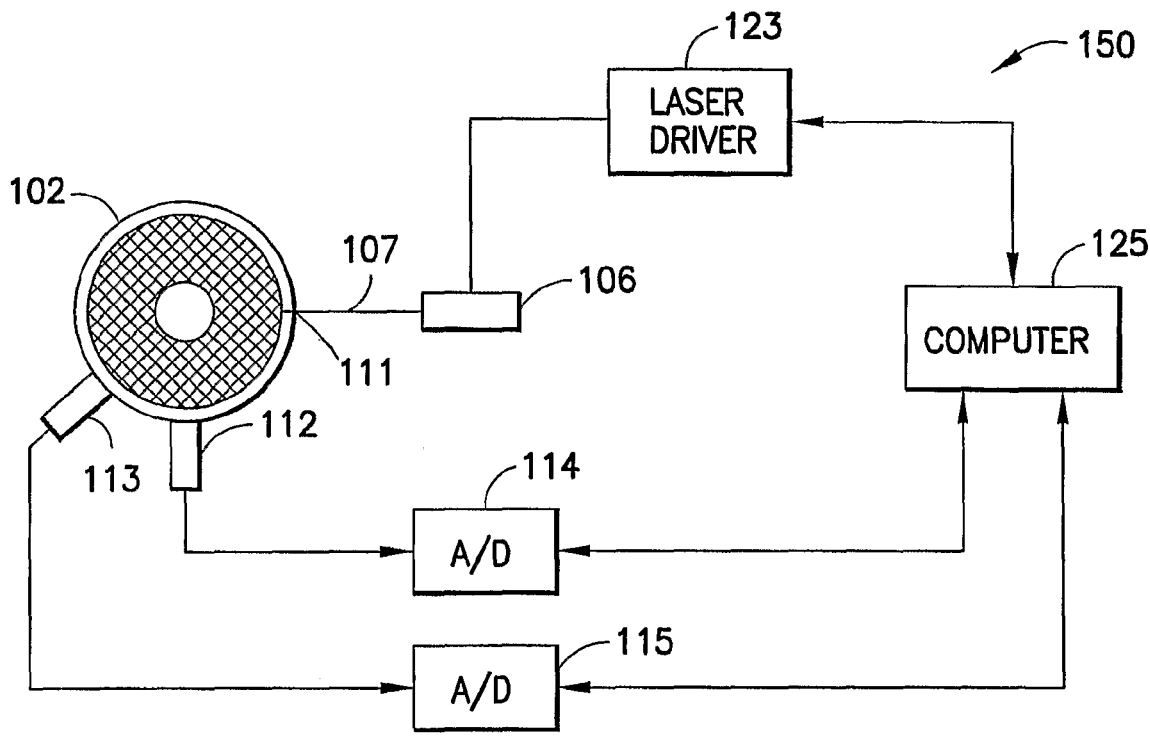
FIG. 44B illustrates a schematic block diagram of a blood culture optical measurement system for practicing the method according to an embodiment of the present invention having two photodetectors disposed onto two locations on the blood culture bottle.

FIG. 44B illustrates a schematic block diagram of a blood culture optical measurement system 150 of the type shown in FIG. 46A. Laser (106) is connected to a laser driver of the blood culture optical measurement system (123), which in turn is connected with a computer (125). The output of first photodetector (112) is connected with a first A/D converter (114), and the output of the first A/D converter (114) is connected to the computer (125). Correspondingly, the output of the second photodetector (113) is connected to a second A/D converter (115), and the output of the second A/D converter (115) is also connected to the computer (125).

EXAMPLE 6920

Figure 45:
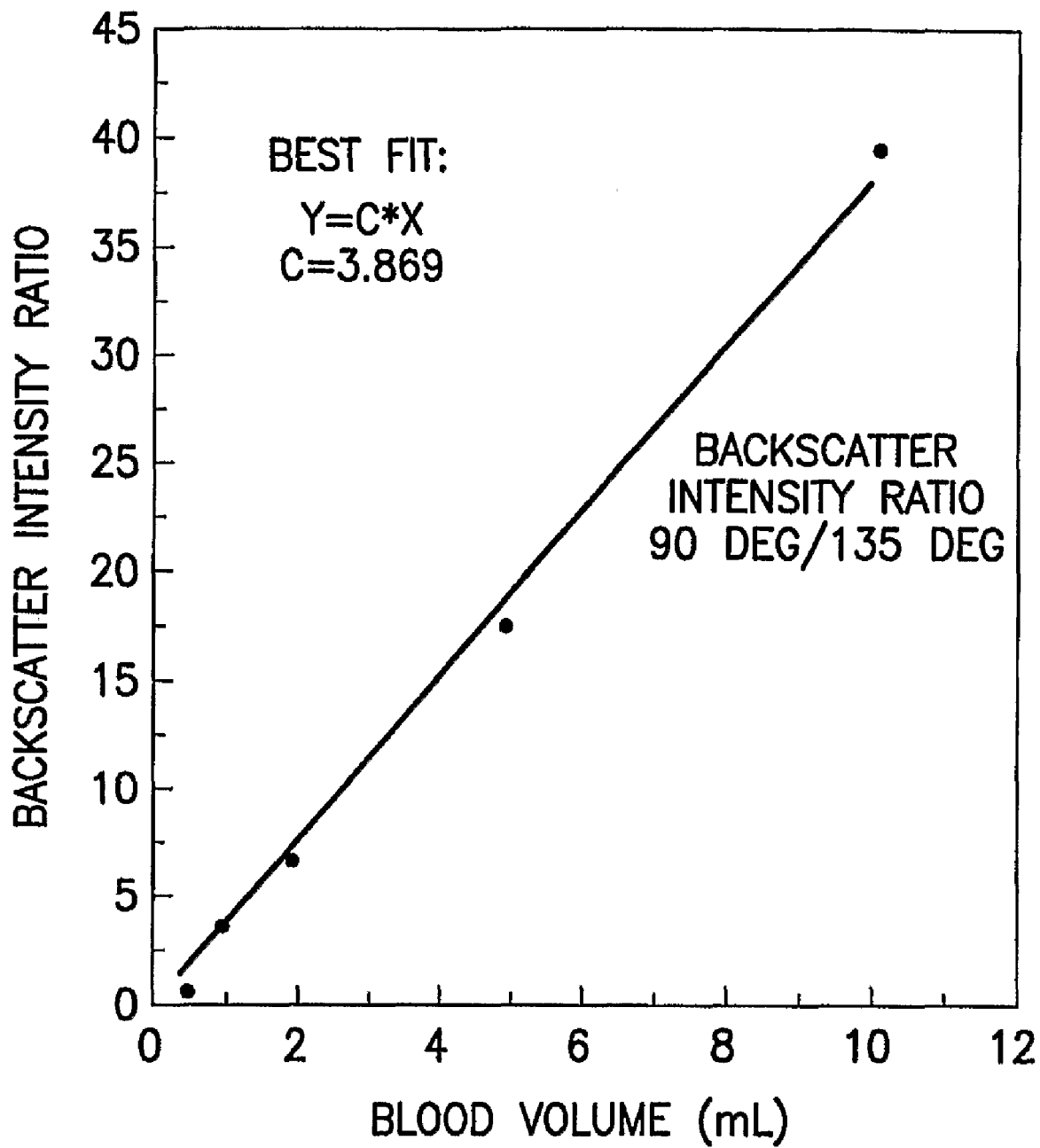
FIG. 45 is a graph that illustrates data representing the intensity ratio measured in the apparatus illustrated in FIGS. 44A and 44B, whereby the two photodetectors were positioned away from the laser impact point at angular positions of about 90 degrees and about 135 degrees along the circumference of the bottle.

FIG. 45 is a graph that illustrates data representing the intensity ratio measured in the blood culture optical measurement system of FIGS. 44A and 44B, whereby the first and second photodetectors were positioned away from the first point of impact at angular positions of about 90 degrees and about 135 degrees respectively along the circumference of the bottle. (The apparatus was otherwise configured and used the same components, as described in Example 1.) FIG. 45 shows the ratio between the photocurrents as recorded by the first photodetector and the second photodetector, which corresponds to a backscatter intensity ratio of the first and the second locations. All measurements illustrated in FIG. 45 were made using blood with a hematocrit value of about 35%. As can be seen in FIG. 45, the ratio is proportional to the volume of the mixture in the third bottle within the volume range of about 0.5 to 10 mL. The advantage of an arrangement according to FIGS. 44A and 44B is its simplicity. No imaging or moving photodetectors are required, and only two photocurrents have to be processed.

The present invention has been described with reference to several exemplary embodiments. It will be readily apparent to those skilled in the art, however, that it is possible to embody the invention in specific forms other than those of the exemplary embodiments described above. This may be done without departing from the spirit and scope of the invention. The exemplary embodiments are merely illustrative and should not be considered restrictive in any way. The scope of the invention is given by the appended claims, rather than the preceding description, and all variations and equivalents, which fall within the range of the claims, are intended to be embraced therein.

What is claimed is:

1. A system for performing optical measurements on a container comprising a liquid, the system comprising:
    an optical source adapted to direct a light beam onto a wall of the container at a first location, wherein the light beam deviates from a normal to the container wall at the first location by a first angle, generating an asymmetric spatial distribution of backscattered light from the liquid near the first location;
    an imaging device adapted to image the asymmetric spatial distribution of backscattered light wherein the imaging device is located to substantially avoid imaging the portions of the light beam reflected by outer and inner bottle wall surfaces;
    an imaging detector adapted to record at least parts of the imaged asymmetric spatial distribution of backscattered light; and
    a data analyzing system connected to the imaging detector adapted to extract analytical features of the asymmetric spatial distribution of backscattered light.

2. A system according to claim 1, further comprising a cylindrical container comprising a liquid.

3. A system according to claim 2, wherein the container is a blood culture bottle comprising blood and growth media.

4. A system according to claim 3, wherein the data analyzing system is further adapted to provide data to determine at least one parameter selected from the group consisting of the presence or absence of a developed microorganism population, the volume of the liquid sample, and the hematocrit value of the liquid sample.

5. A system according to claim 4, wherein the data analyzing system comprises synchronous detection devices.

6. A system according to claim 2, wherein the optical source is adapted to produce the light beam to propagate within a plane substantially perpendicular or substantially parallel to the container's axis of symmetry.

7. A system according to claim 2, wherein the first location is on a cylindrical part of the container.

8. A system according to claim 2, wherein the first location is on a non-cylindrical part of the container.

9. A system according to claim 8, wherein the first location is on the bottom of the container.

10. A system according to claim 1, wherein the optical source is selected from the group consisting of a laser and a light emitting diode.

11. A system according to claim 1, wherein the optical source is adapted to emit light with a wavelength of about 500 to about 1500 nm.

12. A system according to claim 11, wherein the optical source is adapted to emit light with a wavelength of about 640 to about 720 nm.

13. A system according to claim 1, wherein the optical source is adapted to modulate the intensity of the light beam.

14. A system according to claim 1, wherein the first angle is between about zero and about 90 degrees.

15. A system according to claim 14, wherein the first angle is between about 25 and about 45 degrees.

16. A system according to claim 15, wherein the first angle is about 35 degrees.

17. A system according to claim 1, wherein the imaging device is selected from the group consisting of a lens and an array of optical fibers.

18. A system according to claim 1, wherein the imaging device is adapted to move along an axis to record at least parts of the imaged asymmetrical spatial distribution of backscattered light.

19. A system according to claim 1, wherein the imaging detector is a photodetector.

20. A system according to claim 19, wherein the photodetector is selected from the group consisting of an opto-electronic camera, a digital 2D camera, a 2D CCD array and a linear CCD array.

21. A system according to claim 19, wherein the photodetector is adapted to move along an axis to record at least parts of the imaged asymmetrical spatial distribution of backscattered light.

22. A method for performing optical measurements on a container comprising:
    providing a container comprising a liquid sample;
    directing a light beam onto an optically transparent wall of the container at a first location, such that the light beam deviates from a normal to the container wall at the first location by a first angle, generating an asymmetric spatial distribution of backscattered light from the liquid sample in the container near the first location;
    detecting at least a portion of the asymmetric spatial distribution of backscattered light while substantially avoiding detecting portions of the light beam reflected by outer and inner container wall surfaces; and
    extracting analytical features from the asymmetric spatial distribution of backscattered light.

23. A method according to claim 22, wherein the light beam is directed from an optical source selected from the group consisting of a laser and a light emitting diode.

24. A method according to claim 23, wherein the optical source is adapted to provide an intensity-modulated light beam.

25. A method according to claim 22, further comprising:
    directing the light from the source through a lens, to focus the beam onto the wall of the container.

26. A method according to claim 22, wherein the step of directing the light beam comprises:
    emitting a light beam at a wavelength of about 500 nm to about 1500 nm.

27. A method according to claim 26, wherein the wavelength is about 640 nm to about 720 nm.

28. A method according to claim 22, wherein the container is a cylindrical bottle, and wherein the light beam propagates within a plane substantially perpendicular or substantially parallel to the bottle's axis of symmetry.

29. A method according to claim 22, further comprising the step of:
    imaging the asymmetric spatial distribution through an imaging device.

30. A method according to claim 29, wherein the imaging device is selected from a lens and an array of optical fibers.

31. A method according to claim 29, wherein the detecting step comprises detecting at least parts of the imaged spatial distribution of backscattered light with a photodetector.

32. A method according to claim 31, wherein the photodetector is selected from the group consisting of an opto-electronic camera, a digital 2D camera, a 2D CCD array and a linear CCD array.

33. A method according to claim 22, wherein the liquid sample comprises blood and growth media, and wherein the step of extracting analytical features from the asymmetric spatial distribution of backscattered light comprises:
    analyzing data to determine at least one parameter selected from the group consisting of the presence or absence of a developed microorganism population, the volume of the liquid sample, and the hematocrit value of the liquid sample.

34. A method according to claim 33, wherein the analyzing of data is performed by a data analyzing system connected to an imaging detector, wherein the data analyzing system is adapted to record at least parts of the imaged spatial distribution of backscattered light.

35. A method according to claim 34, wherein the data analyzing system comprises synchronous detection devices.

36. A method according to claim 22, wherein the first angle is between about zero and about 90 degrees.

37. A method according to claim 36, wherein the first angle is between about 25 and about 45 degrees.

38. A method according to claim 37, wherein the first angle is about 35 degrees.

39. A method according to claim 22, wherein the container is cylindrical, and wherein the first location is on a cylindrical part of the container.

40. A method according to claim 22, wherein the container is cylindrical, and wherein the first location is on a non-cylindrical part of the container.

41. A method according to claim 40, wherein the first location is on the bottom of the container.

42. A method according to claim 22, further comprising the step of:
moving the imaging detector along an axis to record parts of the asymmetrical spatial distribution of backscattered light.

43. A method comprising the steps of:
providing a container comprising a sample that comprises growth media and blood;
directing a light beam onto an optically transparent wall area of the container at a first location, such that the light beam deviates from a normal to the container wall at the location by a first angle, generating an asymmetric spatial distribution of backscattered light from the mixture of growth media and blood in the container near the first location;
detecting at least a portion of the asymmetric spatial distribution of backscattered light from the mixture of growth media and blood in the container near the first location with a detecting device while substantially avoiding detecting portions of the light beam reflected by outer and inner container wall surfaces;
extracting analytical features from the asymmetric spatial distribution of backscattered light; and
determining the volume and the hematocrit value of the sample in the sealable container by comparing the extracted analytical features or data generated therefrom with calibration information.

44. A method according to claim 43 further comprising the step of imaging the asymmetric spatial distribution through an imaging device.

45. A method according to claim 44, wherein the imaging is performed into a plane.

46. A method according to claim 43, wherein the step of extracting comprises:
using a data analyzing system connected to the detecting device, wherein the detecting device comprises a photodetector, and wherein the data analyzer system is adapted to record at least parts of the asymmetric spatial distribution of backscattered light and is further adapted to extract the analytical features from the recorded asymmetric spatial distribution of backscattered light.

47. A method according to claim 43 wherein the step of extracting comprises:
extracting one or more features selected from the group consisting of a maximum recorded backscattering intensity (IMAX) analytical feature, a backscattering intensity at the light impact point (IALIP) analytical feature, a full-width-at-half-IMAX (FWHM) analytical feature, and a slope of the slowly decaying flank of the asymmetric spatial distribution of backscattered light (SL) analytical feature.

48. A method according to claim 47 wherein the extracted analytical features are extracted from the asymmetric spatial distribution of backscattered light as measured along the X-axis, wherein the X-axis is oriented along the container wall within a plane comprising the light beam, and wherein the extracted analytical features comprise a full-width-at-half-IMAX in the X-axis (FWHMX) and a slope in the X-axis (SLX).

49. A method according to claim 48, wherein the slope SLX is an inverse of the distance along the X-axis of a recorded light distribution over which the intensity decreases by a first factor.

50. A method according to claim 48, further comprising the step of extracting the full-width-at-half-IALIP (FWHMX*) as measured along the X-axis.

51. A method according to claim 47, wherein the extracted analytical features are extracted from the asymmetric spatial distribution of backscattered light as measured along the Y-axis, wherein the Y-axis is oriented along the container wall within a plane perpendicular to the container wall; wherein the asymmetrical spatial distribution comprises the area of IMAX, but extending perpendicular to the X-axis; and wherein the extracted analytical features comprise a full-width-at-half-IMAX in the Y-axis (FWHMY) and a slope in the Y-axis (SLY).

52. A method according to claim 51, wherein the slope SLY is an inverse of a distance along the Y-axis of a recorded light distribution over which the intensity decreases by a second factor.

53. A method according to claim 51, further comprising the step of extracting a slope measured along a Y-direction parallel to the Y-axis in a plane comprising the area of IALIP.

54. A method according to claim 51, further comprising the step of extracting the width FWHMY*; and wherein FWHMY* is a full-width-at-half-IALIP and is measured along a Y-direction parallel to the Y-axis in a plane comprising the area of IALIP.

55. A method according to claim 51, wherein a slope SLY* is an inverse of the distance along the Y-axis of a recorded light distribution over which the intensity decreases by a third factor.

56. A method according to claim 43, wherein the step of extracting comprises:
accumulating the number of pixels in a two-dimensional image of the asymmetrical spatial distribution of backscattered light having a pixel intensity that exceeds a first threshold.

57. A method according to claim 43, wherein the step of extracting comprises:
summing substantially all pixel intensities in a two-dimensional image of the asymmetrical spatial distribution of backscattered light.

58. A method according to claim 43, wherein the step of determining comprises:
generating a first processed analytical feature by combining two or more of the extracted analytical features; and
determining the combination of the volume and the hematocrit value of the blood culture based on the first processed analytical feature.

59. A method according to claim 43, wherein the step of determining comprises calculating the mathematical product of the volume and the hematocrit value.

60. A method comprising the steps of:
providing a container comprising a sample that comprises growth media and blood;
directing a light beam onto an optically transparent wall area of the container at a first location, such that the light beam deviates from a normal to the container wall at the first location by a first angle, generating an asymmetric spatial distribution of backscattered light from the mixture of growth media and blood in the container near the first location;
detecting at least a portion of the asymmetric spatial distribution of backscattered light from the mixture of growth media and blood in the sealable container near the first location with a detecting device while substantially avoiding detecting portions of the light beams reflected by outer and inner container wall surfaces;
extracting analytical features from the asymmetric spatial distribution of backscattered light; and
determining a presence or absence of a developed micro-organism population within the container by comparing the extracted analytical features or data generated therefrom with calibration information.

61. A method according to claim 60, further comprising the step of imaging the asymmetric spatial distribution through an imaging device.

62. A method according to claim 61, wherein the imaging is performed into a plane.

63. A method according to claim 61, wherein the step of determining comprises:
generating a first processed analytical feature by combining two or more of the extracted analytical features;
comparing the first processed analytical feature with a first constant, and determining that the blood culture bottle is absent of developed micro-organisms if the first processed analytical feature is greater than the first constant; and
determining that the presence of developed micro-organisms is likely in the blood culture bottle if the first processed analytical feature is less than the first constant.

64. A method according to claim 63, further comprising:
comparing the first processed analytical feature with a second constant if it has been determined that the first processed analytical feature is less than the first constant.

65. A method according to claim 63, wherein the first processed analytical feature is generated according to the following equation:

$$Q5 = \frac{10^4 * (IALIP * FWHM)^{1.5}}{SL}.$$

66. A method according to claim 63, wherein the first constant is about 2.5 and the second constant is about 1.3.

67. A method according to claim 60, wherein the step of extracting comprises:
using a data analyzing system connected to the detecting device; wherein the detecting device comprises a photodetector; and wherein the data analyzing system is adapted to record at least parts of the asymmetric spatial distribution of backscattered light and is further adapted to extract analytical features from the recorded asymmetric spatial distribution of backscattered light.

68. A method according to claim 60, wherein the step of extracting comprises:
extracting one or more features selected from the group consisting of a maximum recorded backscattering intensity (IMAX) analytical feature, a backscattering intensity at the light impact point (IALIP) analytical feature, a full-width-at-half-IMAX (FWHM) analytical feature, and a slope of the slowly decaying flank of the asymmetric spatial distribution of backscattered light (SL) analytical feature.

69. A method according to claim 68, wherein the extracted analytical features are extracted from the asymmetric spatial distribution of backscattered light as measured along the X-axis, wherein the X-axis is oriented along the container wall within a plane comprising the light beam; and wherein the extracted analytical features comprise a full-width-at-half-IMAX in the X-axis (FWHMX) and a slope in the X-axis (SLX).

70. A method according to claim 69, wherein the slope SLX is an inverse of a distance along the X-axis of a recorded light distribution over which the intensity decreases by a first factor.

71. A method according to claim 69, further comprising the step of extracting a full-width-at-half-IALIP (FWHMX*) as measured along the X-axis.

72. A method according to claim 68, wherein the extracted analytical features are extracted from the asymmetric spatial distribution of backscattered light as measured along the Y-axis, wherein the Y-axis is oriented along the bottle wall within a plane perpendicular to the bottle wall; wherein the asymmetric spatial distribution comprises the area of IMAX, but extending perpendicular to the X-axis; and wherein the extracted analytical features comprise a full-width-at-half-IMAX in the Y-axis (FWHMY) and a slope in the Y-axis (SLY).

73. A method according to claim 72, wherein the slope SLY is an inverse of a distance along the Y-axis of a recorded light distribution over which the intensity decreases by a second factor.

74. A method according to claim 72, further comprising the step of extracting a slope measured along a Y-direction parallel to the Y-axis in a plane comprising the area of IALIP.

75. A method according to claim 72, further comprising the step of extracting is a width FWHMY*; and wherein FWHMY* is a full-width-at-half-IALIP and is measured along a Y-direction parallel to the Y-axis in a plane comprising the area of IALIP.

76. A method according to claim 72, wherein a slope SLY* is an inverse of a distance along the Y-axis of a recorded light distribution over which the intensity decreases by a third factor.

77. A method according to claim 60, wherein the step of extracting comprises:
accumulating a number of pixels in a two-dimensional image of the asymmetrical spatial distribution of backscattered light having a pixel intensity that exceeds a first threshold.

78. A method according to claim 60, wherein the step of extracting comprises:
summing substantially all pixel intensities in a two-dimensional image of the asymmetrical spatial distribution of backscattered light.

79. A method according to claim 60, wherein the step of determining comprises:
plotting, or performing a calculation indicative of such plotting, two or more of the extracted analytical features of the container on a two-dimensional graph along with the identical extracted analytical features from a calibration set; and verifying the presence or absence of the developed micro-organisms based on the proximity of the plotted extracted analytical features of the container with that of the plotted extracted analytical features of the control blood culture bottle.

80. A method comprising the steps of:

providing a container comprising a sample that comprises growth media and blood;

directing a light beam onto an optically transparent wall area of the container at a first location, such that the light beam deviates from a normal to the container wall at the first location by a first angle, generating an asymmetric spatial distribution of backscattered light from the mixture of growth media and blood in the container near the first location;

detecting at least portions of the asymmetric spatial distribution of backscattered light from the mixture of growth media and blood in the container near the first location with a detecting device while substantially avoiding detecting portions of the light beams reflected by outer and inner container wall surfaces;

extracting analytical features from the asymmetric spatial distribution of backscattered light; and determining the presence of a developed micro-organism population within the blood culture bottle by comparing the generated data with calibration information by repeating the steps of directing, detecting, extracting and determining one or more times.

81. A method according to claim 80, wherein the repeating is performed at intervals of about ten minutes.

82. A method according to claim 81, wherein the repeating is performed at the intervals of about ten minutes, for a period of about five days.

* * * * *